United States Patent
Gough et al.

(10) Patent No.: US 6,737,124 B2
(45) Date of Patent: May 18, 2004

(54) LIQUID CRYSTAL COMPOUNDS HAVING A SILANE TAIL WITH A PERFLUOROALKYL TERMINAL PORTION

(75) Inventors: Neil Gough, Longmont, CO (US); Xin-Hua Chen, Erie, CO (US); William N. Thurmes, Longmont, CO (US); Michael Wand, Boulder, CO (US)

(73) Assignee: Displaytech, Inc., Longmont, CO (US)

( * ) Notice: Subject to any disclaimer, the term of this patent is extended or adjusted under 35 U.S.C. 154(b) by 300 days.

(21) Appl. No.: 09/753,749

(22) Filed: Jan. 3, 2001

(65) Prior Publication Data

US 2003/0003245 A1 Jan. 2, 2003

Related U.S. Application Data

(60) Provisional application No. 60/256,229, filed on Dec. 15, 2000.

(51) Int. Cl.[7] .................. C09K 19/34; C09K 19/30; C09K 19/12; C07F 7/08; C07C 22/04; C07D 239/02; C07D 319/06
(52) U.S. Cl. .............. 428/1.1; 252/299.61; 252/299.63; 252/299.66; 544/229; 544/303; 549/380; 549/214; 556/430; 556/431; 570/162
(58) Field of Search ................. 252/299.61, 299.62, 252/299.63, 299.66; 428/1.1; 570/127, 142, 162; 556/430, 431; 544/303, 229; 549/380, 214

(56) References Cited

U.S. PATENT DOCUMENTS

| | | | |
|---|---|---|---|
| 5,051,506 A | 9/1991 | Wand et al. | 544/289 |
| 5,061,814 A | 10/1991 | Wand et al. | 549/560 |
| 5,130,048 A | 7/1992 | Wand et al. | 252/299 |
| 5,167,855 A | 12/1992 | Wand et al. | 252/299.01 |
| 5,178,791 A | 1/1993 | Wand et al. | 252/299.6 |
| 5,178,793 A | 1/1993 | Vohra et al. | 252/299.61 |
| 5,180,520 A | 1/1993 | Wand et al. | 252/299.61 |
| 5,271,864 A | 12/1993 | Wand et al. | 252/299.61 |
| 5,278,680 A | 1/1994 | Karasawa et al. | 359/40 |
| 5,380,460 A | 1/1995 | Wand et al. | 252/299.6 |
| 5,422,037 A | 6/1995 | Wand et al. | 252/299.61 |
| 5,453,218 A | 9/1995 | Wand et al. | 252/299.01 |
| 5,457,235 A | 10/1995 | Wand et al. | 568/65 |
| 5,539,555 A | 7/1996 | Wand et al. | 359/100 |
| 5,543,078 A | 8/1996 | Walba et al. | 252/299.65 |
| 5,585,036 A | 12/1996 | Wand et al. | 252/299.01 |
| 5,626,792 A | 5/1997 | Wand et al. | 252/299.01 |
| 5,637,256 A | 6/1997 | Walba et al. | 252/299.66 |
| 5,658,493 A | 8/1997 | Walba et al. | 252/299.01 |
| 5,753,139 A | 5/1998 | Wand et al. | 252/299.01 |
| 5,866,036 A | 2/1999 | Wand et al. | 252/299.6 |
| 6,139,771 A | 10/2000 | Walba et al. | 252/299.01 |

OTHER PUBLICATIONS

Inui, S. et al. (1996), "Thresholdless antiferroelectricity in liquid crystals and its application to displays," J. Mater. Chem. 6(4):671–673.

Seomun, S.S. et al. (1997), "Evolution of Switching Characteristics from Tristable to V–Shaped in an Apparently Antiferroelectric Liquid Crystal," Jpn. J. Appl. Phys. 36:3586–3590.

*Primary Examiner*—Shean C. Wu
(74) *Attorney, Agent, or Firm*—Greenlee, Winner, and Sullivan, P.C.

(57) ABSTRACT

Chiral nonracemic, chiral racemic and achiral compounds useful as component of LC compositions which have a silane tail group which is partially fluorinated. The silane tail group comprises a perfluoroalkyl group. The silane tail group of this invention has the formula:

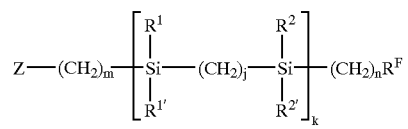

where k is 0 or an integer ranging from 1–10; m and n are integers ranging from 1 to about 20; j is 0 or an integer ranging from 1 to 20; Z is —O— or a single bond; $R^1$, $R^{1'}$, $R^2$ and $R^{2'}$ are alkyl groups or perfluorinated alkyl groups; and $R^F$ is a perfluorinated alkyl group. The invention also provides LC compositions comprising one or more compounds of the invention with partially fluorinated silane tails. The invention also provides optical devices, particularly display devices which contain an aligned layer of an LC composition comprising one or more silane compounds of this invention.

41 Claims, No Drawings

LIQUID CRYSTAL COMPOUNDS HAVING A SILANE TAIL WITH A PERFLUOROALKYL TERMINAL PORTION

CROSS-REFERENCE TO RELATED APPLICATIONS

This application takes priority under 119(e) from U.S. provisional application serial No. (60/256,229) filed Dec. 15, 2000. This provisional application is incorporated by reference in its entirety herein to the extent that it is not inconsistent with the disclosure herein.

BACKGROUND OF THE INVENTION

The present invention relates to compounds useful as components in liquid crystal (LC) compositions, particularly as components of LC compositions that exhibit smectic phases and more particularly as components of LC compositions that exhibit smectic A and/or smectic C phases. LC compositions of this invention may also exhibit nematic phases. LC compositions of this invention can be ferroelectric liquid crystals (FLCs). The invention also relates to optical devices employing LC compositions of the invention in optical switching and display elements.

Several types of smectic liquid crystal materials (LCs) have been investigated for rapid switching, view-angle enhancement and higher contrast, including surface-stabilized ferroelectric LCs (FLCs), deformed helix ferroelectric LCs (DHFLCs), and antiferroelectric LCs (AFLCs). Recently, smectic material exhibiting thresholdless or more properly V-shaped switching LCs (VLCs) have been described (Inui, S. et al. (1996) J. Mater. Chem. 6(4) :671–673; Seomun, S. S. et al. (1997) Jpn. J. Appl. Phys. 36:3580–3590). Ferroelectric LCs when a ligned parallel to the substrate surfaces using the surface stabilized effect (in an surface-stabilized ferroelectric liquid crystal (SSFLC) device) exhibit two stable state switching on a microsecond time scale. Antiferroelectric LCs exhibit three stable-state switching, which by application of a bias field can be converted for use in a bistable switching mode LC devices. Two of the AFLC states have the same transmittance, so that alternate symmetrical switching can be used in AFLC devices. VLCs, in contrast, exhibit very rapid, analog electro-optic response, allow symmetrical driving, and no dc balance is required. VLCs are particularly attractive for applications requiring generation of multiple levels of gray scale.

Liquid crystal (LC) compositions exhibit one or more LC phases. LC compositions may be composed of one or more components. Components of LC compositions may exhibit liquid crystal phases, have latent liquid crystal phases or be compatible with (not suppress) liquid crystal phases in the LC composition. LC compounds and components of LC mixtures of this invention are rod-like molecules most typically having a generally linear mesogenic core with one or more directly or indirectly linked alicyclic or aromatic rings (which may be fused aromatic rings) and linear or branched tail groups distributed on either side of the mesogenic core, e.g.:

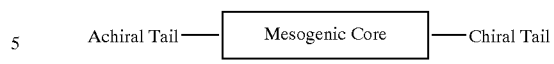

LC components which do not themselves exhibit liquid crystal phases, but which exhibit LC phases on combination with one or more other components are described as having "latent" liquid crystal phases. Chiral nonracemic LCs useful in FLCS, DHFLCS, AFLC and VLCS compositions have at least one component that has a chiral non-racemic tail group. FLCS, DHFLCS, AFLC and VLCS compositions may be composed entirely of chiral non-racemic components, but are typically composed of a mixture of chiral nonracemic and achiral or racemic components.

SUMMARY OF THE INVENTION

The invention relates to liquid crystal compounds having silane tails having a perfluoroalkyl terminal portion which are useful as components in liquid crystal compositions, particularly those compositions exhibiting smectic liquid crystal compositions and more particularly those exhibiting chiral smectic phases, such as smectic C phases. Silanes of this invention can be chiral nonracemic, chiral racemic or achiral molecules. Chiral racemic and achiral silanes of this invention are useful alone or in combination as liquid crystal host materials. The materials of this invention can also be combined with known liquid crystal host materials to impart improved properties. Chiral nonracemic silanes of this invention can function as additives or dopants in host materials to impart chirality into an LC material. When introduced into host materials the silanes of this invention tend to broaden the smectic C phase of the material and to improve alignment of the material in a liquid crystal cell. Of particular interest are compound which are disilanes.

The invention relates to liquid crystal materials comprising liquid crystal compounds having a silane tail with a terminal perfluoroalkyl portion attached to a linear rod-like liquid crystal core. LC compounds of this invention include compounds having the formula:

Formula I

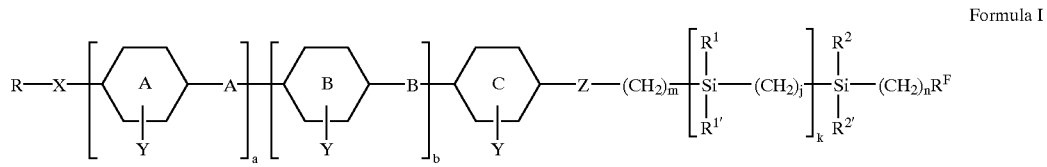

where:
  a and b can be 1 or 0 to indicate the presence or absence of a structural element; k is 0 or an integer ranging from 1–10; preferably k is 0 or 1;
  m and n are integers ranging from 1 to about 20; j is 0 or an integer ranging from 1 to 20, n+m+k(j) ranges from about 5 to about 20;
  one or more non-neighboring carbons in the —$(CH_2)m$— group or the —$(CH_2)n$— group of the silane tail can be replaced with a double bond, a triple bond or an oxygen, preferably only one carbon of these groups is replaced, more preferably no carbons of the groups are replaced;

A and B, independently are linker groups selected from the group consisting of a single bond, —COO—, —OOC—. —CH$_2$—CH$_2$—, —OCH$_2$—, —CH$_2$—O—, —CH=CH— (cis or trans), —CH=CH—CH=CH— (cis or trans) and —C≡C—;

Z is —O— or a single bond;

X is —O—, —COO— or —OCO—, or a single bond;

Y indicates optional substitution on the core ring and can represent up to four substituents when the rings are aromatic and up to 10 substituents when the rings are alicyclic, substituents include halides, CN, NO$_2$, alkyl (lower alkyl having 1–6 carbon atoms), alkoxy (lower alkoxy having 1–6 carbon atoms), preferred core ring substituents are fluorine;

R is an alkyl or alkenyl group having from 3 to about 20 carbons atoms in which one or more of the non-neighboring carbons can be replaced with —O—, or in which one or more of the carbons is substituted with one or more halogens, particularly one or more fluorines, or R is R*, a chiral non-racemic group, which can be a chiral nonracemic alkyl or alkenyl group, a chiral nonracemic halogen (particularly fluorine) substituted alkyl or alkenyl group, a group containing a cyclic lactone ring (as illustrated in Scheme 3) or a chiral nonracemic epoxide (as illustrated in Scheme 3).

$R^1$, $R^{1'}$, $R^2$ and $R^{2'}$ are alkyl groups or perfluorinated alkyl groups, typically having from 1 to 6 carbon atoms, and particularly —CH$_3$ groups;

$R^F$ is a perfluorinated alkyl group having from 1 to about 10 carbon atoms;

Core rings A, B and C can be aromatic or alicyclic and preferably are 5- or 6-membered rings.

One of the rings in the core can be replaced with a single fused ring aromatic, such as a naphthalene ring, or a partially aromatic ring, such as a dehydronaphthalene ring. for aromatic rings one or two ring carbons can be replaced with O, S, or N, preferably N. Alicyclic rings can have from 3 to about 10 carbon atoms in the ring, but cyclohexane and cyclohexene rings are preferred. In alicyclic rings one or two of the CH2 groups of the ring can be replaced with a NH, O, S or C=O group. The core can contain one, two or three rings. R can be $R^F$ or a partially perfluorinated tail. R can have a terminal portion that is perfluorinated, such as in the formula: —X(CH2)p CqFq+1, where p is an integer ranging from 1 to 20 and q is an integer ranging from 1 to 20 (preferably p and q range from 1 to 10). Preferred one ring cores are aromatic (phenyl, pyrimidinyl, pyridinyl). Preferably two or three of the A, B and C rings are aromatic. Preferred cores include: phenylpyrimidines, phenylbenzoates, biphenyls, and terphenyls. Preferably one or two of the rings A, B or C is alicyclic. Scheme 4 illustrates a number of exemplary cores of the compounds of this invention.

In a specific embodiment, compounds of this invention have the formula:

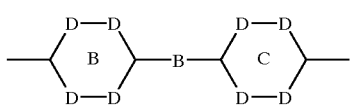

Formula II where B, Ring B and Ring C can take values as noted above and each D, independent of other D's, can be CH or CH$_2$, a nitrogen atom, CY or CHY, where Y is a CN, NO$_2$, an alkyl, a perhaloalkyl (e.g., perfluoroalkyl), or a halide, particularly a fluorine. Rings B and C can be alicyclic or aromatic and B and C that are aromatic can be fused ring systems, such as naphthalene. One of B or C can also be a fused ring system that is partially aromatic, such as a dehydronaphthalene ring system. In particular embodiments, both of rings B and C are aromatic, or one of B and C is aromatic and the other of B or C is alicyclic, particularly a cyclohexane or cyclohexene ring. In preferred embodiments: (1) all D's are CH; (2) one or two D's are N and the remaining D's are CH; (3) one or two D's are CF and the remaining D's are CH; (4) one or two D's are N, one or two D's are CF and the remaining D's are CH; (3) all D's on one ring are CH$_2$ and one, two or three D's on the other ring can be N or CF; (4) all D's on one ring are CH$_2$ and all D's on the other ring are CH.

In a further specific embodiment, compounds of this invention have the formula:

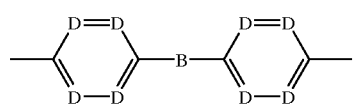

Formula III where each D independent of other D's can be CH or CY as defined above or a nitrogen atom and all other variables are as defined above. In preferred compounds of Formula III, all D's are CH or one or two D's can be CF or nitrogen with the remaining D's being CH. In preferred embodiments, the core is a phenylpyrimidine, a phenylpyridine, phenylbenzoate, or biphenyl.

In another specific embodiment, compounds of this invention can have the formula:

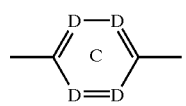

Formula IV where each D, independent of other D's, can be CH, CY or a nitrogen. In preferred compounds of Formula IV, all D's are CH or one or two D's can be CF or nitrogen with the remaining D's being CH.

In yet another specific embodiment, compounds of this invention can have the formula:

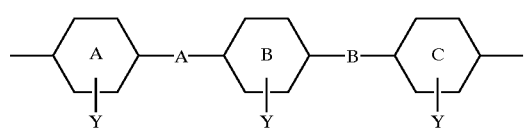

Formula V where variable have the values listed in Formula I above. In particular embodiments the core can be (1) an optionally substituted terphenyl, where the preferred substitution is one or two F's; (2) a core in which A or C is a cyclohexane or cyclohexene ring and the remaining rings are aromatic; (3) a core in which A or C is a cyclohexane or cyclohexene and the remaining rings are selected from phenyl rings, phenyl rings substituted with one or two F's, pyrimidine rings or pyridine rings; (4) a core in which A or C is a cyclohexane or cyclohexene and the remaining tow rings represent a phenylpyrimidine, a phenylpyridine, a phenyl benzoate or a biphenyl.

Compounds of Formulas I–V are useful in the preparation of LC and FLC compositions which in turn are useful in various optical device applications. Subsets of compounds of Formula I–V that are useful in the preparation of LC and FLC compositions include those in which:

n=2;

n=1;

$R^F$ is $CF_3$;

$R^F$ is $C_4F_9$;

$R^F$ is $C_6F_{13}$;

m is 5–10;

$R^1$, $R^{1'}$, $R^2$ and $R^{2'}$ are all methyl;

k is 0;

k is 1;

j is 1 or 2;

Z is oxygen,

Z is a single bond;

X is oxygen;

R is alkyl;

RX is alkoxy;

R is a partially fluorinated tail;

R is $R^F$;

R has the formula: —X(CH2)p CqFq+1, where p is an integer ranging from 2 to 10 and q is is an integer ranging from 1 to 8;

k is 0 and n=2, $R^F$ is $CF_3$; m is 5–10; and $R^2$ and $R^{2'}$ are both methyl;

n=2, $R^F$ is $CqF_{q+1}$, where q is 2–8; m is 5–10; and $R^2$ and $R^{2'}$ are both methyl;

n=1, $R^F$ is $CF_3$; m is 5–10; and $R^2$ and $R^{2'}$ are both methyl;

n=2, $R^F$ is $CqF_{q+1}$, where q is 2–8; m is 5–10; and $R^2$ and $R^{2'}$ are both methyl;

n=2, $R^F$ is $CF_3$; m is 5–10; Z is O and $R^2$ and $R^{2'}$ are both methyl;

n=2, $R^F$ is $CqF_{q+1}$, where q is 2–8; m is 5–10, Z is O and $R^2$ and $R^{2'}$ are both methyl;

n=1, $R^F$ is $CF_3$; m is 5–10, Z is O, and $R^2$ and $R^{2'}$ are both methyl;

n=2, $R^F$ is $CqF_{q+1}$, where q is 2–8; m is 5–10; Z is O and $R^2$ and $R^{2'}$ are both methyl;

k is 1, j is 1 and n=2, $R^F$ is $CF_3$; m is 5–10; and $R^1$, $R^{1'}$, $R^2$ and $R^{2'}$ are all methyl;

n=2, $R^F$ is $CqF_{q+1}$, where q is 2–8; m is 5–10; and $R^1$, $R^{1'}$, $R^2$ and $R^{2'}$ are all methyl;

n=1, $R^F$ is $CF_3$; m is 5–10; and $R^1$, $R^{1'}$, $R^2$ and $R^{2'}$ are all methyl;

n=2, $R^F$ is $CqF_{q+1}$, where q is 2–8; m is 5–10; and $R^1$, $R^{1'}$, $R^2$ and $R^{2'}$ are all methyl;

n=2, $R^F$ is $CF_3$; m is 5–10; Z is O and $R^1$, $R^{1'}$, $R^2$ and $R^{2'}$ are all methyl;

n=2, $R^F$ is $CqF_{q+1}$, where q is 2–8; m is 5–10, Z is O and $R^1$, $R^{1'}$, $R^2$ and $R^{2'}$ are all methyl;

n=1, $R^F$ is $CF_3$; m is 5–10, Z is O, and $R^1$, $R^{1'}$, $R^2$ and $R^{2'}$ are all methyl;

n=2, $R^F$ is $CqF_{q+1}$, where q is 2–8; m is 5–10; Z is O and $R^1$, $R^{1'}$, $R^2$ and $R^{2'}$ are all methyl;

R is alkyl;

R is alkoxy

R is alkyl and n=2, $R^F$ is $CF_3$; m is 5–10; and $R^2$ and $R^{2'}$ are both methyl;

n=2, $R^F$ is $CqF_{q+1}$, where q is 2–8; m is 5–10; and $R^2$ and $R^{2'}$ are both methyl;

n=1, $R^F$ is $CF_3$; m is 5–10; and $R^2$ and $R^{2'}$ are both methyl;

n=2, $R^F$ is $CqF_{q+1}$, where q is 2–8; m is 5–10; and $R^2$ and $R^{2'}$ are both methyl;

n=2, $R^F$ is $CF_3$; m is 5–10; Z is O and $R^2$ and $R^{2'}$ are both methyl;

n=2, $R^F$ is $CqF_{q+1}$, where q is 2–8; m is 5–10, Z is O and $R^2$ and $R^{2'}$ are both methyl;

n=1, $R^F$ is $CF_3$; m is 5–10, Z is O, and $R^2$ and $R^{2'}$ are both methyl; or n=2, $R^F$ is $CqF_{q+1}$, where q is 2–8; m is 5–10; Z is O and $R^2$ and $R^{2'}$ are both methyl;

RX is alkoxy and n=2, $R^F$ is $CF_3$; m is 5–10; and $R^2$ and $R^{2'}$ are both methyl;

n=2, $R^F$ is $CqF_{q+1}$, where q is 2–8; m is 5–10; and $R^2$ and $R^{2'}$ are both methyl;

n=1, $R^F$ is $CF_3$; m is 5–10; and $R^2$ and $R^{2'}$ are both methyl;

n=2, $R^F$ is $CqF_{q+1}$, where q is 2–8; m is 5–10; and $R^2$ and $R^{2'}$ are both methyl;

n=2, $R^F$ is $CF_3$; m is 5–10; Z is O and $R^2$ and $R^{2'}$ are both methyl;

n=2, $R^F$ is $CqF_{q+1}$, where q is 2–8; m is 5–10, Z is O and $R^2$ and $R^{2'}$ are both methyl;

n=1, $R^F$ is $CF_3$; m is 5–10, Z is O, and $R^2$ and $R^{2'}$ are both methyl; or n=2, $R^F$ is $CqF_{q+1}$, where q is 2–8; m is 5–10; Z is O and $R^2$ and $R^{2'}$ are both methyl; or RX is a chiral nonracemic tail, particularly a tail illustrated in Scheme 3, and n=2, $R^F$ is $CF_3$; m is 5–10; and $R^2$ and $R^{2'}$ are both methyl;

n=2, $R^F$ is $CqF_{q+1}$, where q is 2–8; m is 5–10; and $R^2$ and $R^{2'}$ are both methyl;

n=1, $R^F$ is $CF_3$; m is 5–10; and $R^2$ and $R^{2'}$ are both methyl;

n=2, $R^F$ is $CqF_{q+1}$, where q is 2–8; m is 5–10; and $R^2$ and $R^{2'}$ are both methyl;

n=2, $R^F$ is $CF_3$; m is 5–10; Z is O and $R^2$ and $R^{2'}$ are both methyl;

n=2, $R^F$ is $CqF_{q+1}$, where q is 2–8; m is 5–10, Z is O and $R^2$ and $R^{2'}$ are both methyl; or n=1, $R^F$ is $CF_3$; m is 5–10, Z is O, and $R^2$ and $R^{2'}$ are both methyl;

n=2, $R^F$ is $CqF_{q+1}$, where q is 2–8; m is 5–10; Z is O and $R^2$ and $R^{2'}$ are both methyl.

All numerical ranges for variables that are integers or other numbers are inclusive.

The invention provides LC compositions comprising one or more of the compounds of this invention as described above. LC compositions of the invention include those that contain sufficient amounts of the compounds of this invention to have a substantial effect upon the physical or optical properties of the LC composition in which they are combined or to which they are added. A substantial effect upon the physical or optical properties of the LC compositions includes, among others, a significant change in a LC property of the composition, birefringence, switching speed, alignment or contrast. LC compositions of this invention include those that contain from about 1% to 100% by weight of one or more compounds of this invention. LC compositions of this invention include those that contain 3% or more of one or more of the compounds of this invention. LC compositions of this invention include those that contain 5% or more of one or more of the compounds of this invention. LC compositions of this invention include those that contain 10% or more of one or more of the compounds of this invention. LC compositions of this invention include those that contain 20% or more of one or more of the compounds of this invention. LC compositions of this invention include those that contain 25% or more of one or more of the compounds of this invention. LC compositions of this invention include those that contain 50% or more by weight of one or more of the compounds of this invention.

Compounds of this invention include those of the above Formulas I–V which exhibit a smectic C phase that extends over a temperature range of at least 30° C., as well as those which exhibit a smectic C phase that extends over a temperature range of at least 50° C. In preferred compositions, the temperature range of the smectic C phase includes room temperature (about 20° C.). LC compositions of this invention include those of the above formula which exhibit both a smectic C phase and a smectic A phase. The presence of a smectic A phase in combination with a smectic C phase in an FLC composition facilitates alignment of the composition in an LC cell resulting in fewer layer defects and higher contrast devices. The presence of a nematic phase in addition to a smectic A and smectic C phase further facilitates alignment of the composition in an LC cell resulting in fewer layer defects and higher contrast devices. Compounds of this invention include those of the above formulas that do not themselves exhibit any liquid crystal phase, but which in combination with one or more LC compounds, including one or more LC compounds of this invention, exhibit liquid crystal phases, particularly smectic LC phases.

LC compositions of this invention include those that consist essentially of two or more of the compounds of this invention. LC compositions of this invention include those that are ferroelectric liquid crystal compositions, particularly those that exhibit smectic phases, and more particularly those that exhibit a smectic A phase and/or a smectic C phase. LC compositions of this invention include those comprising one or more compounds of this invention and which are chiral nonracemic. LC compositions of this invention include those comprising one or more compounds of this invention and which are chiral racemic or achiral.

The invention includes FLC host mixtures that comprise one or more achiral or chiral racemic compounds of this invention, FLC host mixtures that consist essentially of one or more achiral or chiral racemic compounds of this invention and FLC host mixtures that consist of at least two achiral or chiral racemic compounds of this invention.

Addition of one or more compounds of this invention to mixtures of LC's can result in changes in physical or optical properties of those mixtures that make the resulting mixtures improved for applications in optical devices. In particular, the addition of one or more of the compounds of this invention can broaden the smectic C range of a given mixture. The addition of one or more of the compounds of this invention can improve alignment of a given LC or FLC mixture in a cell, leading to improved contrast in the optical device employing the LC or FLC cell. The addition of one or more compounds of this invention to an LC composition can result in a decrease in viscosity and response time. Of particular benefit, the compounds of this invention are compatible with (i.e., do not significantly detrimentally affect the properties of) LC and FLC materials that exhibit true bookshelf alignment. LC compounds exhibiting true bookshelf alignment are described for example in pending U.S. application Ser. Nos. 60/229,892, filed Sep. 1, 2000 and 09/653,437 filed Sep. 1, 2000, which are incorporated by reference herein to provide examples of LC compounds which may be combined with the compounds of this invention to provide useful LC and FLC compositions. U.S. provisional application Nos. 60/256,063 and 60/255,984, filed Dec. 15, 2000 also provide examples of LC compounds that may be combined with the compounds of the present invention to provide useful LC and FLC compositions. U.S. regular application Ser. Nos. 09/754,033 and 09/754,034 (commonly owned and concurrently filed with this application) and which take priority from the provisional applications filed Dec. 15, 2000 also provide examples of LC compounds that may be combined with the compounds of the present invention to provide useful LC and FLC compositions.

LC and FLC compositions of this invention are useful in the preparation of optical devices, particularly for optical switching devices and displays. Those of ordinary skill in the art understand how to make LC and FLC cells and devices that utilize the compositions of this invention. In particular, methods and techniques are known and available in the art for alignment of LC and FLC compositions between substrate layers to form optical elements that exhibit true bistable, near bistable, or tristable state switching or optical elements that exhibit analog behavior. Various methods and techniques for constructing LC and FLC cells and for use of such cells are known in the art and can be readily adapted for use with compositions of this invention. The compositions of this invention are particularly well suited for providing devices that can operate (in a smectic C phase, for example) over a broad temperature range.

DETAILED DESCRIPTION OF THE INVENTION

The invention relates generally to compounds that are useful as components in LC compositions. LC compositions typically contain a plurality of components, some of which exhibit LC phases, which when combined exhibit LC phases. LC compositions of most interest are those which exhibit a desired LC phase over a temperature range that facilitates practical application of the composition in an optical device. For example, LC materials exhibiting a smectic C range around normal room temperature can be employed in device applications. Preferred LC materials will exhibit the desired LC phase over a broad, useful temperature range which facilitates device stability. Preferred LC materials will exhibit a desired LC phase with temperature range that minimizes or avoids crystallization of components of the LC composition during operation or storage of an optical device. Compounds of this invention can improve (broaden or shift) the temperature range of desired LC phases in LC compositions to which they care added. In particular, compounds of this invention can be employed to broaden or shift the temperature range of smectic C phases of LC compositions. Compounds of this invention can also result in the introduction of beneficial phases, e.g., smectic A phases in combination with smectic C phases.

The compounds may also be added to lower the temperature at which crystallization of an LC composition occurs to improve storage lifetime of an LC device containing the LC composition. Benefit is assessed as lowering of the melting point of the compositions and/or as lowering of the freezing point of the mixture. A significant improvement in LC stability can be obtained with even a 2° C. lowering of melting point, if that lowering is obtained without a significant negative effect on other LC properties. LC compositions of this invention include those in which the melting point of the LC composition is decreased by at least 4 or 5° C. by addition of one or more compounds of this invention without significant detrimental effect on other LC phase properties. In some compositions addition of 10 weight % of or less of one or more compounds of this invention can achieve a lowering of 4 or 5° C. Significant improvements in LC stability can be achieved by lowering the freezing point of a mixture. LC compositions of this invention include those in which the freezing point of the LC composition is decreased by at least 5° C. or by at least 10° C. without significant detrimental effect on other LC phase properties by addition of one or more compounds of this invention. Again in some compositions, an addition of 10 weight % of one or more compounds of this invention can achieve a lowering of the freezing point by 5° C. or 10° C. LC compositions comprising one or more of the compounds of this invention and exhibiting a freezing point of –60° C. or lower are of particular interest. Those compositions which exhibit a FP of –60° C. or lower and contain 10% by weight or less of a compound of this invention are particularly useful. LC compositions often exhibit a freezing point significantly lower than the melting point, indicative of supercooling. Preferred LC mixtures of this invention exhibit a freezing point that is significantly lower than the melting point of this invention. LC compositions of this invention include those in which the difference in the melting point and freezing point, i.e., |MP-FP| (absolute value of the difference of the MP and FP) of the composition is increased by 10° C. without significant detrimental effect on other LC phase properties by addition or one or more compounds of this invention. In some cases, an addition of 10 weight % of one or more compounds of this invention can result in a significant differential lowering, approaching 10° C., of FP compared to MP of a mixture.

Compounds of this invention can impart additional beneficial optical or physical properties to LC compositions to which they are added. Properties that can be affected include: viscosity (decreased viscosity results in faster optical switching), tilt angle, birefringence, LC layer structure (the ability of the LC to form a desired layer structure, e.g., to form a true bookshelf structure), and alignment of layers between substrates (the ability of the LC to be aligned with minimal defects which are detrimental to device contrast). Preferred LC compositions of this invention include those in which addition of one or more compounds of this invention (Formulas I–V) results in a significant improvement of 10% or more in a physical or optical property of the mixture to which they are added.

As used herein the term alkyl refers generally to straight-chain and branched alkyl groups. Alkyl groups can include lower alkyl groups (those having from 1–6 carbon atoms) and higher alkyl groups (those having about 7 or more carbon atoms), unless otherwise noted. The term alkoxy group refers to groups having a terminal oxygen atom (—O-alkyl). For example, alkoxy tail groups are attached to the core via the terminal oxygen. The alkyl portion of an alkoxy group includes straight-chain and branched alkyl groups and unless otherwise noted includes lower alkyl and higher alkyl groups. Alkyl groups, including those of alkoxy group, typically have less than 20 carbons and preferably, dependent upon the specific structure, have 12 or fewer carbon atoms. In compounds where alkyl or alkoxy tail groups are specified, preferred alkyl groups have from 5 to 12 carbon atoms and more preferred alkyl groups have 6 to 10 carbon atoms.

As used herein the term alkene refers generally to any group containing one or more double bonds. The alkene tails of this invention as specified in Formulas I–V contain a single double bond. Alkene tails include alkanes tails, i.e., —O-alkene, in which the alkene group has a terminal oxygen atom which forms the bond to the core. In general the double bond of the alkene tail can be positioned anywhere in the chain, but preferably is located 2 or more carbons from the end of the tail attached to the core. The alkene may contain an omega double bond, but the double bond is more preferably located away from the ends of the tail. The double bond may be in the cis or trans configuration.

The term alicyclic generally refers to alkyl or alkene groups that contain a cyclic portion. An alicyclic group can be a saturated ring or unsaturated ring, such as a cyclohexane or cyclohexene ring. Alicyclic rings can contain one or more (typically one) heteroatoms, e.g., O, N or S, in place of ring $CH_2$ groups. Further, one or more (typically one) ring $CH_2$ groups can be replaced with C=O groups. Alicyclic groups of the cores of this invention are optionally substituted (unless otherwise noted). Preferred substituents include lower alkyl groups, lower alkene groups, halogens, CN and $NO_2$ groups. Preferred halogen substituents are fluorines. In general, all, but two aromatic ring positions (e.g., the positions for linkages to tails or to other core rings) can carry non-hydrogen substituents. However, more typically one or two ring positions (in addition to the linkages to the tails or other cores) can be substituted.

The term aromatic generally refers to a group containing at least one aromatic ring, e.g., a phenyl ring. Aromatic rings typically are have five or six-member aromatic rings. Aromatic rings can also include fused aromatic rings, such as naphthalene or dehydronaphthalene rings (see Scheme 1). An aromatic ring can contain one or more (typically one or two) heteroatoms, e.g., O, N or S. Aromatic groups of the cores of this invention are optionally substituted (unless otherwise noted). Preferred substituents include lower alkyl groups, lower alkene groups, halogens, CN and $NO_2$ groups. Preferred halogen substituents are fluorines. In general, all, but two positions on the ring can be substituted (e.g., the positions for linkages to tails or to other core rings). However, typically one to four positions of the ring can be substituted and more typically one or two ring positions (in addition to the linkages to the tails or other cores) can be substituted. Preferred substituted aromatic rings have one position substituted with a lower alkyl or alkene group, a CN group or a $NO_2$ group. Additionally preferred substituted aromatic rings have one or two positions substituted with one or two halogens, and the preferred halogen is fluorine.

Specific examples of compounds of this invention are provided in Schemes 1–3 and in the Examples. Compounds illustrated in Scheme 3 are chiral nonracemic compounds.

Exemplary methods for synthesizing the compounds of this invention are provided in the Examples. Compounds of this invention can be readily synthesized by methods that are well-known in the art, particularly in view of the guidance provided herein.

Results obtained from a comparison of two mixtures MX 9132X (containing 10% by weight of compound 1566) and MX 9133X (containing 10% by weight of compound 1568) are provided in Table 1, where the structures of the mixture components are also provided. These results demonstrate a decrease in viscosity and response time in a test mixture in which a silane component with an alkyl tail is replaced with one having a perfluoroalkyl terminal tail portion.

Exemplary LC mixtures comprising one or more compounds of this invention are provided in Tables 3–20 and 22–23. Tables 2 and 21 provide the phase diagrams, and various properties of the mixtures. The components and amounts of components (weight %) of the mixtures of Table 2 are provided therein. Table 2 also lists the properties of mixtures that are prepared using compounds of concurrently filed U.S. application Ser. Nos. 09/754,034 and 09/754,033, which are incorporated by reference herein in their entirety. The listing of mixture components provided in Tables 3–20 and 22–23, and in Scheme 5, include a number of LC compositions components that can be combined with one or more of the compounds of this invention (alone or in combination with components of U.S. application Ser. Nos. 09/754,034 and 09/754,033). Properties of polarization, viscosity, electric rise time, resistivity, dielectric constant of the mixtures are given when available. Tables 2 and 21 also provide the melting point (MP) and freezing point (FP) as measured by differential scanning calorimetry. The lower temperature limit on the instrument used to provide FP measurements of Table 1 is −60° C., so table entries of FP of −60° C. indicate that the FP was less than or equal to −60° C. The properties listed in Table 1 are measured using techniques that are well-known in the art. In the tables, I means "isotropic", N means nematic, A means smectic A, C means smectic C, SI means smectic I and Sx (or S?) means unidentified smectic phase.

Chiral nonracemic LC mixtures for which data is provided in Table include those comprising a compound of this invention in amounts ranging from about 3% by weight to about 10% by weight of the mixtures. In specific embodiments, the invention provides mixtures which contain compounds of this invention in combination with disilane compounds of U.S. patent application Ser. No. 09/754,033.

Table 21 provides the results of additional comparisons of properties of mixtures with and without addition of an alkene of this invention. MX 9244 is a mixture containing 3 weight % of MDW 1592 and 1632 (Scheme 5) in base mixture 9531 (composition given in Table 22). MX 9368 is a mixture of 10 weight % MDW 1669 (Scheme 5) in base mixture 9532. MX 9244 exhibits a significant lowering of melting point (about 4° C.) compared to the base mixture (containing no alkene of this invention). Note that the other LC properties of the mixture are not significantly effected by the addition of MDX 1592 and 1632. Optical and switching properties of MX 9244 have not been optimized. MX 9368 exhibits a significant lowering of freezing point along with a significant decrease in MP compared to the base mixture. Further, MX 9368 exhibits a smectic A phase in addition to the smectic C phase. Note that the other LC properties of the mixture are not significantly effected by the addition of MDX 1669. Optical and switching properties of MX 9368 have not been optimized.

U.S. application Ser. Nos. 60/229,892, filed Sep. 1, 2000 and 09/653,437 filed Sep. 1, 2000, which are incorporated by reference herein to provide examples of LC compounds which may be combined with the compounds of this invention to provide useful LC and FLCS compositions. U.S. provisional application Nos. 60/255,984 and 60/256,063, filed Dec. 15, 2000, also provide examples of LC compounds that maybe combined with the compounds of the present invention to provide useful LC and FLCS compositions. U.S. applications filed concurrently herewith as U.S. patent application Ser. Nos. 09/754,034 and 09/754,033 provide examples of chiral nonracemic, chiral racemic and achiral components that can be combined with one or more compounds of this invention to provide useful LC and FLC compositions. This invention includes LC compositions that combine one or more of the compounds of this invention with one or more compounds of the compounds of U.S. patent application Ser. No. 09/754,034, those that combined one or more of the compounds of this invention with one or more of the compounds of U.S. patent application Ser. No. 09/754,033; and those that combine one or more of the compounds of U.S. patent application Ser. No. 09/754,034, one or more of the compounds of U.S. patent application Ser. No. 09/754,033 and one or more of the compounds of this invention.

Scheme 6 provides exemplary components (1–20) that can be combined with one or more of the compounds of this invention to obtain useful LC and FLC compositions. Structures 9–13 illustrate components, including achiral or chiral racemic components, which can be combined with one or more of the compounds of this invention to obtain a LC mixture, particularly mixtures that exhibit smectic phases, and more particularly mixtures that exhibit smectic C phases and optionally smectic A phases. In such mixtures one or more of the alkenes of this invention is combined with one or more of the compounds of structures 9–13. LC mixtures of this invention include those which combine one or more alkenes of this invention with one or more phenylpyrimidines of structure 9, and in particular include those which contain a total of about 2 to about 25 weight % of one or more compounds of this invention and a total of about 10–80 weight % of one or more compound of structure 9. LC mixtures of this invention also include those which combine one or more alkenes of this invention with one or more compounds of structures 11 and 12, and in particular include those which contain a total of about 2 to about 25 weight % of one or more compounds of this invention and a total of about 10 to about 40 weight % of one or more compounds of structures 11 and 12. LC mixtures of this invention also include those which combine one or more alkenes of this invention with one or more compounds of structure 10 and in particular include those which contain a total of about 2 to about 25 weight % of one or more compounds of this invention and a total of about 5 to about 50 weight % of one or more compounds of structure 10. Of particular interest are mixtures which contain at least three terphenyl compounds each of which is substituted with two fluorines on a different ring of the core. The use of such terphenyl compounds in LC compositions is described in U.S. Pat. No. 5,278,680, which is incorporated by reference herein. LC mixtures of this invention can further contain one or more compounds of structure 13, and in particular can contain from about 5 to about 15 weight % of one or more compounds of structure 13. LC mixtures of this invention can combine components of structure 9, components of structures 11 or 12, components of structure 10 and optionally components of structure 13 with one or more alkenes of this invention.

Structures 17–20 (in Scheme 6) illustrate exemplary chiral non-racemic components that can be employed to prepare chiral nonracemic LC mixtures, particularly those chiral nonracemic LC mixtures that exhibit smectic phases. Chiral nonracemic enantiomers of the compounds of structures 17–20 can also be employed in the mixtures of this invention. LC compositions of this invention include those which contain one or more of the alkene compounds of this invention in combination with up to a total of about 25% by weight of one or more of compounds 17–20 of Scheme 6. LC compositions further include those which combine one or more compounds of structure 9, one or more compounds of structure 10, or one or more compounds of structures 11 or 12 with one or more alkene compounds of this invention and one or more of the chiral nonracemic compounds of structures 17–20. Chiral nonracemic compounds of this invention can also include one or more compounds of structure 13 and those of structures 14–16.

Compounds of structures 1–20 can be prepared by methods that are well known in the art from readily available starting materials. Methods that are useful in the preparation of various LC compounds and FLC compounds are provided, for example in U.S. Pat. Nos.: 5,051,506; 5,061,814; 5,130,048; 5,167,855; 5,178,791; 5,178,793; 5,180,520; 5,271,864; 5,278,680; 5,380,460; 5,422,037; 5,453,218; 5,457,235; 5,539,555; 5,543,078; 5,585,036; 5,626,792; 5,637,256; 5,658,493; 5,753,139; 5,866,036; and 6,139,771. Each of which is incorporated by reference herein for synthetic methods applicable to the synthesis of compounds of this invention including compounds of structures 1–20. The listed patents along with U.S. Pat. Nos. 5,168,381 and 5,596,434 also provide detail of how LC and FLC compositions of this invention can be applied for the production of LC cells and optical devices.

LC and FLCS compositions of this invention are useful in the preparation of optical devices, particularly for optical switching devices and displays. Of particular interest are SSFLC devices for use for rapid optical switching as in display applications. Those of ordinary skill in the art understand how to make LC and FLCS cells and devices that utilize the compositions of this invention. Various methods and techniques for constructing LC and FLCS cells and for use of such cells are known in the art and can be readily adapted for use with compositions of this invention. The compositions of this invention are particularly well suited for providing devices that can operate (in a smectic C phase, for example) over a broad temperature range.

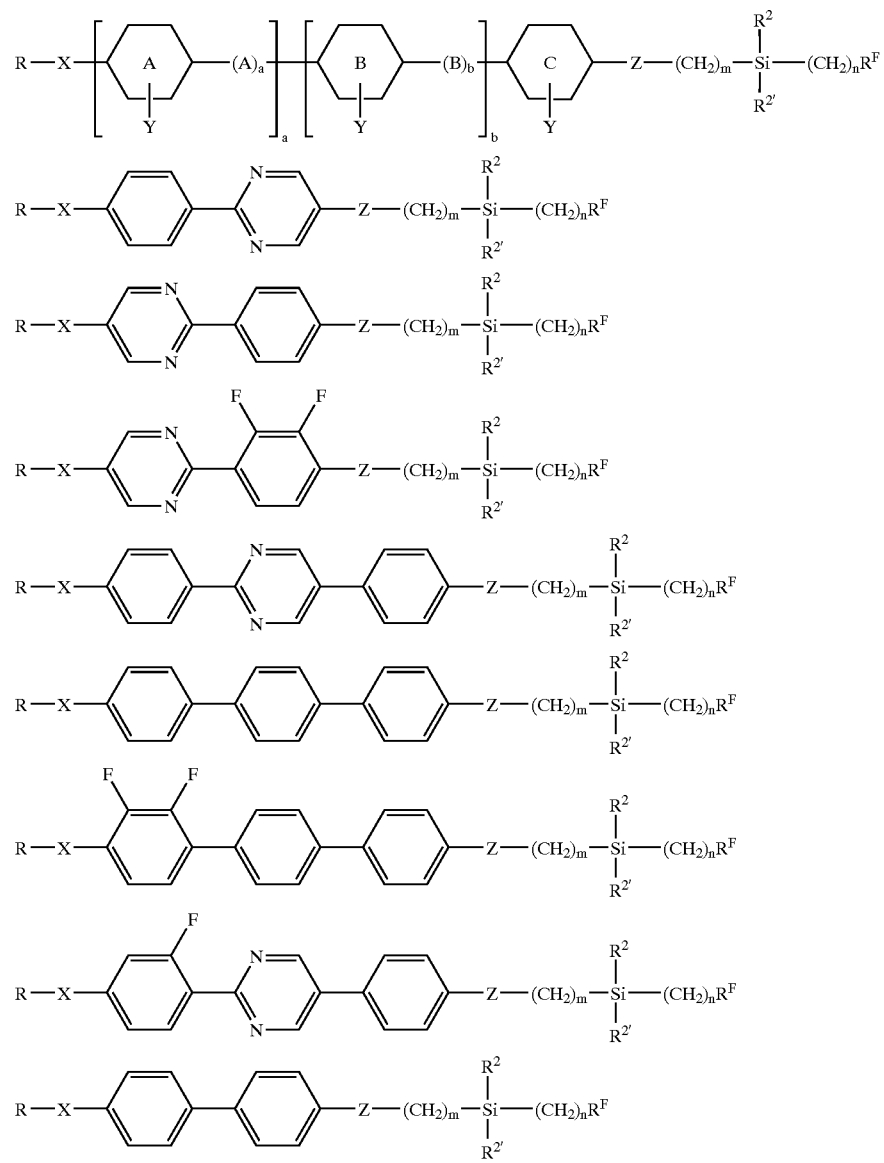

Scheme 1

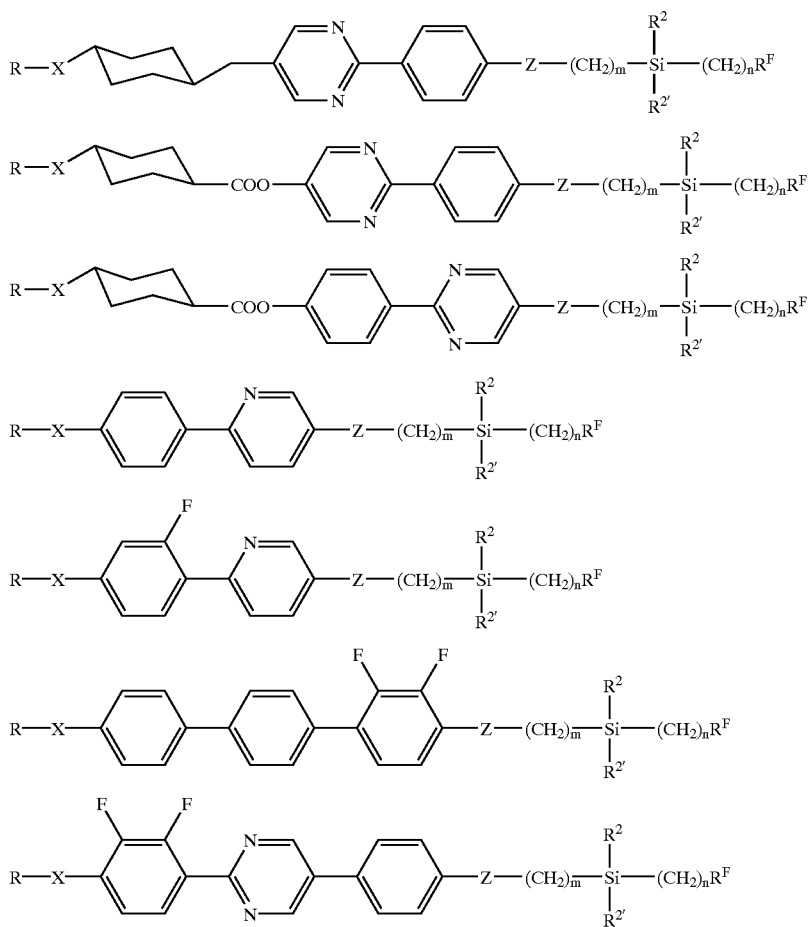
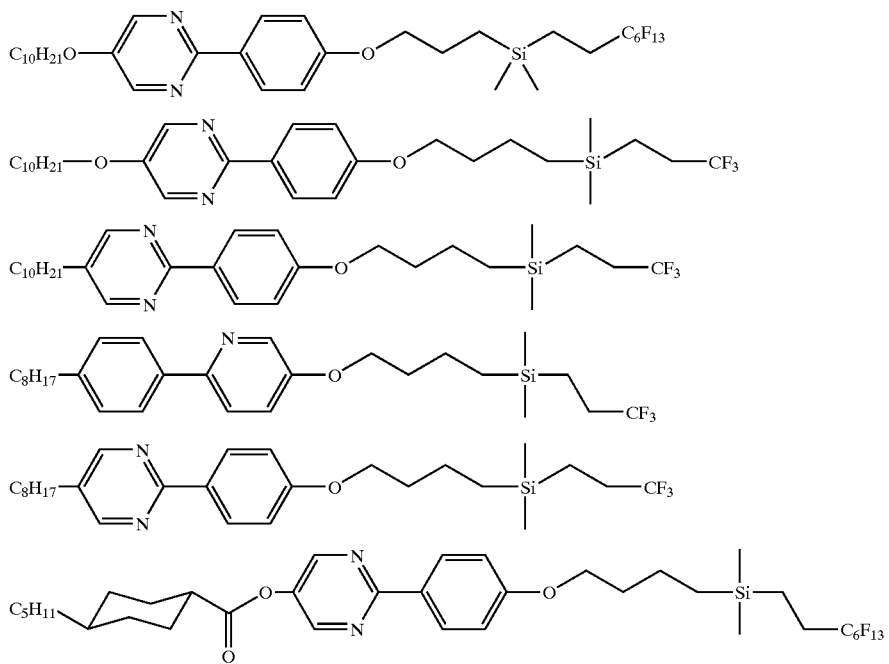
Scheme 2

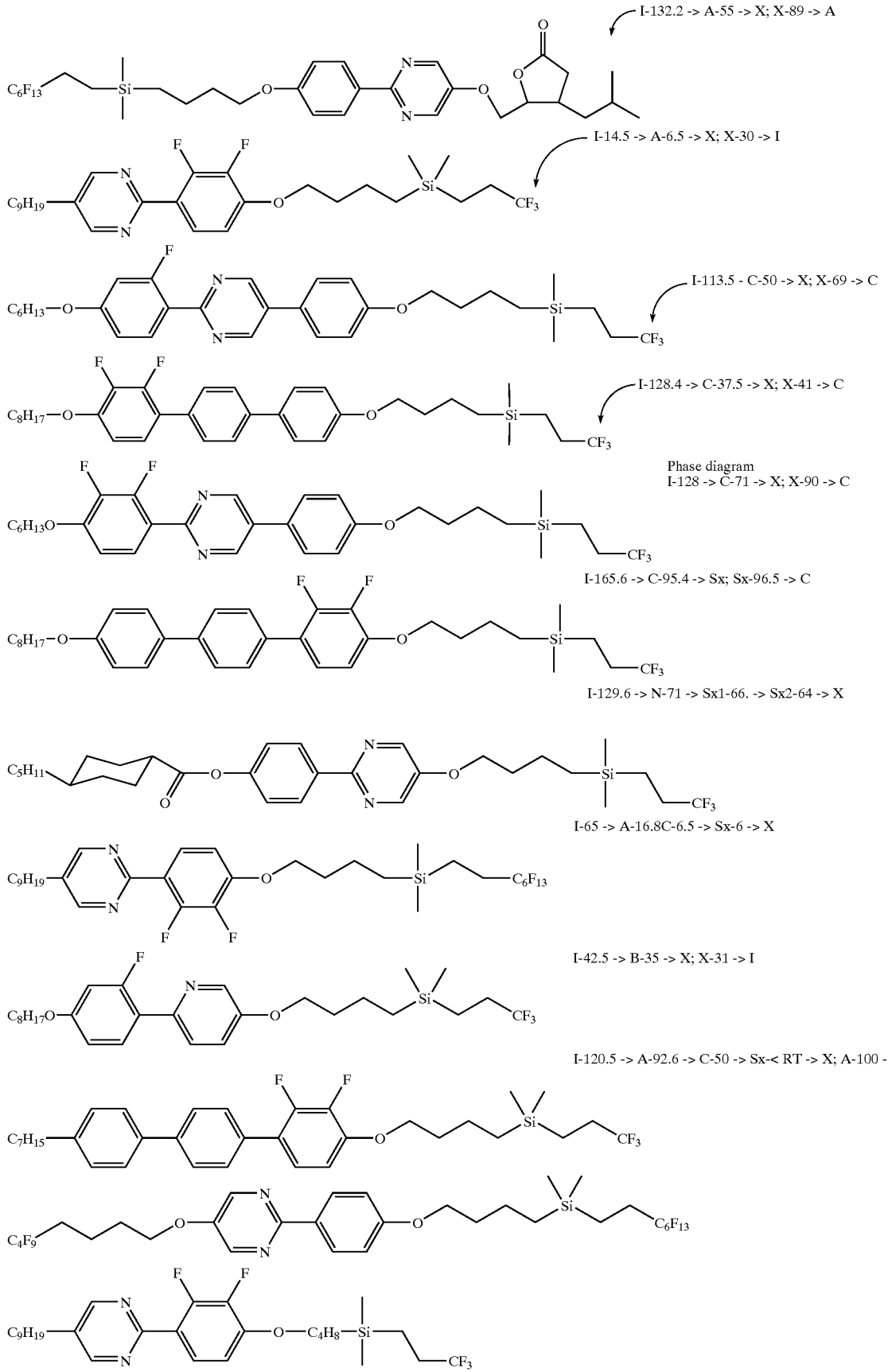

-continued
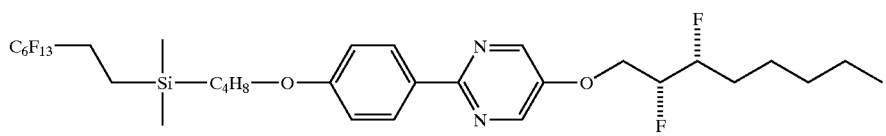
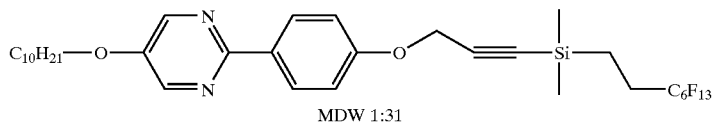
MDW 1:31
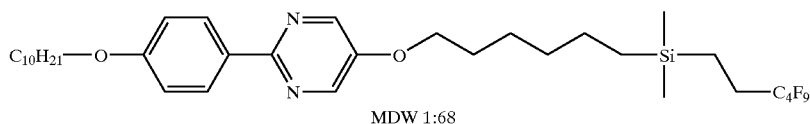
MDW 1:68
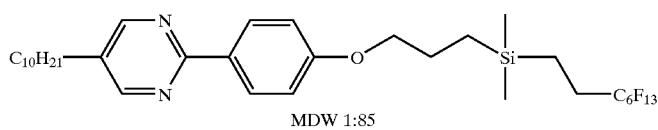
MDW 1:85
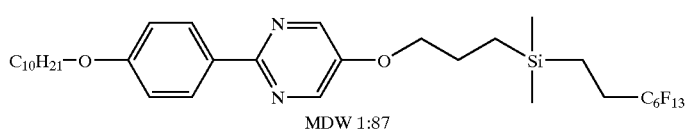
MDW 1:87
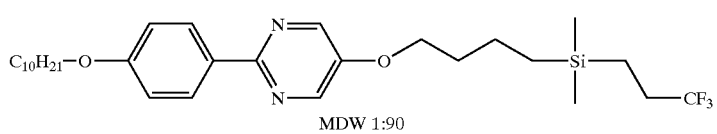
MDW 1:90
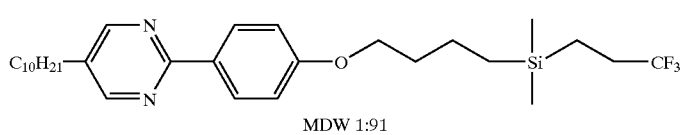
MDW 1:91
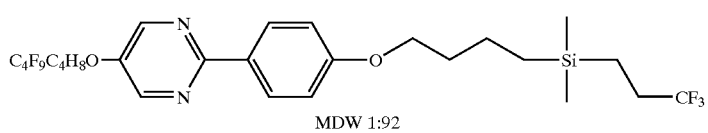
MDW 1:92
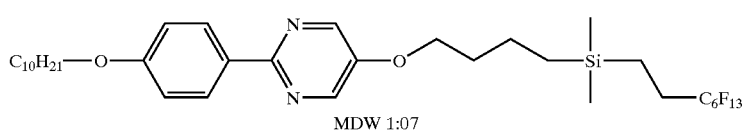
MDW 1:07
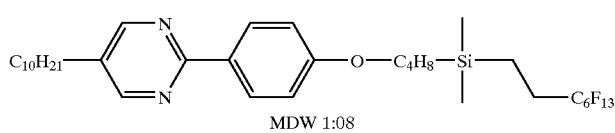
MDW 1:08
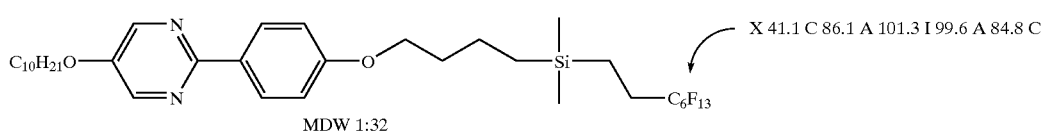
MDW 1:32
X 41.1 C 86.1 A 101.3 I 99.6 A 84.8 C
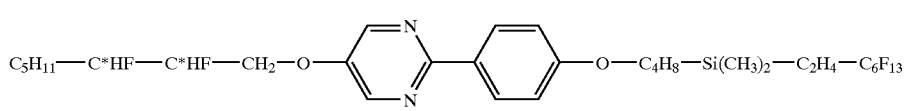
and enatiomers thereof SCHEME 3
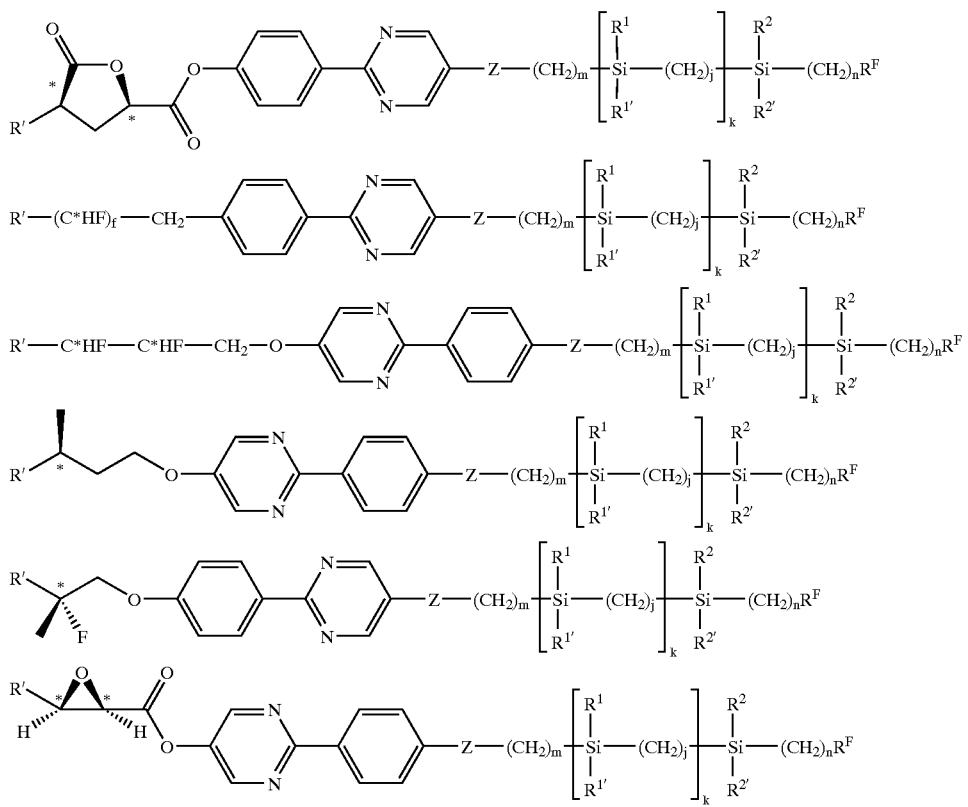
where * indicates an asymmetric carbon, R' is an alkyl, alkenyl or ether group, f is 1, 2, or 3 and other variables are defined in the text.
SCHEME 4
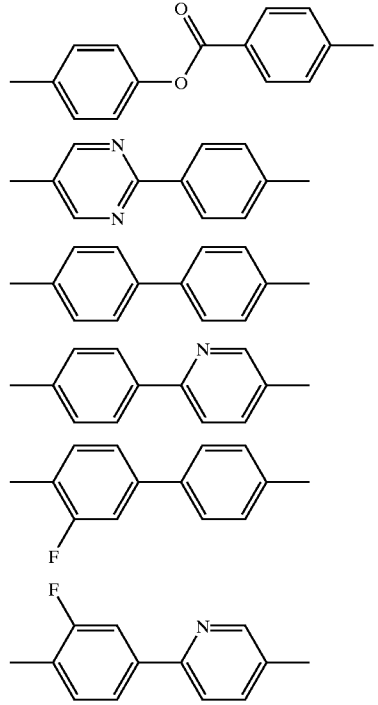
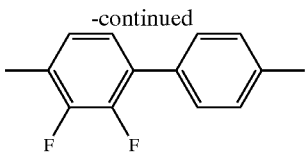
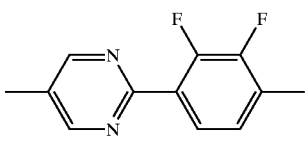
-continued
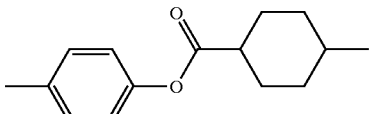
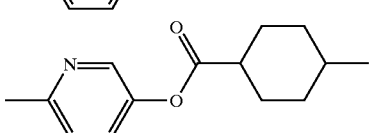
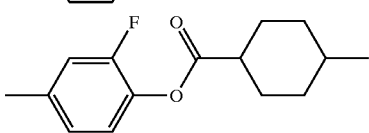

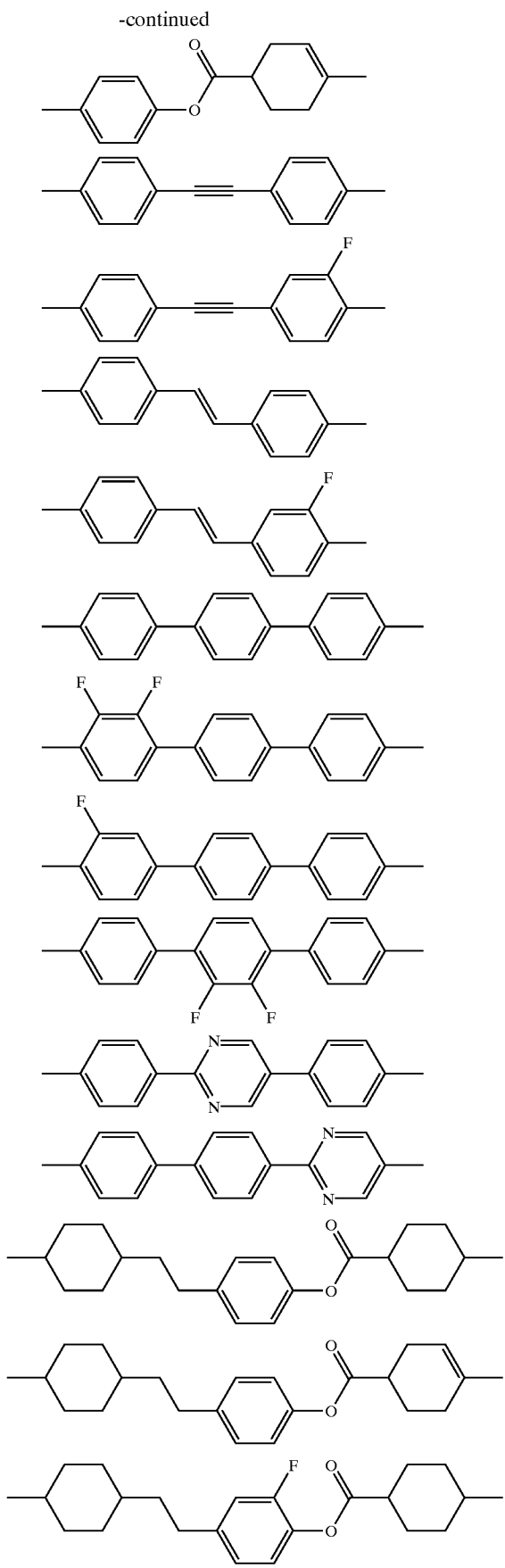
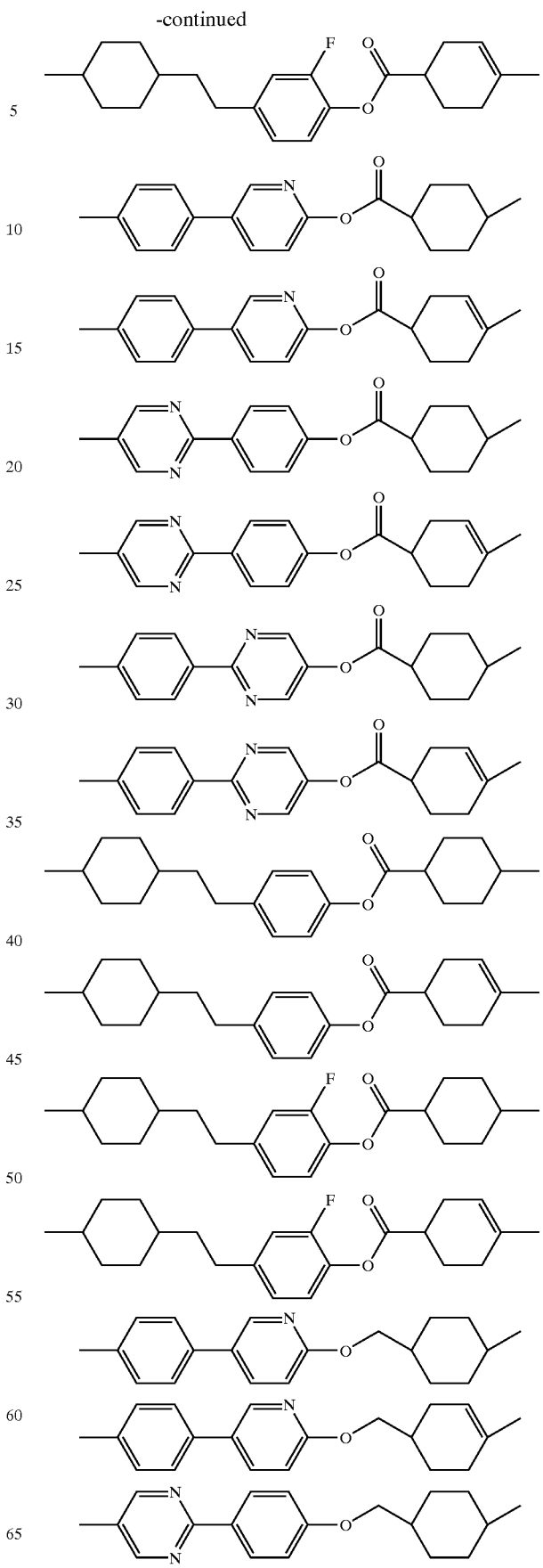

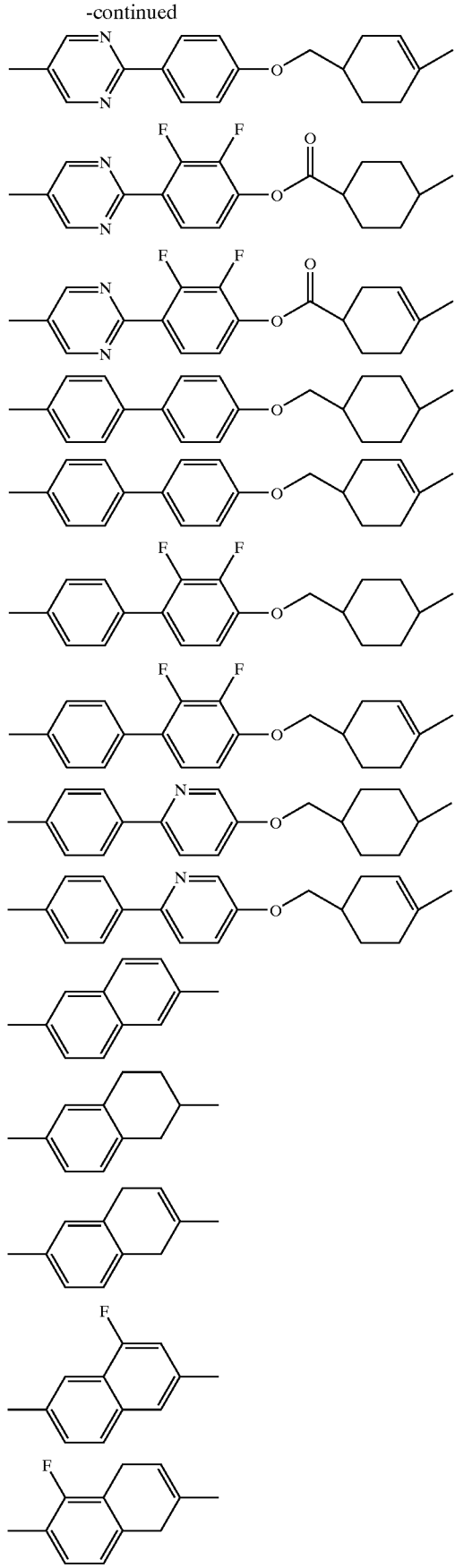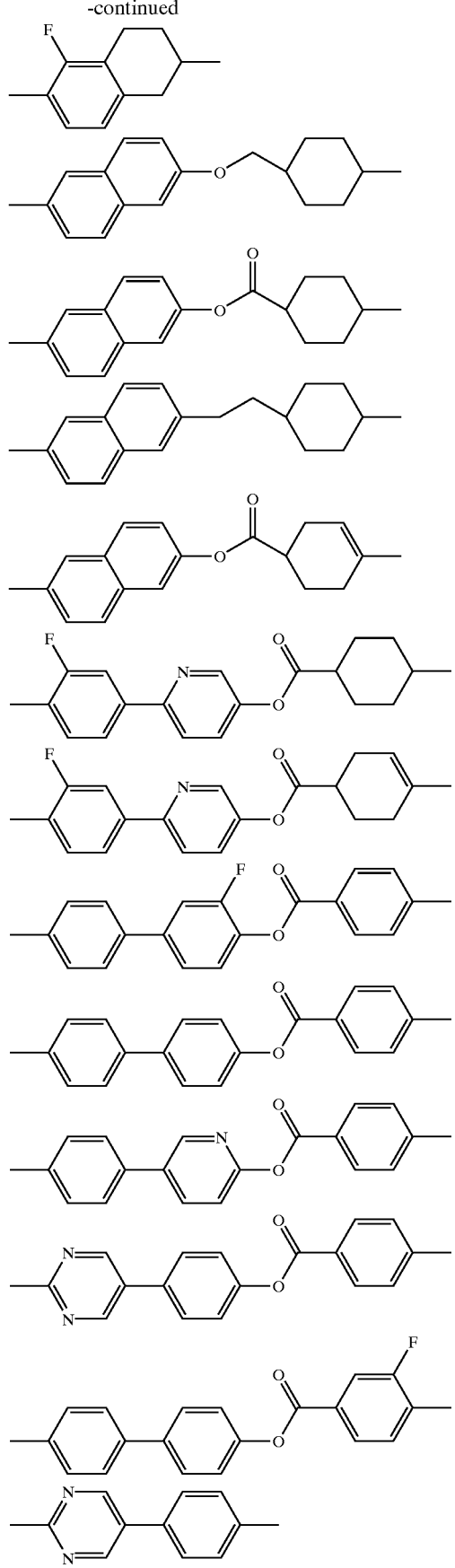

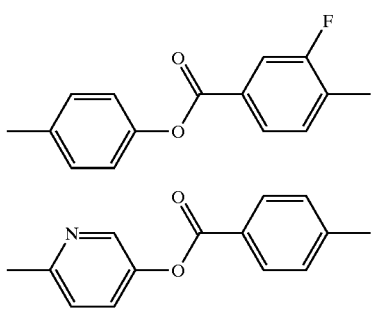
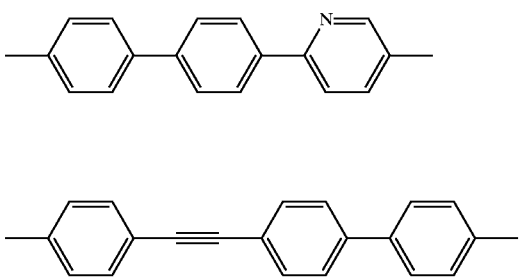
| SCHEME 5 | | |
|---|---|---|
| MDW # | Structure | Phase Diagram |
| 950 | | X <-90 - I<br>- 94-> |
| 987 | | X <----21 ----- SmC* <-54- SmA <-63-I<br>-53-> S? -57-> |
| 644 | | X <-20- N <-41 - I<br>-43-> - 47-> |
| 699 | | |
| 139 | | X - 75-> I<br><-86- |
| 337 | | X <-100- C <-105- N <-169- I |
| 1135 | | X <-73.5 -S?<-85- C <-104- A<-175- N<br><-186- I |
| 1638 | | |

-continued
SCHEME 5
| MDW # | Structure | Phase Diagram |
|---|---|---|
| 1458 | 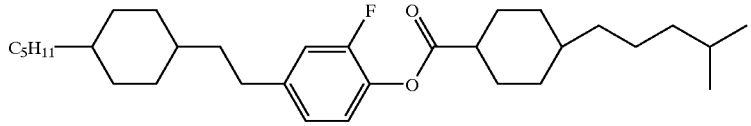 | |
| 1671 | 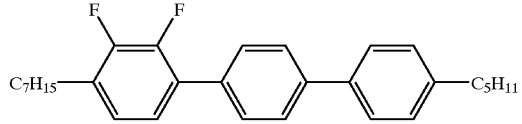 | X -56-> C -106-> A -131-> N -136-> I |
| 1673 | 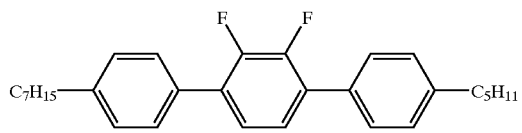 | X -37-> N -112-> I<br>X <-24- C |
| 1674 | 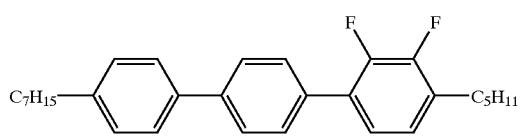 | X -66-> SI -75->C -119-> A -135->N-137-> I |
| 31 | 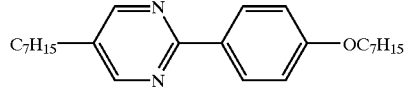 | |
| 3 | 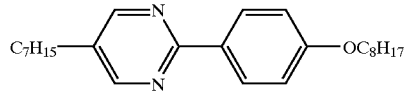 | X -49-> A -44->N -69.5-> I |
| 1695 | 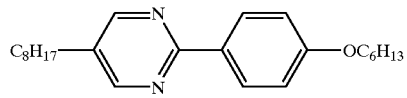 | |
| 5 | 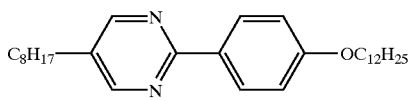 | X -43.2->C -62.4->A -66.8-> N -68.2-> I |
| 4 | 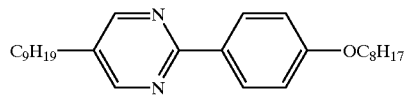 | X -33-> C -60-> A -74.5-> I |
| 913 | 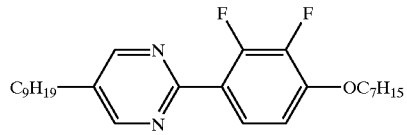 | X -43->C -50-> I<br><-44- <-52- |
| 911 | 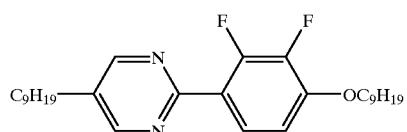 | X -44->C -52-> I<br><-37- <-52- |
| 374 | 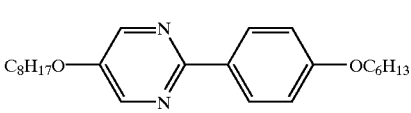 | |

-continued

SCHEME 5

| MDW # | Structure | Phase Diagram |
|---|---|---|
| 1054 | 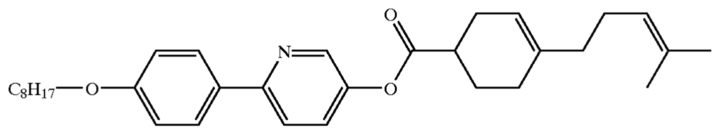 | X <----- C <-135- N<-150- I -55-> Sx -82-> |
| 942 | 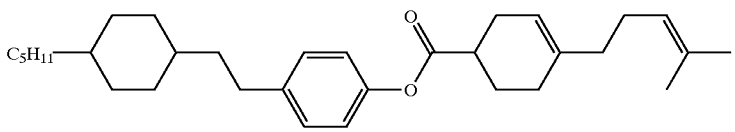 | |
| 576 | 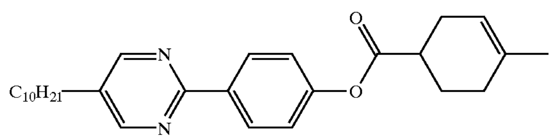 | X <-35- S? <-45 - C <-68- N<-107- I -50-> -54-> |
| 1059 | 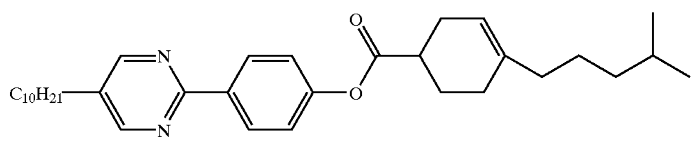 | |
| 336 | 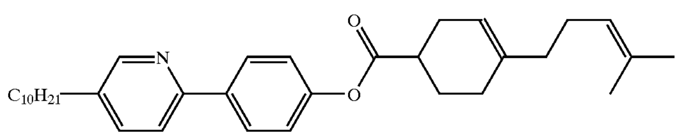 | X <-27- C <-83- N<-106- I -40-> |
| 577 | 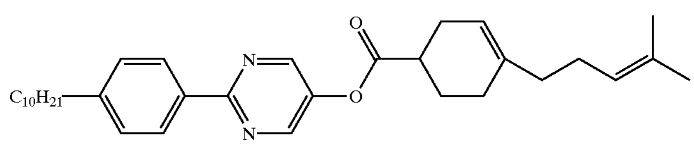 | |
| 1701 | 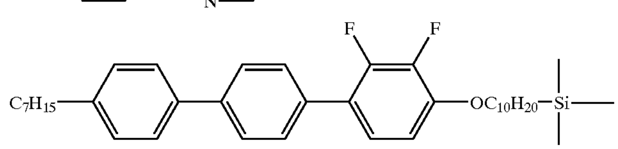 | |
| 1669 | 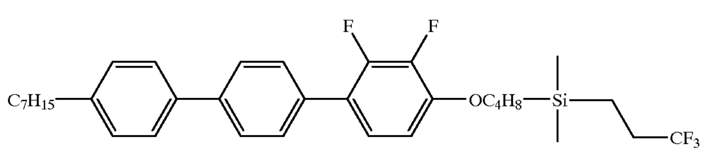 | |
| 1658 | 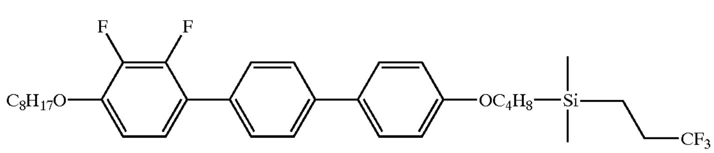 | |
| 1592 | 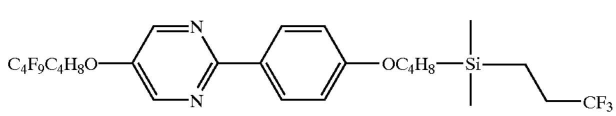 | |

-continued

SCHEME 5

| MDW # | Structure | Phase Diagram | | | | | |
|---|---|---|---|---|---|---|---|
| 1532 | C₁₀H₂₁O-pyrimidine-C₆H₄-OC₄H₈-Si(Me)₂-CH₂CH₂-CF₃ | | | | | | |
| 1632 | C₁₀H₂₁O-pyrimidine-C₆H₄-OC₄H₈-Si(Me)₂-CH₂CH₂-C₆F₁₃ | | | | | | |
| 1586 | C₄F₉C₄H₈-O-pyrimidine-C₆H₄-OC₈H₁₆-Si(Me)₂-CH₂-Si(Me)₃ | | | | | | |
| 1709 | C₄F₉C₅H₁₀-pyrimidine-C₆H₄-OC₁₀H₂₀-Si(Me)₃ | | | | | | |
| 1597 | C₄F₉C₄H₈O-pyrimidine-C₆H₄-O-(CH₂)₄-CH=CH-C₄H₉ | Cr | 64.9 | SmC | 100.4 | SmA | 102.4 I |
| | | | 43.3 | | 99.6 | | 101.0 |
| | C₄F₉C₄H₈O-pyrimidine-C₆H₄-O-CH₂-CH=CH-C₃H₇ | Cr | 61.7 | SmC | 135.0 I | | |
| | | | 57.7 | | 134.6 | | |
| | C₄F₉C₄H₈O-pyrimidine-C₆H₄-O-(CH₂)₄-CH=CH-C₂H₅ | Cr | 70.7 | SmC | 113.8 | SmA | 115.4 I |
| | | | 60.7 | | 113.8 | | 114.6 |
| | C₄F₉C₄H₈O-pyrimidine-C₆H₄-O-CH₂-CH=CH-C₅H₁₁ | Cr | 59.0 | SmC | 114.2 | SmA | 121.0 I |
| 1015 | C₄F₉C₄H₈O-pyrimidine-C₆H₄-O-citronellyl | Cr | 62 | SmA | 67 I | | |
| 1028 | C₄F₉C₄H₈O-pyrimidine-C₆H₄-O-CH₂-cyclohexenyl-prenyl | | | | | | |

Scheme 6

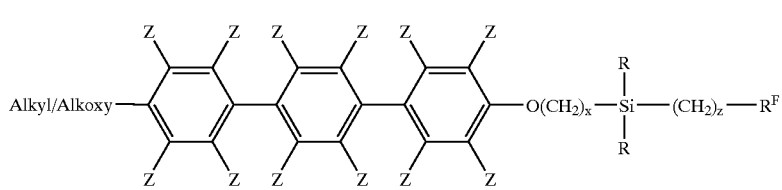

-continued
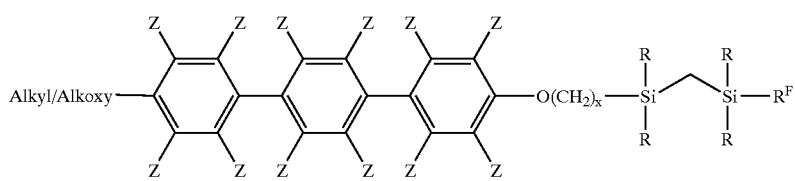
2
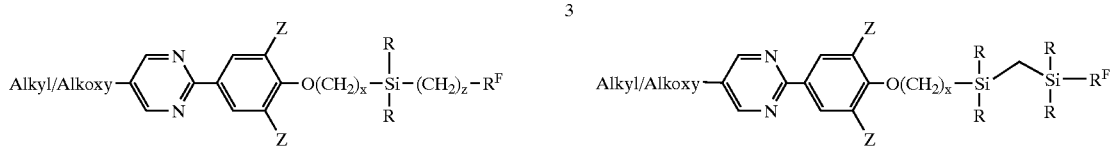
3          4
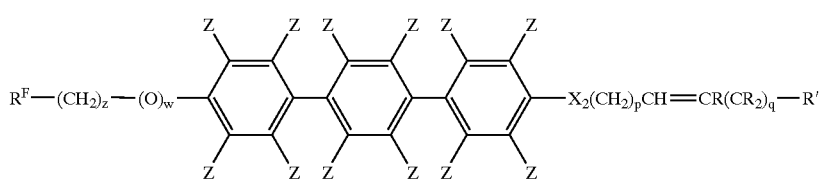
5
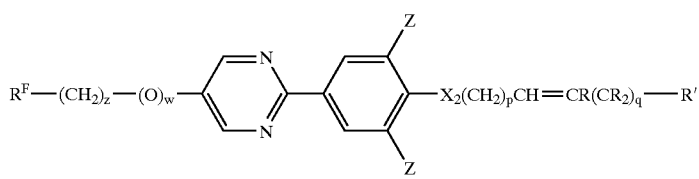
6
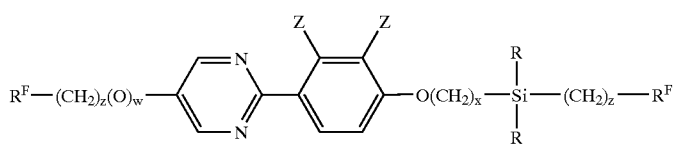
7
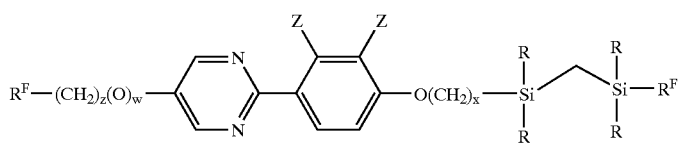
8
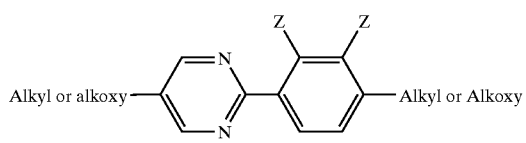
9
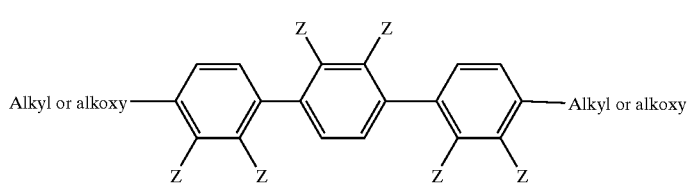
10
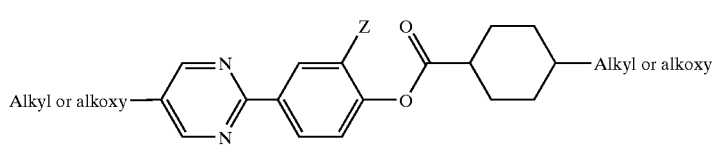
11
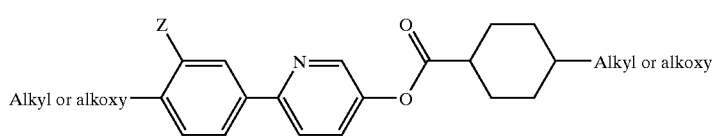
12

-continued

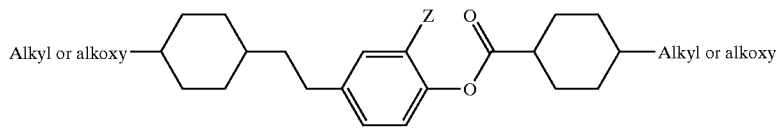
13

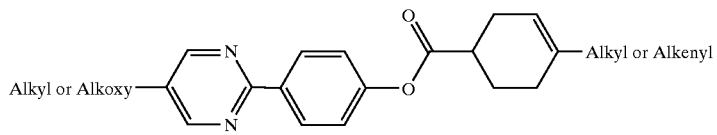
14

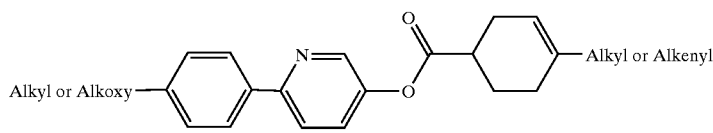
15

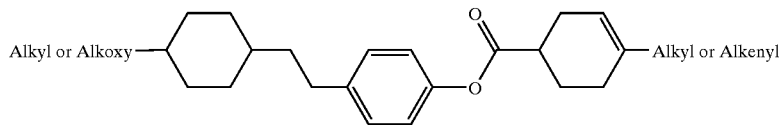
16

17

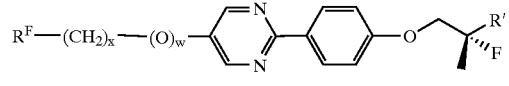
18

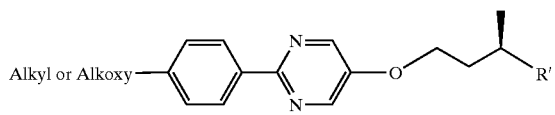
19

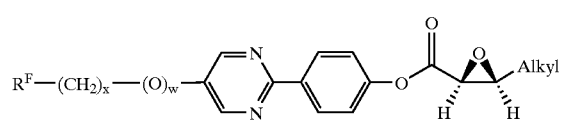
20 wherein p, x and z are integers ranging from 1 to 20, inclusive, q is 0 or an integer ranging from 1 to 20, inclusive; w is 0 or 1; R are alkyl groups, preferably having from 1 to 6 carbon atoms; R' is an alkyl group having from 5 to 20 carbon atoms; $R^F$ is a perfluoroalkyl group; Z is H or a F; and alkyl or alkoxy groups are those that have 1 to 20 carbon atoms.

TABLE 1

|  | Dimethylethylsilane (MX9132X) | Silaneperfluoroalkyl (MX9133X) |
|---|---|---|
| Tilt Angle | 36.5° | 32.5° |
| $P_S$ | 36.9 | 29.0 |
| Viscosity | 580 mP | 352 mP |
| Response Time | 180 μs | 130 μs |

Transition temperatures and mesophase morphology of the mixtures:

| MX9192X | I 75.5 SmC ? Cr |
| MX9133X | I 81.0 SmC |

Composition of the test mixtures:

MX9192X

MDW1566-MDW520: 1:1
MDW950: 10%
MX9193X

MDW1568-MDW520: 1:1
MDW950: 10%

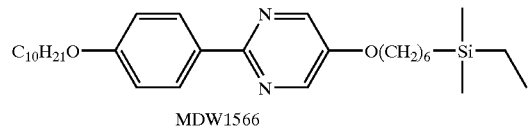
MDW1566

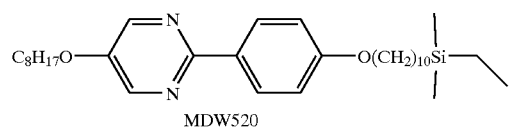
MDW520

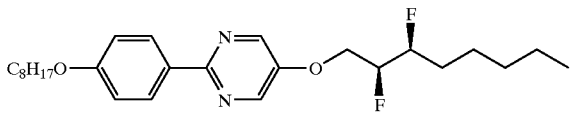
MDW950

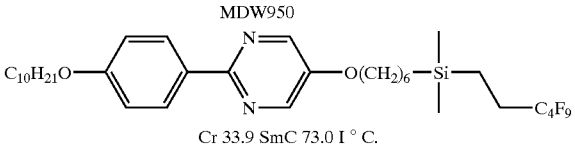
Cr 33.9 SmC 73.0 I ° C.
MDW1568

TABLE 2

| MX # | APT data | | | | | | Phase Info | | |
|---|---|---|---|---|---|---|---|---|---|
| | Ps | Visc | E rise | Resistivity | Dielectric | Applied Field | Phase diagram | DSC MP | DSC FP |
| 9244 | 27.8 | 88.9 | 127 | | | | I - 107.6 - N - 98.6 - A - 86.3 - C | −25.9 | −60 |
| 9272 | 26.6 | 83.6 | 127 | 1.6 e+11 | 4.26 | 6 | I - 102.5 - N - 95.9 - A - 85.7 - C | −38.5 | −43 |
| 9295 | 24 | 73 | 130 | | | | I - 102.2 - N - 96.8 - A - 82.8 - C | −30.5 | <−25 |
| 9338 | | | | | | | | | |
| 9340 | | | | | | | | | |
| 9365 | | | | | | | | | |
| 9368 | | | | | | | I - 113.9 - N - 105.6 - A - 85.1 - C - −10.8 - Sx | −50.9 | −60 |
| 9387 | 36.4 | 171 | 120 | 1.4 e+11 | 4.98 | 6 | I - 99.5 - N - 92 - A - 85 - C - −60 - X | −60 | −60 |
| 9390 | 29.6 | 92.2 | 117 | 2.7 e+11 | 5.16 | 6 | I - 113.8 - N - 111.4 - A - 87.1 - C - 2.1 - Sx | −60 | −60 |
| 9405 | 14.4 | 70.9 | 207 | 3.1 e+11 | 3.92 | 6 | I - 103.8 - N - 100.1 - A - 85.1 - C | −43.1 | −60 |
| 9417 | 19.5 | 80.3 | 162 | 1.4 e+11 | 3.97 | 6 | I - 102.9 - N - 98.0 - A - 92.2 - C - −28.9 - Sx | −34.9 | −60 |
| 9426 | 29.4 | 195.7 | 145 | 9.5 e+10 | 4.37 | 6 | I - 104.2 - N - 102.3 - A - 90.2 - C | −35.7 | −60 |
| 9427 | 35.4 | 96.4 | 115 | 3.6 e+11 | 4.52 | 6 | I - 102.1 - N - 95.8 - A - 90.2 - C | −56.4 | −60 |
| 9431 | 14.2 | 80.3 | 227 | 5 e+11 | 3.98 | 6 | I - 104.4 - N - 96.9 - A - 82.7 - C | −36.3 | −33.8 |
| 9435 | 33.9 | 89.9 | 112 | 1.8 e+11 | 4.66 | 6 | I - 100.0 - N - 94.6 - A - 87.3 - C | −47.4 | −60 |
| 9441 | | | | | | | | | |
| 9451 | 14.7 | 61.2 | 57 | 3.7 E+11 | 3.34 | 6.83 | I - 82.1 - A - 74.6 - C | −16.6 | −23.3 |
| 9452 | | | | | | | I - 82.1 - A - 74.6 - C | −26.4 | −29.2 |
| 9454 | 35.1 | 92.2 | 110 | 3.8 e+11 | 3.88 | 6 | I - 114.0 - N - 93 - A - 90.8 - C | −32.4 | −60 |

TABLE 3

MX 9214

| Component | Percent | Structure | Phase diagram |
|---|---|---|---|
| MDW 950 | 2.00 | 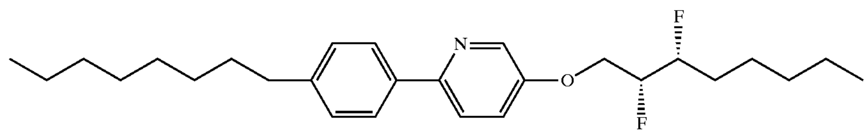 | I-90 –> X; X-94 –> I |
| MDW 987 | 16.00 | 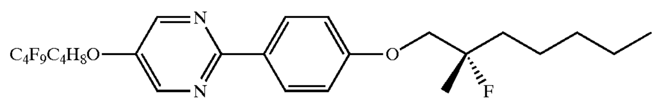 | I-63 –> A-54 –> C*-21 –> X; X-53 –> S?-57 –> C* |
| MDW 1458 | 10.50 | 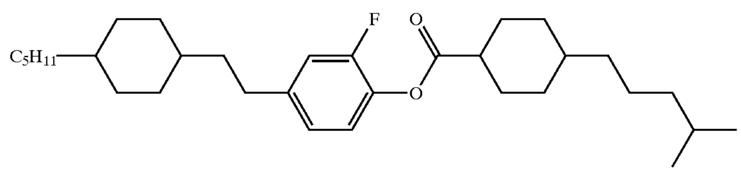 | |
| MDW 913 | 6.00 | 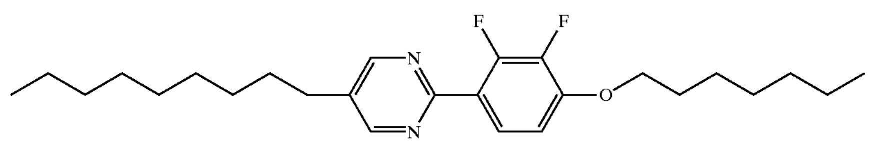 | I-50 –> C-32 –> X; X-43 –> C-50 –> I |
| MDW 911 | 6.00 | 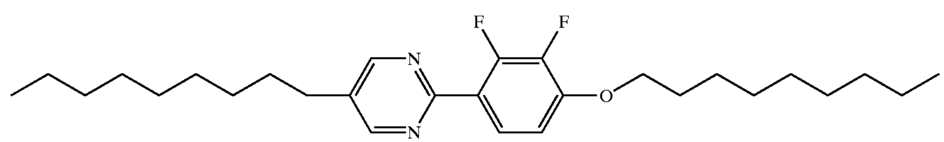 | I-52 –> C-37 –> X; X-44 –> C-52 –> I |
| MDW 374 | 10.00 | 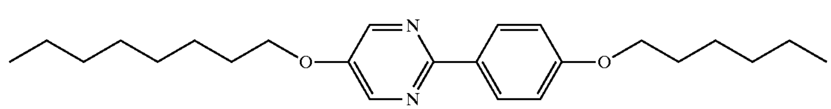 | Q; Q |
| MDW 337 | 18.00 | 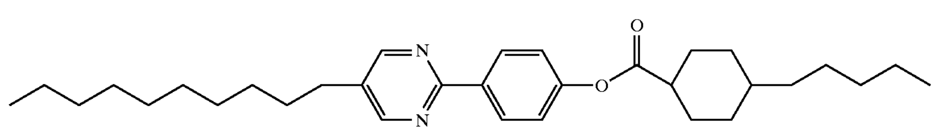 | I-169 –> N-105 –> C-100 –> X; Q |

TABLE 3-continued
MX 9214
| Component | Percent | Structure | Phase diagram |
|---|---|---|---|
| MDW 1135 | 13.50 | 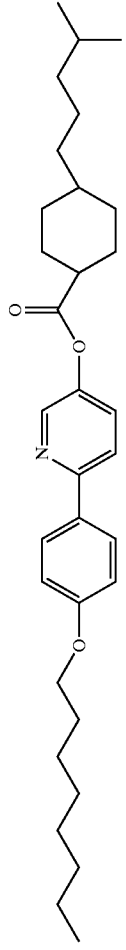 | I-186 -> N-175 -> A-104 -> C - 85 -> S? -> X; S? <- 73.5 - X |
| MDW 1592 | 3.00 | 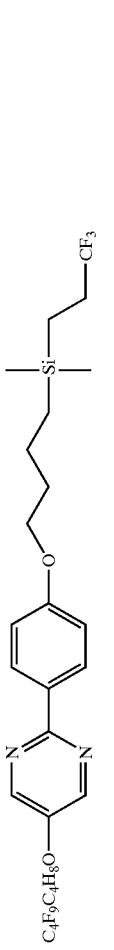 | X -> 69.2 -> I; I -> 55.9 -> X |
| MDW 1532 | 3.00 | 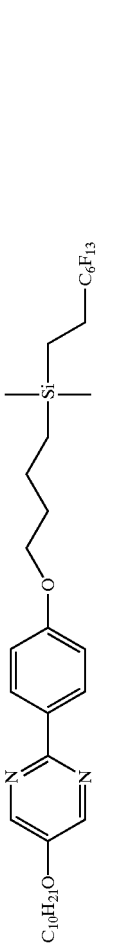 | X 41.1 C 86.1 A 101.3 I 99.6 A 84.8 C |
| MDW | 3.00 |  | K-33 - C-60 - A-74.5 - I; Q |
| MDW | 3.00 |  | K-43.2 - C 62.4 A-66.8 - N-68.2 - I; Q |
| MDW | 3.00 | 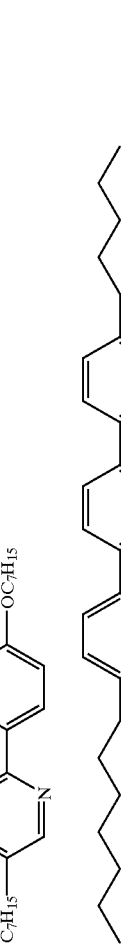 | |
| 671 | 3.00 | 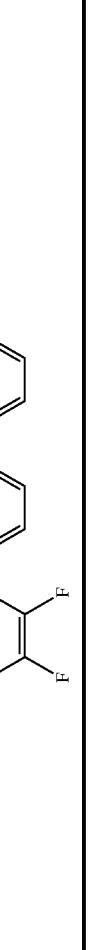 | X-56 -> C-106 -> A-131 -> N-136 -> I |

TABLE 4

MX 9212

| Component | Percent | Structure | Phase diagram |
|---|---|---|---|
| 1658 | 3.00 | 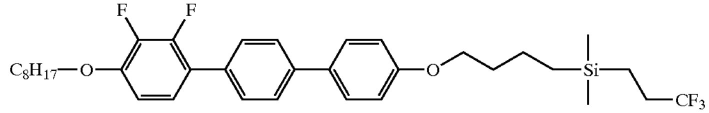 | I 128.4 –> C-37.5 –> X; X-41 –> C |
| 1586 | 3.00 | 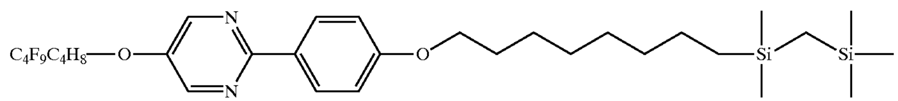 | X-48 –> C-86 –> A-90 –> I; C-42 –> SI-25 –> X |
| 1458 | 12.00 | 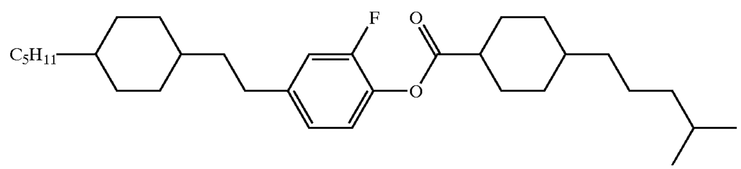 | |
| 1135 | 12.00 | 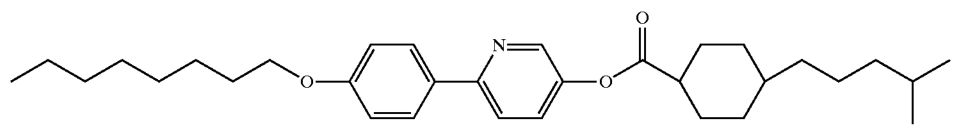 | I-186 –> N-175 –> A –<br>104 –> C-85 –> S?–> X; S? <– 73.5 – X |
| 987 | 16.00 | 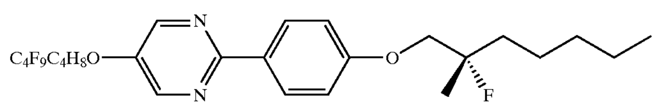 | I-63 –> A-54 –> C*-21 –> X; X-53 –> SI-57 –> C* |
| 950 | 2.00 | 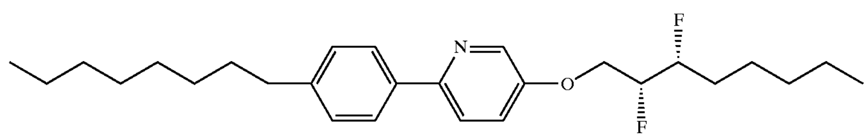 | I-90 –> X; X-94 –> I |
| 913 | 4.00 | 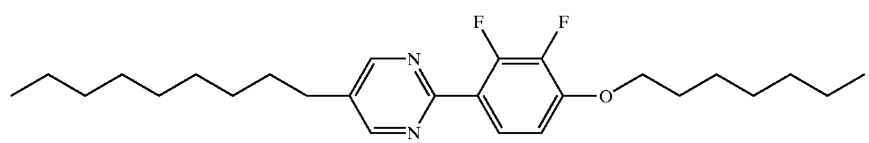 | I-50 –> C-32 –> X; X-43 –> C-50 –> I |

TABLE 4-continued
MX 9212
| Component | Percent | Structure | Phase diagram |
|---|---|---|---|
| 374 | 8.00 | 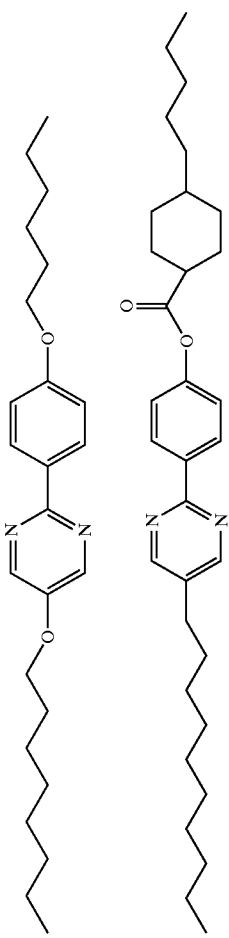 | Q; Q |
| 337 | 15.00 | 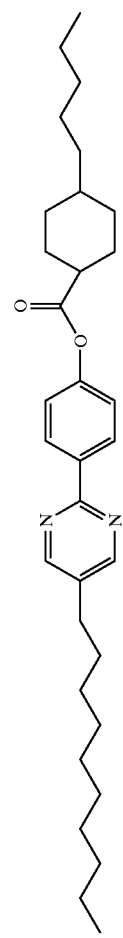 | I-169 –> N-105 –> C-100 –> X; Q |
| 006 | 8.33 | 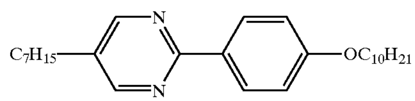 | K-59.5 – C-57.5 – A-63 – N-71 – I; Q |
| 005 | 8.33 | 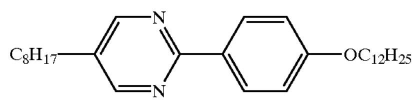 | K-43.2 – C 62.4 A-66.8 – N-68.2 – I; Q |
| 004 | 8.34 | 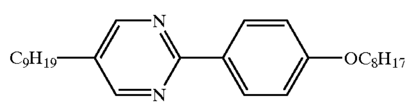 | K-33 – C-60 – A-74.5 – I; Q |

TABLE 5

MX 9215

| Component | Percent | Structure | Phase diagram |
|---|---|---|---|
| 50 | 2.00 | (structure) | I-90 –> X; X-94 –> I |
| 87 | 16.00 | (structure) | I-63 –> A-54 –> C*-21 –> X; X-53 –> S?-57 –> C* |
| 74 | 8.00 | (structure) | Q; Q |
| 13 | 4.00 | (structure) | I-50 –> C-32 –> X; X-43 –> C-50 –> I |
| 632 | 3.00 | (structure) | X 41.1 C 86.1 A 101.3 I 99.6 A 84.8 C |
| 586 | 3.00 | (structure) | X-48 –> C-86 –> A-90 –> I; C-42 –> SI-25 –> X |
| 37 | 18.00 | (structure) | I-169 –> N-105 –> C-100 –> X; Q |

TABLE 5-continued
MX 9215
| Component | Percent | Structure | Phase diagram |
|---|---|---|---|
| 135 | 8.00 | 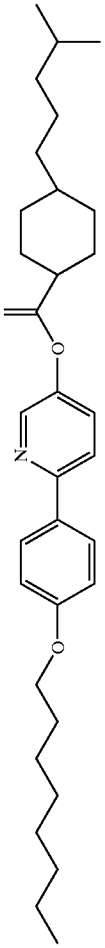 | I-186 -> N-175 -> A-104 -> C-85 -> S? -> X; S? <- 73.5 - X |
| 598 | 4.00 | 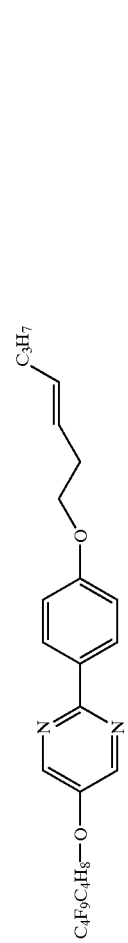 | |
| 673 | 3.00 | 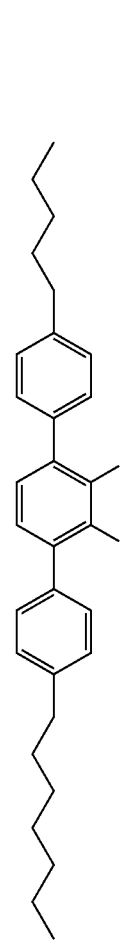 | X-37 -> N-112 -> I; C-24 -> X |
| 458 | 10.00 | 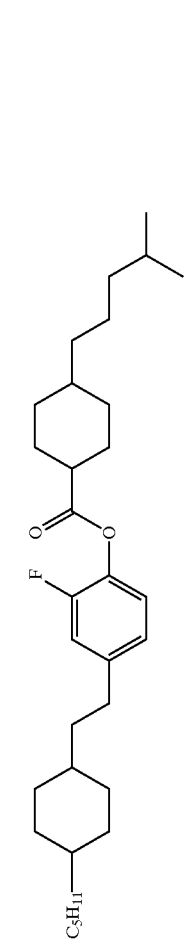 | |
| | 7.00 |  | K-49 - A-44 - N-69.5 - I; Q |
| | 7.00 |  | K-33 - C-60 - A-74.5 - I; Q |
| | 7.00 |  | K-43.2 - C 62.4 A-66.8 - N-68.2 - I; Q |

TABLE 6

MX 9338

| Component | Percent | Structure | Phase diagram |
|---|---|---|---|
| 1597 | 5.56 | $C_4F_9C_4H_8-O-$〈phenyl〉$-$〈pyrimidine〉$-O-CH_2CH_2CH=CH-C_4H_9$ | |
| 1598 | 5.56 | $C_4F_9C_4H_8-O-$〈phenyl〉$-$〈pyrimidine〉$-O-CH_2CH_2CH=CH-C_3H_7$ | I-63 −> A-54 −> C*-21 −> X; X-53 −> S?-57 −> C* |
| 987 | 15.56 | $C_4F_9C_4H_8O-$〈phenyl〉$-$〈pyrimidine〉$-O-CH_2-C*(CH_3)(F)-C_5H_{11}$ | I-90 −> X; X-94 −> I |
| 950 | 4.44 | 〈pyridine〉$-$〈phenyl〉$-C_8H_{17}$ with OCH$_2$CHF-CHF-C$_4$H$_9$ | |
| 644 | 2.22 | 〈pyrimidine〉$-$〈phenyl〉$-O-CH_2-C*H(CH_3)-CH_2-CH(CH_3)_2$ ... | I-41 −> N-20 −> X; X-43 −> N-47 −> I |
| 1673 | 11.11 | 〈phenyl〉$-$〈phenyl〉$-$〈difluorophenyl〉$-C_7H_{15}$ with $C_5H_{11}$ | X-37 −> N-112 −> I; C-24 −> X |
| 1671 | 4.44 | 〈phenyl〉$-$〈phenyl〉$-$〈difluorophenyl〉$-C_7H_{15}$ with $C_5H_{11}$ | X-56 −> C-106 −> A-131 −> N-136 −> I |

TABLE 6-continued
MX 9338
| Component | Percent | Structure | Phase diagram |
|---|---|---|---|
| 1674 | 4.44 | 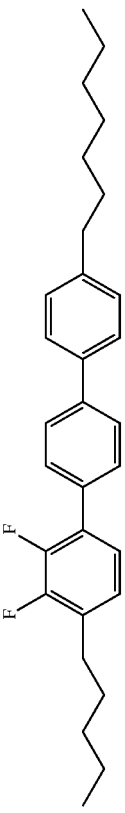 | X-66 -> SI-75 -> C-119 -> A-135 -> N-137 -> I |
| 1701 | 8.89 | 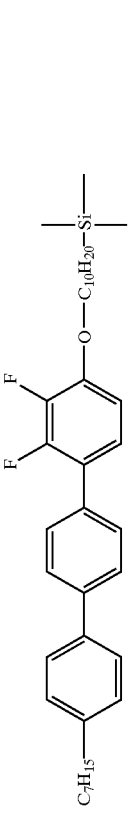 | |
| 337 | 24.44 | 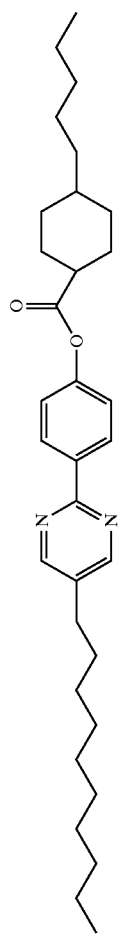 | I-169 -> N-105 -> C-100 -> X; Q |
| 374 | 3.33 | 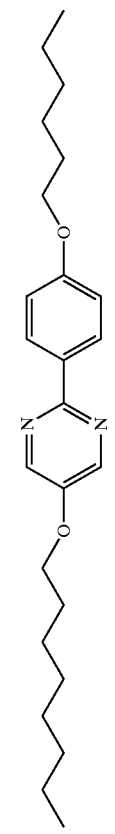 | Q; Q |
| 5 | 3.33 | 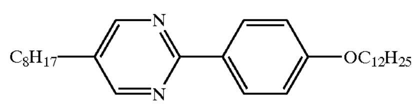 | |
| 1695 | 6.67 | 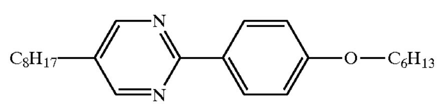 | K-43.2 - C 62.4 A-66.8 - N-68.2 - I; Q |
| | 0.00 | | |
| | 0.00 | | |
| | 0.00 | | |

TABLE 7

MX 9540

| Component | Percent | Structure | Phase diagram |
|---|---|---|---|
| 1671 | 15.00 | 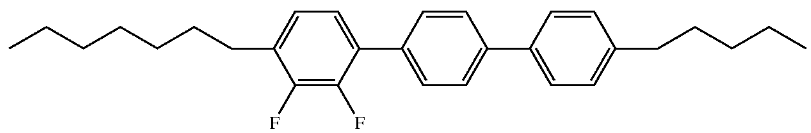 | X-56 -> C-106 -> A-131 -> N-136 -> I |
| 1674 | 15.00 | 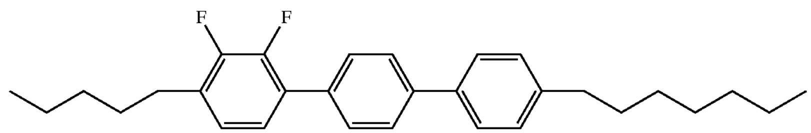 | X-66 -> SI-75 -> C-119 -> A-135 -> N-137 -> I |
| 1673 | 30.00 | 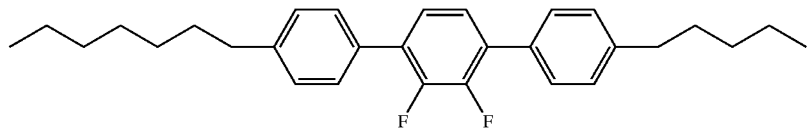 | X-37 -> N-112 -> I; C-24 -> X |
| 1658 | 10.00 | 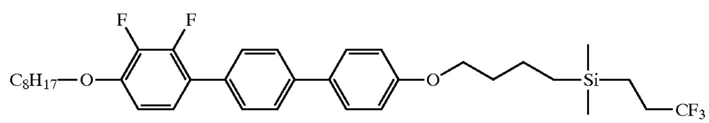 | I 128.4 -> C-37.5 -> X; X-41 -> C |
| 987 | 16.00 | 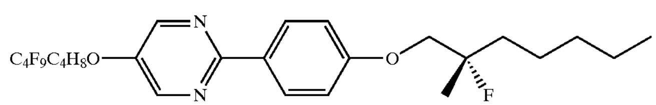 | I-63 -> A-54 -> C*-21 -> X; X-53 -> S?-57 -> C* |
| 950 | 2.00 | 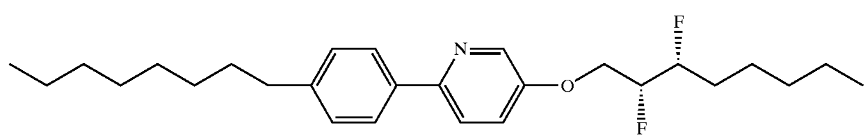 | I-90 -> X; X-94 -> I |
| 337 | 12.00 | 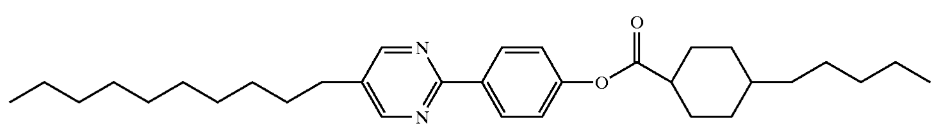 | I-169 -> N-105 -> C-100 -> X; Q |

TABLE 8

MX 9368

| Component | Percent | Structure | Phase diagram |
|---|---|---|---|
| 1671 | 15.00 | 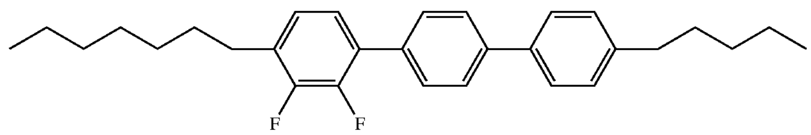 | X-56 –> C-106 –> A-131 –> N-136 –> I |
| 1674 | 15.00 | 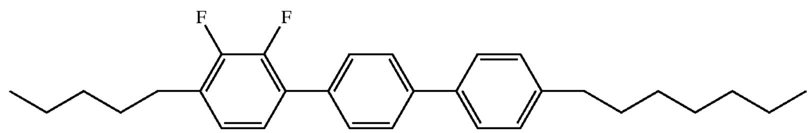 | X-66 –> SI-75 –> C-119 –> A-135 –> N-137 –> I |
| 1673 | 30.00 | 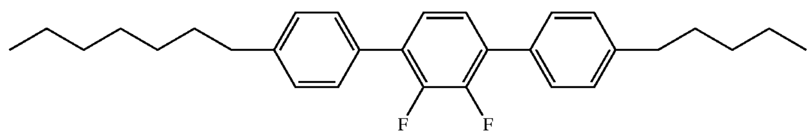 | X-37 –> N-112 –> 1; C-24 –> X |
| 1669 | 10.00 | 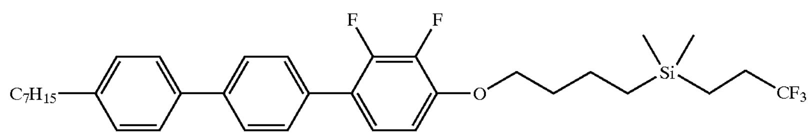 | I-120.5 –> A-92.6 –> C-50 –> Sx –<RT –> X; A-100 –> I |
| 987 | 16.00 | 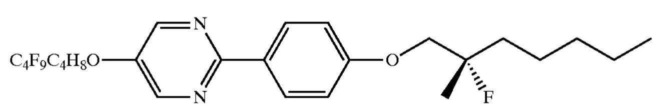 | I-63 –> A-54 –> C*-21 –> X; X-53 –> S?-57 –> C* |
| 950 | 2.00 | 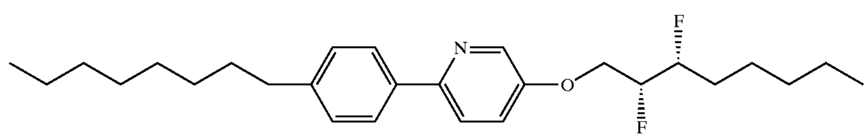 | I-90 –> X; X-94 –> I |
| 337 | 12.00 | 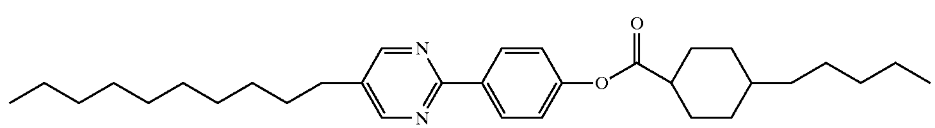 | I-169 –> N-105 –> C-100 –> X; Q |

TABLE 9
MX 9587
| Component | Percent | Structure | Phase diagram |
|---|---|---|---|
| MDW 150 | 3.00 | 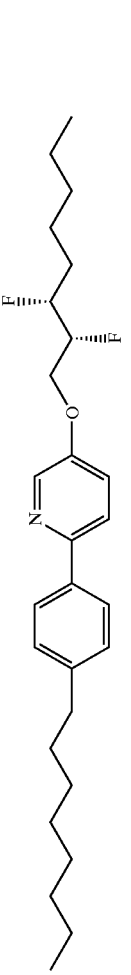 | I-90 –> X; X-94 –> I |
| MDW 144 | 1.00 | 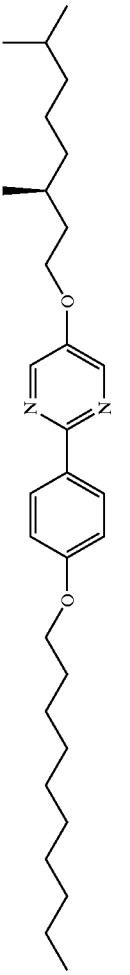 | I-41 –> N-20 –> X; X-43 –> N-47 –> I |
| MDW 187 | 17.00 | 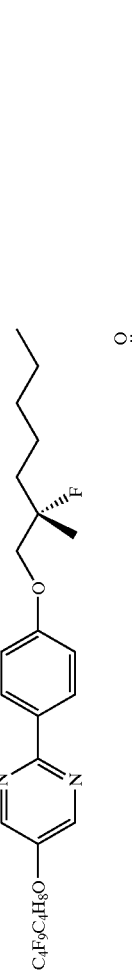 | I-63 –> A-54 –> C*-21 –> X; X-53 –> S?-57 –> C* |
| MDW 1054 | 10.00 | 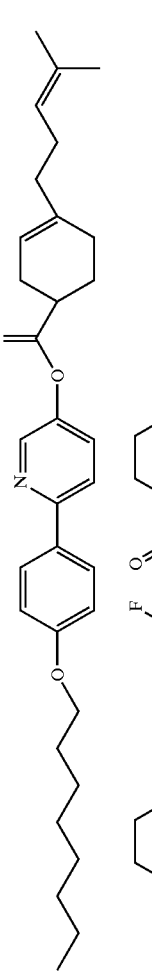 | I-150 –> N-135 –> C –> X; X-55 –> S?-82 –> C |
| MDW 1458 | 15.00 | 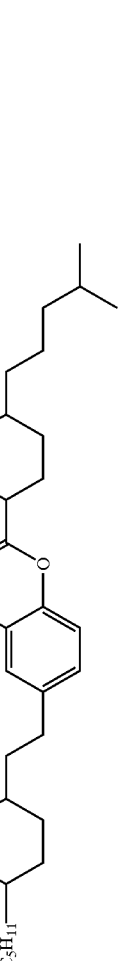 | |
| MDW 136 | 15.00 | 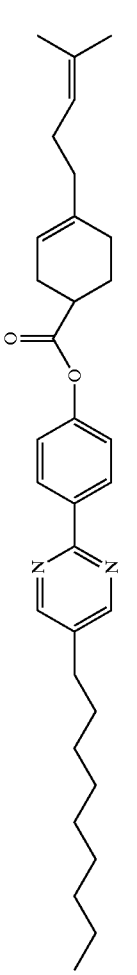 | I-106 –> N-83 –> C-27 –> X; X-40 –> C |

TABLE 9-continued

MX 9587

| Component | Percent | Structure | Phase diagram |
|---|---|---|---|
| MDW 176 | 12.00 | 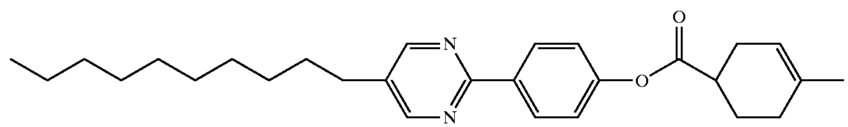 | I-107 –> N-68 –> C-45 –> S?-35 –> X; X-50 –> S?-54 –> C |
| MDW 177 | 3.00 | 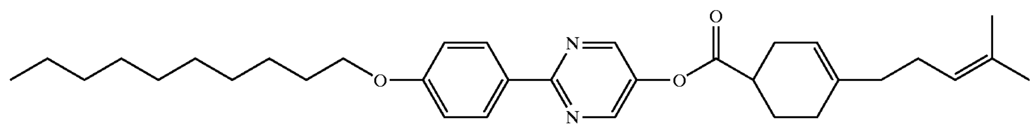 | I-142 –> N-121 –> A-117 –> C-45 –> S? –; Q |
| MDW 319 | 10.00 | 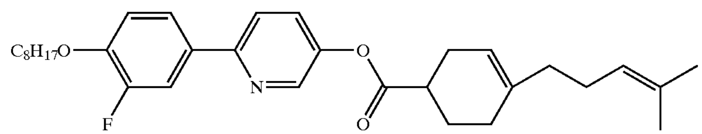 | |
| MDW 313 | 12.00 | 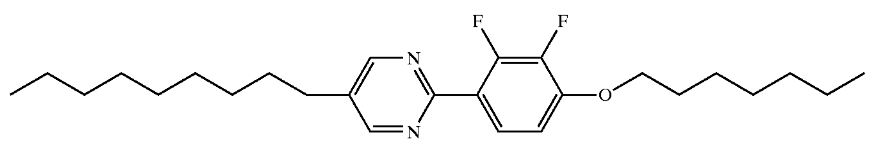 | I-50 –> C-32 –> X; X-43 –> C-50 –> I |
| MDW 1586 | 3.00 | 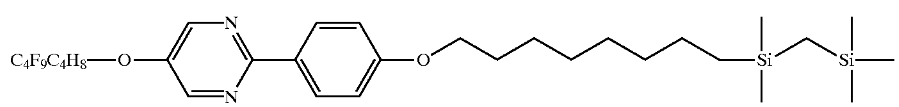 | X-48 –> C-86 –> A-90 –> I; C-42 –> SI-25 –> X |

TABLE 10
MX 9370
| Component | Percent | Structure | Phase diagram |
|---|---|---|---|
| 1671 | 15.00 | 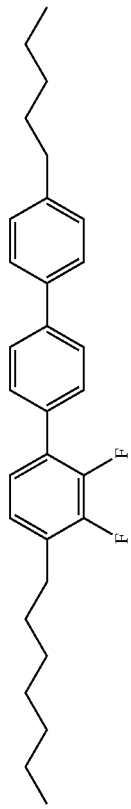 | X-56 –> C-106 –> A-131 –> N-136 –> I |
| 1674 | 15.00 | 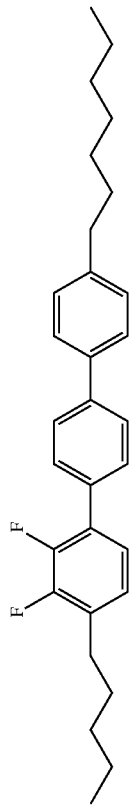 | X-66 –> SI-75 –> C-119 –> A-135 –> N-137 –> I |
| 1673 | 18.00 | 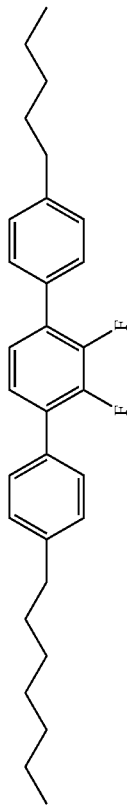 | X-37 –> N-112 –> I; C-24 –> X |
| 1669 | 8.00 | 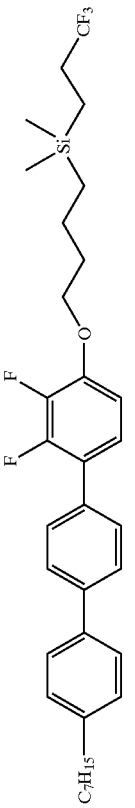 | I-120.5 –> A-92.6 –> C-50 –> Sx-<RT –> X; A-100 –> I |
| 987 | 18.00 | 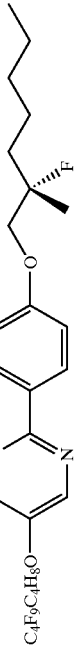 | I-63 –> A-54 –> C*-21 –> X; X-53 –> S?-57 –> C* |

TABLE 10-continued
MX 9370
| Component | Percent | Structure | Phase diagram |
|---|---|---|---|
| 950 | 2.25 | 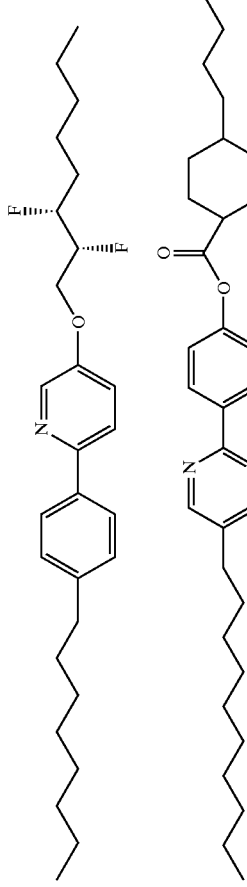 | I-90 –> X; X-94 –> I |
| 337 | 13.75 | 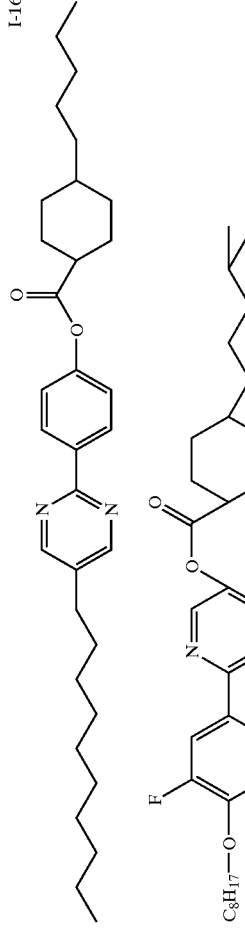 | I-169 –> N-105 –> C-100 –> X; Q |
| 1638 | 5.00 | 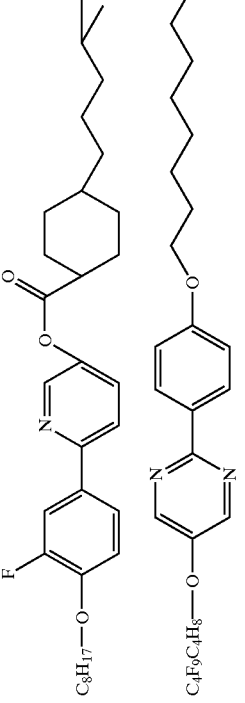 | |
| 1586 | 5.00 | 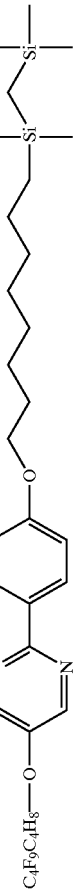 | X-48 –> C-86 –> A-90 –> I; C-42 –> SI-25 –> X |

TABLE 11

MX 9405

| Component | Percent | Structure | Phase diagram |
|---|---|---|---|
| 599 | 1.94 | 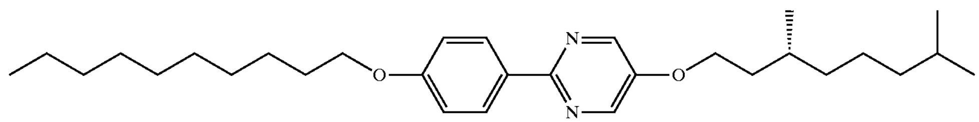 | Q; Q |
| 987 | 13.81 | 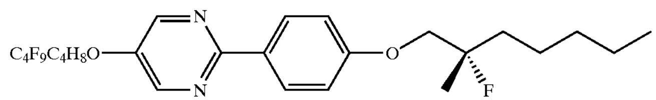 | I-63 -> A-54 -> C*-21 -> X; X-53 - S?-57 -> C* |
| 374 | 10.19 | 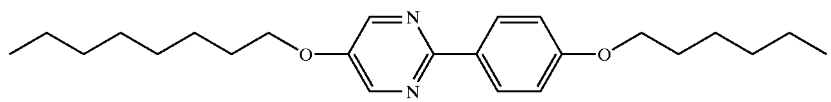 | Q; Q |
| 1586 | 7.14 | 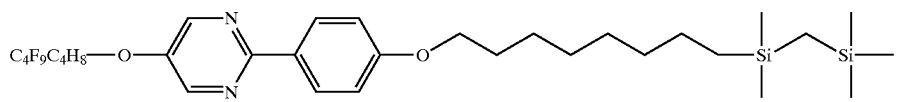 | X-48 -> C-86 -> A-90 -> I; C-42 -> SI-25 -> X |
| 337 | 20.11 | 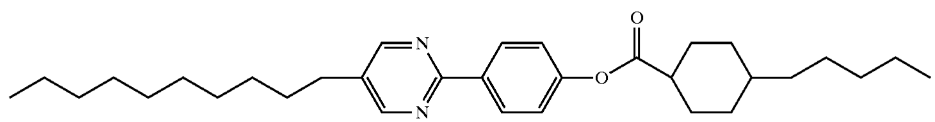 | |
| 1638 | 7.71 | 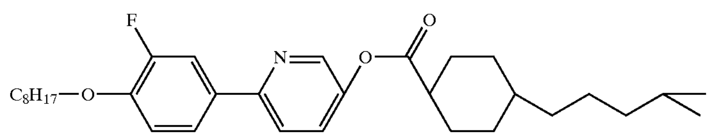 | I-169 -> N-105 -> C-100 -> X; Q |
| 1598 | 5.96 | 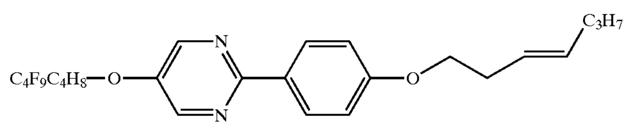 | |

TABLE 11-continued

MX 9405

| Component | Percent | Structure | Phase diagram |
|---|---|---|---|
| 1673 | 2.99 | [structure: terphenyl with difluoro and alkyl chains] | X-37 -> N-112 -> I; C-24 -> X |
| 1458 | 9.82 | [structure: cyclohexyl ester with fluoro phenyl and isoalkyl] | K-43.2 – C 62.4 A-66.8 – N-68.2 – I; Q |
| 5 | 13.56 | [structure: pyrimidine with OC$_{12}$H$_{25}$ and C$_8$H$_{17}$] | |
| 1695 | 6.76 | [structure: pyrimidine with OC$_6$H$_{13}$ and C$_8$H$_{17}$] | |
| | 0.00 | | |
| | 0.00 | | |
| | 0.00 | | |
| | 0.00 | | |

TABLE 12
MX 9417
| Component | Percent | Structure | Phase diagram |
|---|---|---|---|
| 598 | 20.00 | 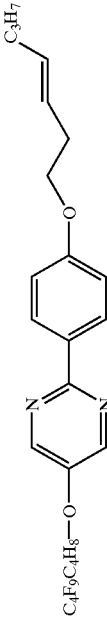 | |
| 87 | 12.00 | 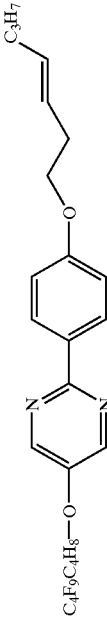 | I-63 –> A-54 –> C*-21 –> X; X-53 –> S?-57 –> C* |
| 50 | 1.50 | 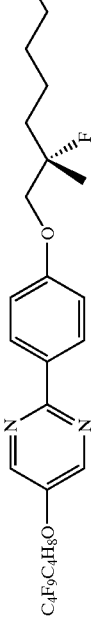 | I-90 –> X; X-94 –> I |
| 673 | 7.00 | 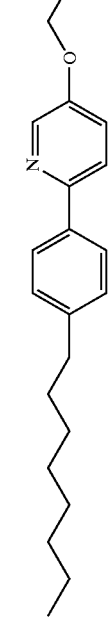 | X-37 –> N-112 –> I; C-24 –> X |
| 671 | 4.00 | 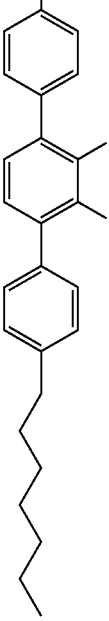 | X-56 –> C-106 –> A-131 –> N-136 –> I |

TABLE 12-continued
MX 9417
| Component | Percent | Structure | Phase diagram |
|---|---|---|---|
| 674 | 4.00 | 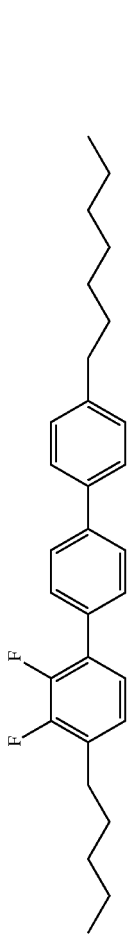 | X-66 –> SI-75 –> C-119 –> A-135 –> N-137 –> I |
| 137 | 25.00 | 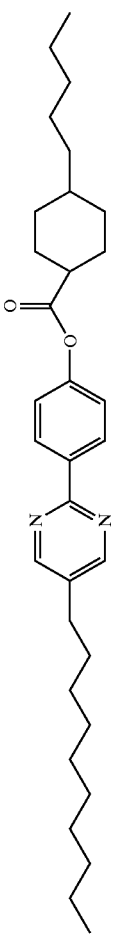 | I-169 –> N-105 –> C-100 –> X; Q |
| 174 | 13.50 | 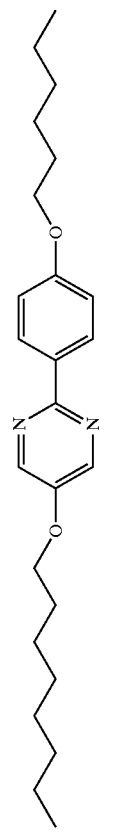 | Q; Q |
| 5 | 13.00 | 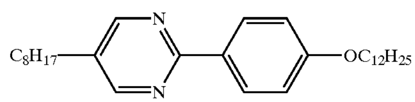 | K-43.2 – C 62.4 A-66.8 – N-68.2 – I; Q |

TABLE 13
MX 9426
| Component | Percent | Structure | Phase diagram |
|---|---|---|---|
| 598 | 7.17 | 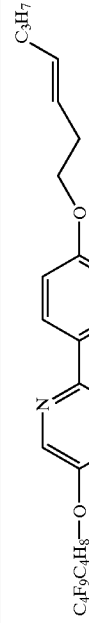 | I-63 –> A-54 –> C*-21 –> X; X-53 –> S? 57 –> C* |
| 87 | 18.25 | 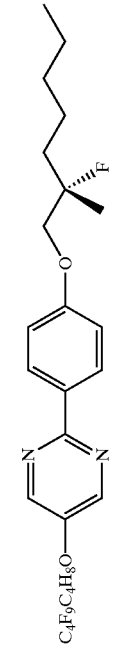 | |
| 50 | 2.28 | 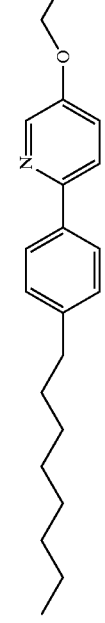 | I-90 –> X; X-94 –> 1 |
| 673 | 7.19 | 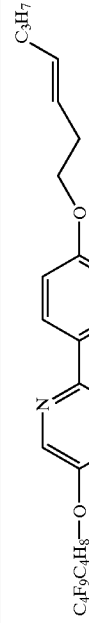 | X-37 –> N-112 –> I; C-24 –> X |
| 671 | 4.08 | 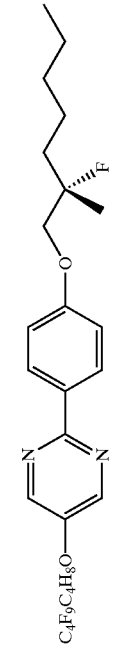 | X-56 –> C-106 –> A-131 –> N-136 –> 1 |
| 674 | 4.13 | 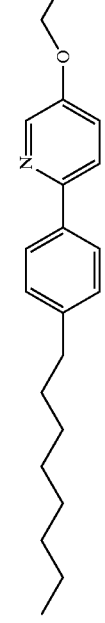 | X-66 –> SI-75 –> C-119 –> A-135 –> N-137 –> I |
| 337 | 26.18 | 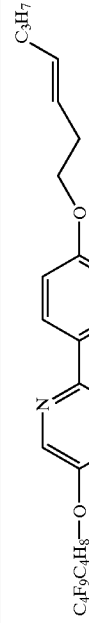 | I-169 –> N-105 –> C-100 –> X; Q |

TABLE 13-continued
MX 9426
| Component | Percent | Structure | Phase diagram |
|---|---|---|---|
| 374 | 10.22 | 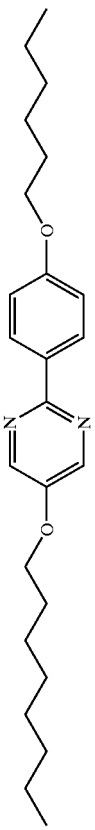 | Q; Q |
| 5 | 7.42 | 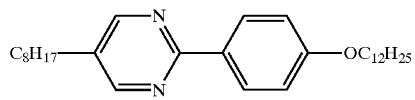 | K-43.2 – C 62.4 A-66.8 – N-68.2 – I; Q |
| 1586 | 5.93 | 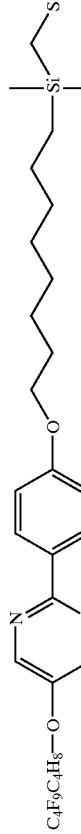 | X-48 –> C-86 –> A-90 –> I; C-42 –> Sl-25 –> X |
| 1597 | 7.15 | 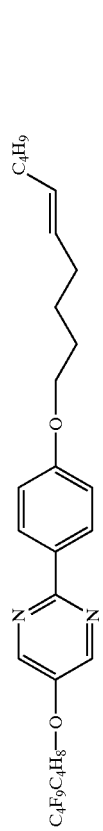 | |
| | 0.00 | | |
| | 0.00 | | |
| | 0.00 | | |
| | 0.00 | | |
| | 0.00 | | |

TABLE 14
MX 9427
| Component | Percent | Structure | Phase diagram |
|---|---|---|---|
| 1597 | 5.56 | 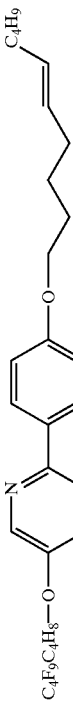 | |
| 1598 | 5.56 | 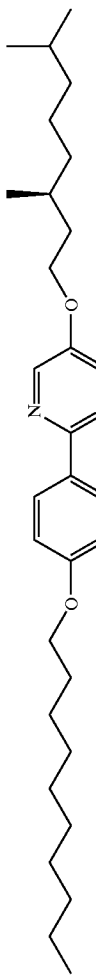 | I-63 → A-54 → C*-21 → X; X-53 → S? – 57 → C* |
| 987 | 15.56 | 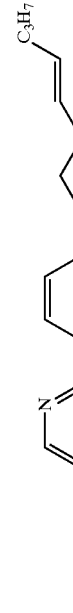 | |
| 950 | 4.17 | 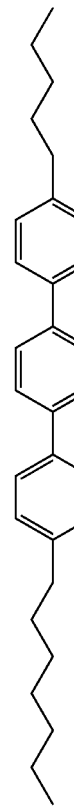 | I-90 → X; X-94 → I |
| 644 | 3.33 | 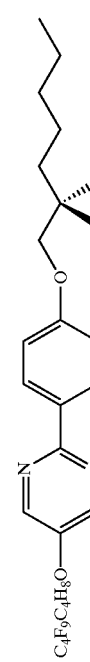 | I-41 → N-20 → X; X-43 → N-47 → I |
| 1673 | 11.11 | 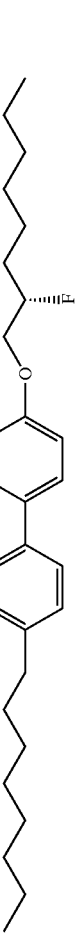 | X-37 → N-112 → I; C-24 → X |
| 1671 | 4.44 | 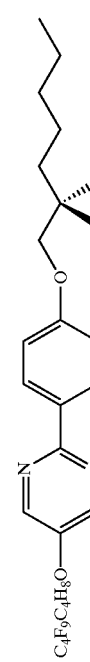 | X-56 → C-106 → A-131 → N-136 → I |

TABLE 14-continued

MX 9427

| Component | Percent | Structure | Phase diagram |
|---|---|---|---|
| 1674 | 4.44 | 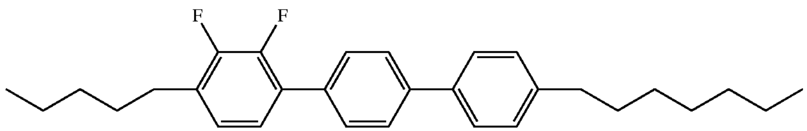 | X-66 -> SI-75 -> C-119 -> A-135 -> N-137 -> I |
| 1658 | 8.89 | 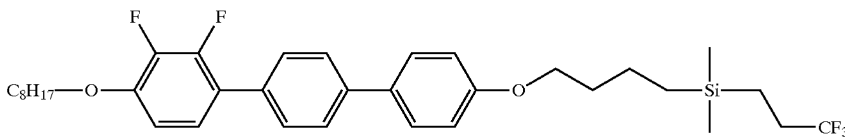 | I 128.4 -> C-37.5 -> X; X-41 -> C |
| 337 | 24.44 | 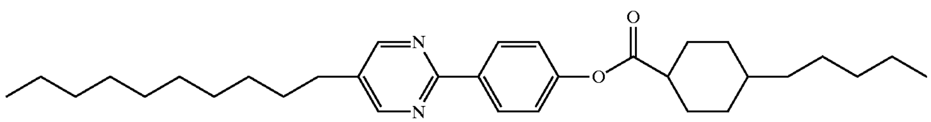 | I-169 -> N-105 -> C-100 -> X; Q |
| 374 | 3.33 | 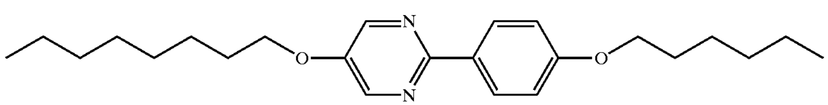 | Q; Q |
| 5 | 3.33 | 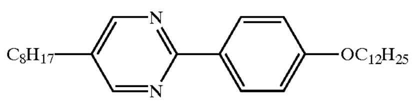 | K-43.2 - C 62.4 A-66.8 - N-68.2 - I; Q |
| 1695 | 5.83 | 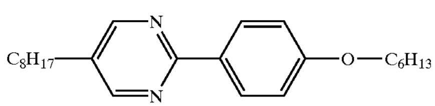 | |
| | 0.00 | | |
| | 0.00 | | |
| | 0.00 | | |

TABLE 15

MX 9431

| Component | Percent | Structure | Phase diagram |
|---|---|---|---|
| MDW 50 | 1.40 | 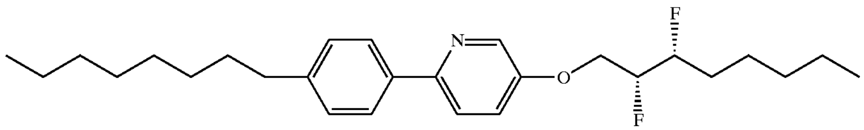 | I-90 –> X; X-94 –> I |
| MDW 87 | 11.20 | 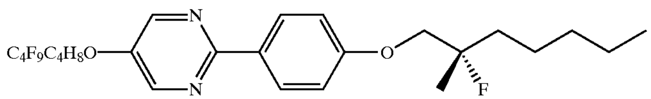 | I-63 –> A-54 –> C*-2I –> X; X-53 –> S? – 57 –> C* |
| MDW 74 | 10.00 | 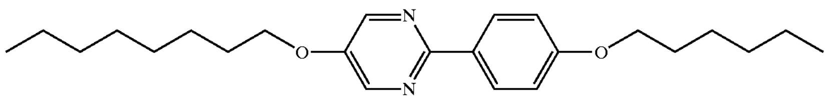 | Q; Q |
| MDW 1561 | 5.00 | 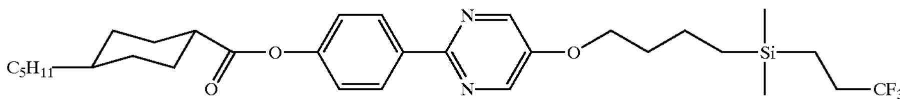 | I-129.6 –> N-71 –> Sx1-66.5 –> Sx2-64 –> X |
| MDW 1586 | 8.00 | 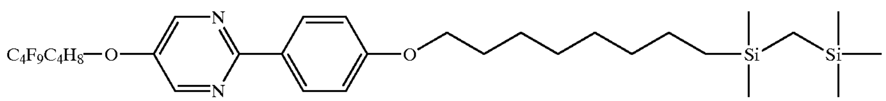 | X-48 –> C-86 –> A-90 –> I; C-42 –> Sl-25 –> X |

TABLE 15-continued

MX 9431

| Component | Percent | Structure | Phase diagram |
|---|---|---|---|
| MDW 37 | 21.40 | 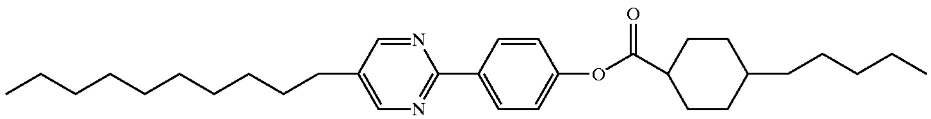 | I-169 -> N-105 -> C-100 -> X; Q |
| MDW 1538 | 8.00 | 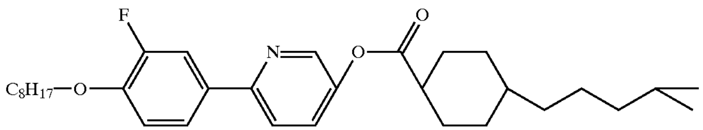 | |
| MDW 1458 | 10.00 | 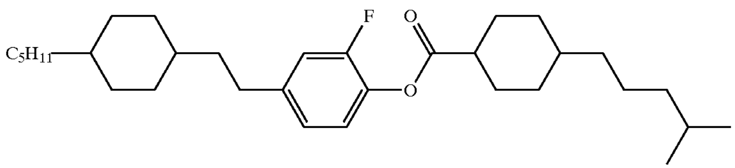 | |
| MDW 1595 | 8.50 | 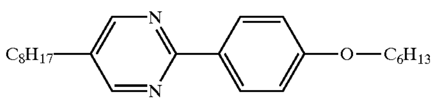 | |
| MDW | 16.50 | 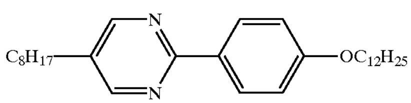 | K-43.2 – C 62.4 A-66.8 – N-68.2 – I; Q |

TABLE 16
MX 9435
| Component | Percent | Structure | Phase diagram |
|---|---|---|---|
| 50 | 4.00 | 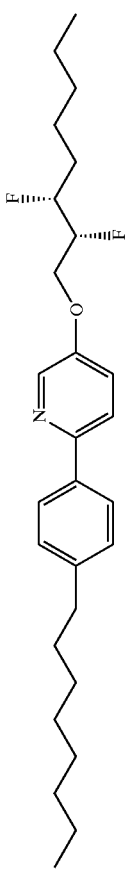 | I-90 –> X; X-94 –> I |
| 87 | 15.00 | 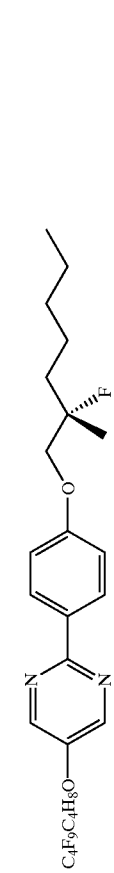 | I-63 –> A-54 –> C*-21 –> X; X-53 –> S?  – 57 –> C* |
| 44 | 3.00 | 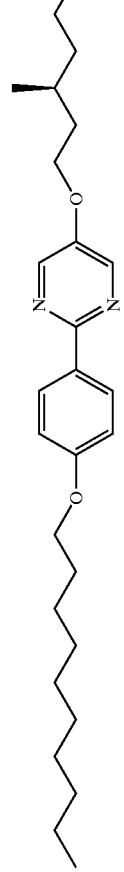 | I-41 –> N-20 –> X; X-43 –> N-47 –> I |
| 673 | 10.00 | 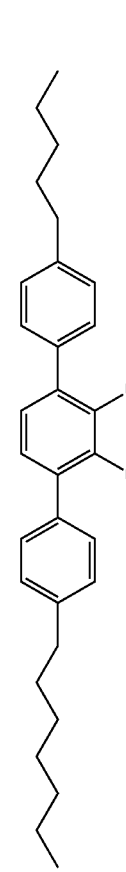 | X-37 –> N-112 –> I; C-24 –> X |
| 1671 | 5.00 | 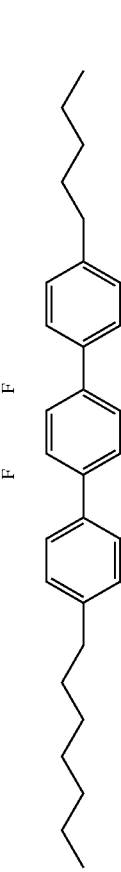 | X-56 –> C-106 –> A-131 –> N-136 –> I |
| 1674 | 5.00 | 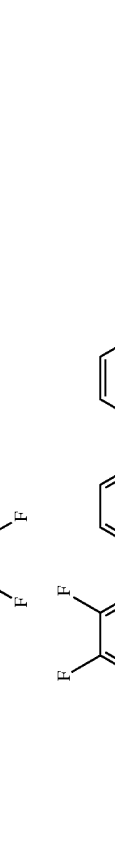 | |
| 1701 | 8.00 | 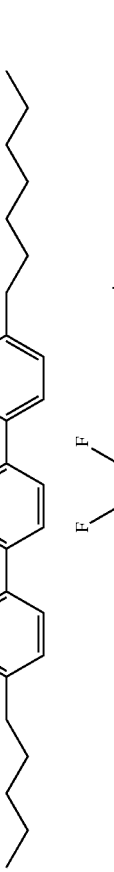 | X-66 –> SI-75 –> C-119 –> A-135 –> N-137 –> I |

TABLE 16-continued

MX 9435

| Component | Percent | Structure | Phase diagram |
|---|---|---|---|
| 337 | 24.00 | 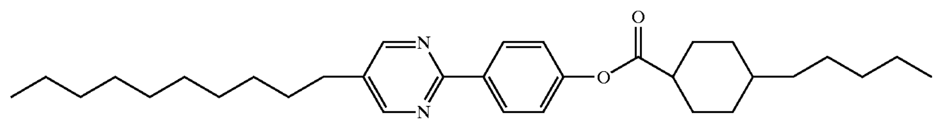 | I-169 –> N-105 –> C-100 –> X; Q |
| 374 | 5.00 | 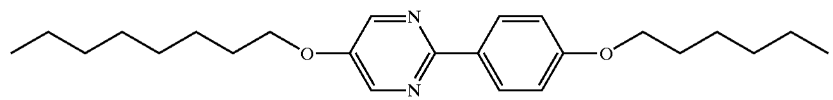 | Q; Q |
| 5 | 9.00 | 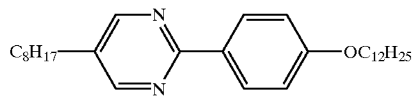 | |
| 913 | 4.00 | 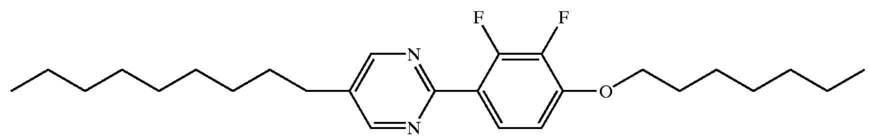 | K-43.2 – C 62.4 A-66.8 – N-68.2 – I; Q |
| 1598 | 4.00 | 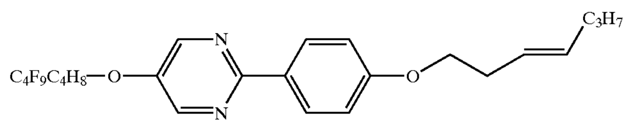 | I-50 –> C-32 –> X; X-43 –> C-50 –> I |
| 1597 | 4.00 | 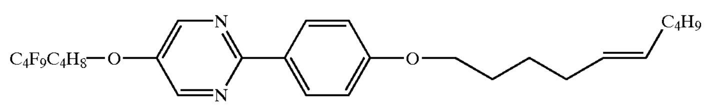 | |
| | 0.00 | | |
| | 0.00 | | |
| | 0.00 | | |

TABLE 17

MX 9441

| Component | Percent | Structure | Phase diagram |
|---|---|---|---|
| 50 | 4.00 | 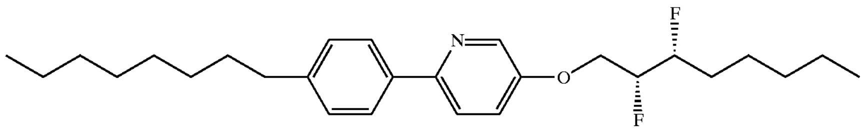 | I-90 –> X; X-94 –> I |
| 87 | 16.00 | 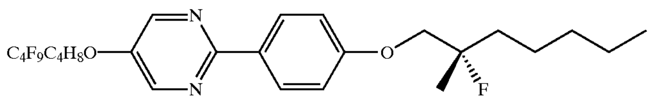 | I-63 –> A-54 –> C*-21 –> X; X-53 –> S?– 57 –> C* |
| 44 | 2.00 | 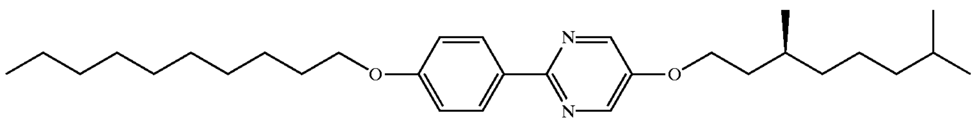 | I-41 –> N-20 –> X; X-43 –> N-47 –> I |
| 673 | 10.00 | 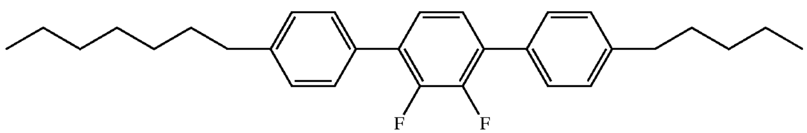 | X-37 –> N-112 –> I; C-24 –> X |
| 671 | 5.00 | 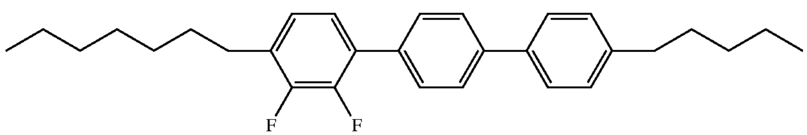 | |
| 674 | 5.00 | 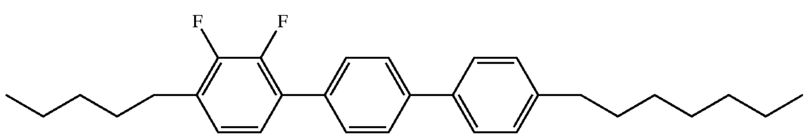 | X-56 –> C-106 –> A-131 –> N-136 –> I |
| 701 | 10.00 | 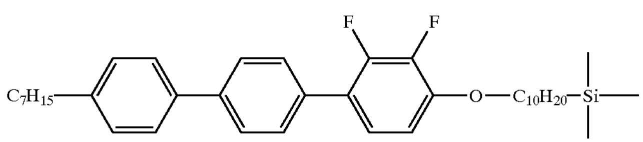 | X-66 –> SI-75 –> C-119 –> A-135 –> N-137 –> I |

TABLE 17-continued

MX 9441

| Component | Percent | Structure | Phase diagram |
|---|---|---|---|
| 37 | 24.00 | 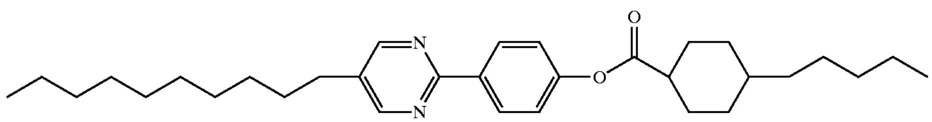 | I-169 -> N-105 -> C-100 -> X; Q |
| | 5.00 | | K-43.2 – C 62.4 A-66.8 – N-68.2 – I; Q |
| 13 | 7.00 | 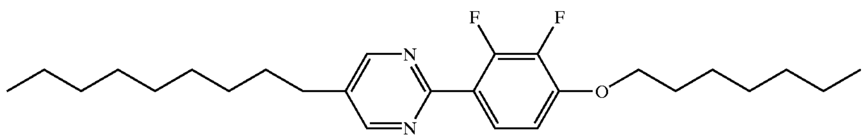 | I-50 -> C-32 -> X; X-43 -> C-50 -> I |
| 598 | 6.00 | 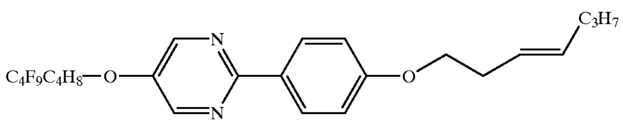 | |
| 597 | 6.00 | 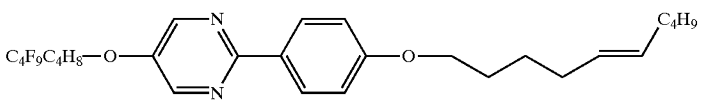 | |

TABLE 18
MX 9451
| Component | Percent | Structure | Phase diagram |
|---|---|---|---|
| 03 | 18.13 | 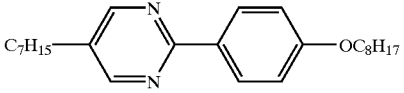 | K-49 – A-44 – N-69.5 – I; Q |
| 04 | 19.45 | 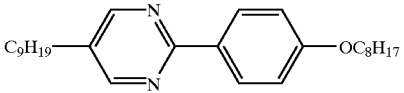 | K-33 – C-60 – A-74.5 – I; Q |
| 05 | 19.45 | 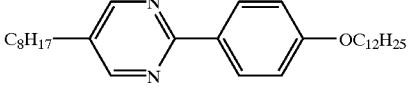 | K-43.2 – C 62.4 A-66.8 – N-68.2 – I; Q |
| 87 | 19.68 | 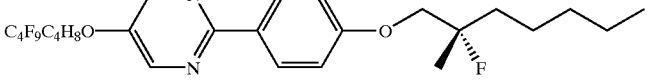 | I-63 -> A-54 -> C*-21 -> X; X-53 -> S?-57 -> C* |
| 74 | 17.23 | 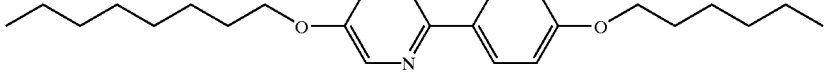 | Q; Q |
| 598 | 6.08 | 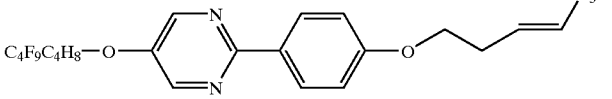 | |
| | 0.00 | | |
| | 0.00 | | |
| | 0.00 | | |
| | 0.00 | | |
| | 0.00 | | |
| | 0.00 | | |
| | 0.00 | | |
| | 0.00 | | |
| | 0.00 | | |
| | 0.00 | | |
| | 0.00 | | |
TABLE 19
MX 9452
| Component | Percent | Structure | Phase diagram |
|---|---|---|---|
| 003 | 18.10 | 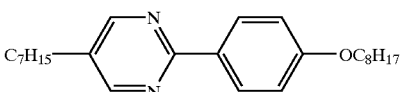 | K-49 – A-44 – N-69.5 – I; Q |
| 004 | 19.42 | 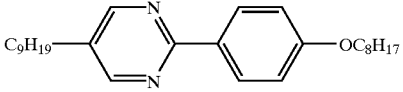 | K-33 – C-60 – A-74.5 – I; Q |
| 005 | 19.42 | 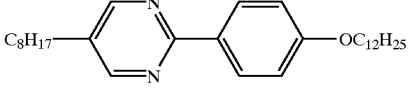 | K-43.2 – C 62.4 A-66.8 – N-68.2 – I; Q |

TABLE 19-continued

MX 9452

| Component | Percent | Structure | Phase diagram |
|---|---|---|---|
| 987 | 18.21 | C$_4$F$_9$C$_4$H$_8$O—[pyrimidine]—[phenyl]—O—CH$_2$—C(CH$_3$)(F)—C$_4$H$_9$ | I-63 -> A-54 -> C*-21 -> X; X-53 -> S?-57 -> C* |
| 374 | 12.81 | C$_7$H$_{15}$—O—[pyrimidine]—[phenyl]—O—C$_6$H$_{13}$ | Q; Q |
| 1598 | 12.04 | C$_4$F$_9$C$_4$H$_8$—O—[pyrimidine]—[phenyl]—O—CH$_2$CH$_2$—CH=CH—C$_3$H$_7$ | |
| | 0.00 | | |
| | 0.00 | | |
| | 0.00 | | |
| | 0.00 | | |
| | 0.00 | | |
| | 0.00 | | |
| | 0.00 | | |
| | 0.00 | | |
| | 0.00 | | |
| | 0.00 | | |

TABLE 20

Mx 9454

| Component | Percent | Structure | Phase diagram |
|---|---|---|---|
| 139 | 7.50 | C₄F₉C₄H₈O-[pyrimidine]-[phenyl]-O-C(=O)-[epoxide]-C₃H₇ | I-75 <– X; I <– 86 – X |
| 44 | 3.75 | [pyrimidine]-[phenyl]-O-CH₂CH₂-*CH(CH₃)-CH₂CH₂CH(CH₃)₂ with C₈H₁₇O- | I-41 –> N-20 –> X; X-43 –> N-47 –> I |
| 598 | 12.50 | C₄F₉C₄H₈O-[pyrimidine]-[phenyl]-O-CH₂-CH=CH-C₃H₇ | — |
| 671 | 10.00 | C₅H₁₁-[phenyl-2,3-F₂]-[phenyl]-[phenyl]-C₇H₁₅ | X-56 –> C-106 –> A-131 –> N-136 –> I |
| 1674 | 10.00 | C₅H₁₁-[phenyl-2,3-F₂]-[phenyl]-[phenyl]-C₈H₁₇ | X-66 –> SI-75 –> C-119 –> A-135 –> N-137 –> I |

TABLE 20-continued

Mx 9454

| Component | Percent | Structure | Phase diagram |
|---|---|---|---|
| 1673 | 17.50 | 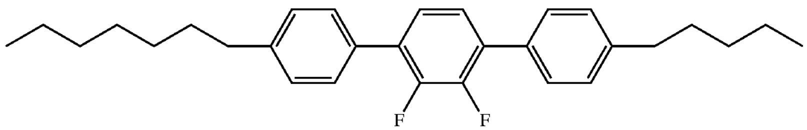 | X-37 -> N-112 -> I; C-24 -> X |
| 337 | 31.25 | 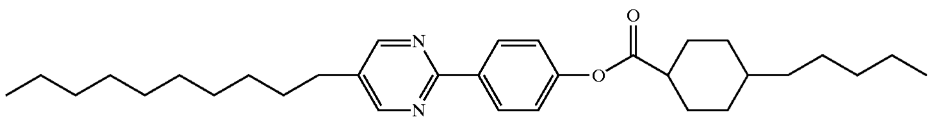 | I-169 -> N-105 -> C-100 -> X; Q |
| 374 | 3.75 | 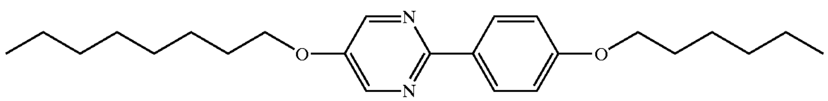 | Q; Q |
| 5 | 3.75 | 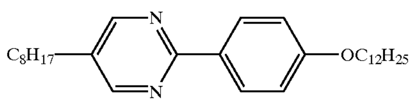 | K-43.2 - C 62.4 A-66.8 - N-68.2 - I; Q |
| | 0.00 | | |
| | 0.00 | | |
| | 0.00 | | |
| | 0.00 | | |
| | 0.00 | | |
| | 0.00 | | |

TABLE 21
| | APT data | | | | Phase Info | | |
|---|---|---|---|---|---|---|---|
| MX # | Ps | Visc | E rise | Dielectric | Phase diagram | DSC MP | DSC FP |
| 9244 | 27.8 | 88.9 | 127 | | I - 107.6 - N - 98.6 - A - 86.3 - C | −25.9 | <−60 |
| 9531 | 28.5 | 84.2 | 132 | 4.43 | I - 107.1 - N - 94.8 - A - 87.7 - C | −21.5 | <−60 |
| 9368 | 24.5 | 103 | 107 | 5.07 | I - 113.9 - N - 105.6 - A - 85.1 - C | −50.9 | −60 |
| 9532 | 21.2 | 83.4 | 190 | 4.92 | I - 128.3 - N - 81.5 - C | −8 | −17.5 |
TABLE 22
MX number 9531
| Component | Percent | Milligrams | Structure | |
|---|---|---|---|---|
| 950 | 2.13 | 2 | 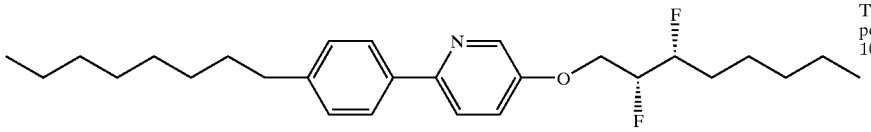 | Total percent 100 |
| 987 | 17.02 | | 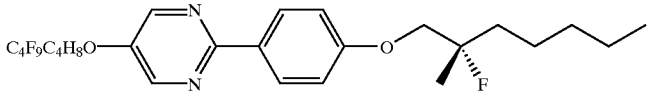 | |
| 1458 | 11.17 | | 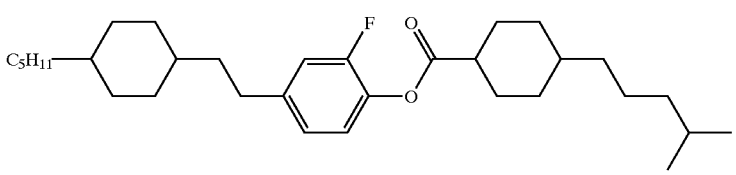 | |
| 913 | 6.38 | | 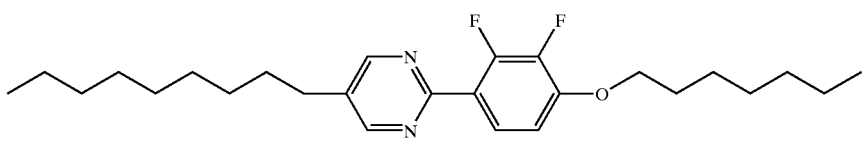 | |
| 911 | 6.38 | | 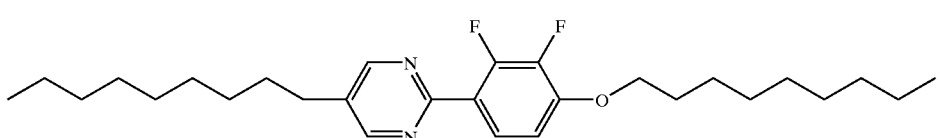 | |
| 374 | 10.64 | | 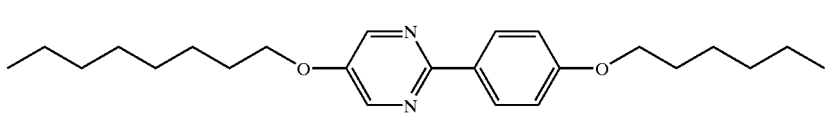 | |
| 337 | 19.15 | | 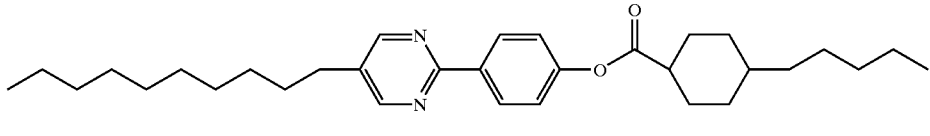 | |
| 1135 | 14.36 | | 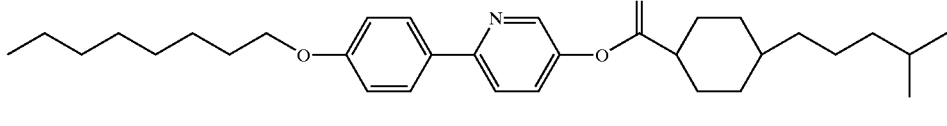 | |
| 4 | 3.19 | | 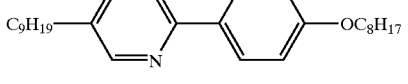 | |

TABLE 22-continued
MX number 9531
| Component | Percent | Milligrams | Structure |
|---|---|---|---|
| 5 | 3.19 | | 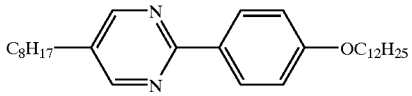 |
| 31 | 3.19 | | 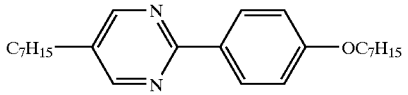 |
| 1671 | 3.19 | | 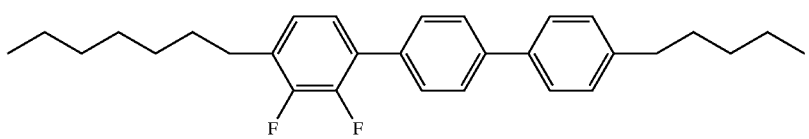 |
TABLE 23
MX number 9532
| Component | Percent | ns | Structure | |
|---|---|---|---|---|
| 1671 | 16.67 | | 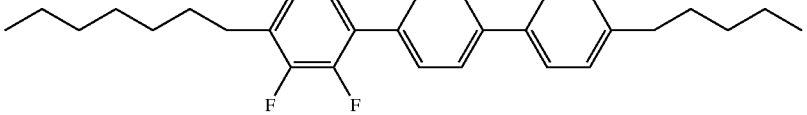 | Total percent 100 |
| 1674 | 16.67 | | 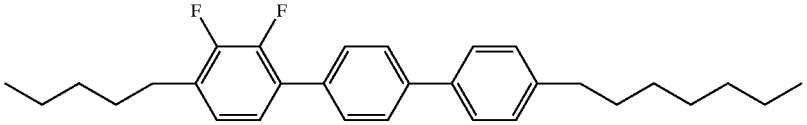 | |
| 1673 | 33.33 | | 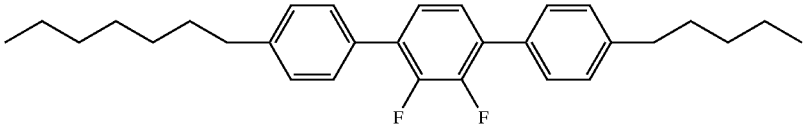 | |
| 987 | 17.78 | | 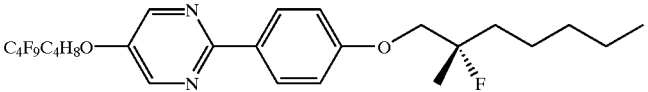 | |
| 950 | 2.22 | | 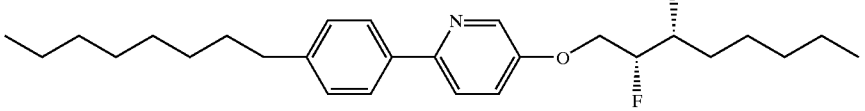 | |
| 337 | 13.33 | | 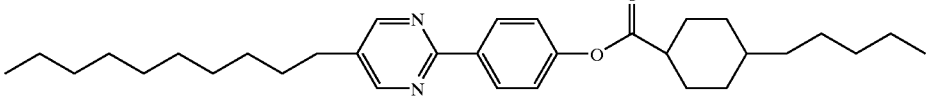 | |

The following examples are intended to further illustrate the invention and are in no way intended to limit the scope of the claims.

EXAMPLES

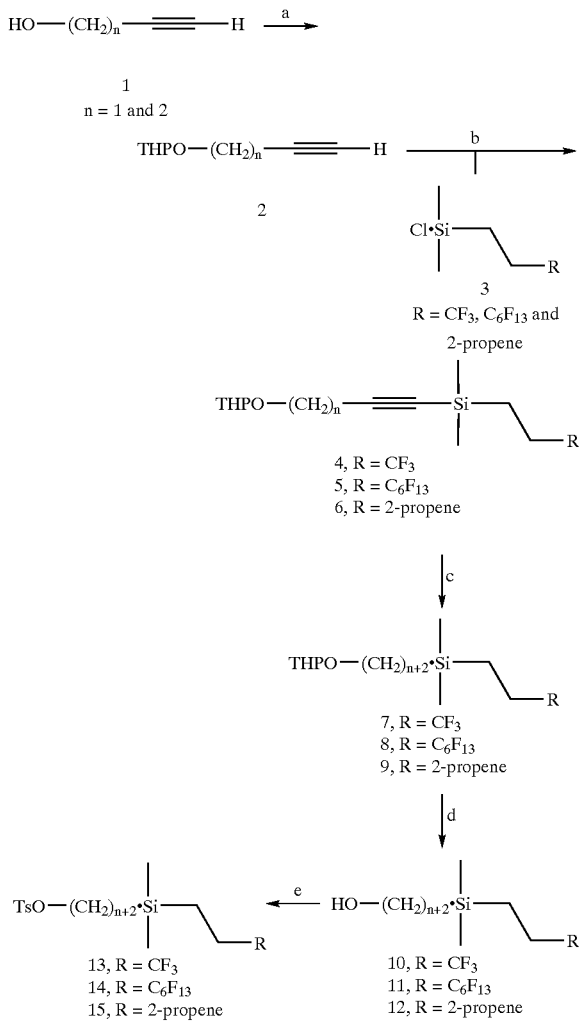

Reactions and reagents used in the preparation of 13, 14 and 15:
a) . . . DHP, POCl$_3$, DCM
b) . . . i) nBuLi, THF, −78° C., ii) Cholorosilane, −78° C.
c) . . . Pd/C, H$_2$, NaHCO$_3$, EtOH/EtOAc
d) . . . PTSA, MeOH
e) . . . TsCl, 0° C.

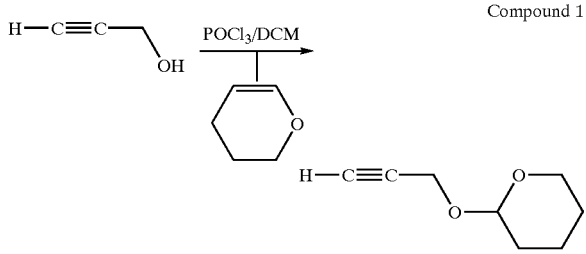

Compound 1

1. 2-Prop-2-ynyloxytetrahydropyran

A solution of phosphoryl chloride (0.5 ml in 10 ml of dichloromethane [DCM])) was added with care to a solution of prop-2-yn-1-ol (7.00 g, 125 mmol) and dihydropyran (10.50 g, 125 mmol) in DCM (80 ml). The reaction mixture was stirred at room temperature for 16 h, washed with sodium hydrogen carbonate solution (3 times), dried (MgSO$_4$) and the solvent removed in vacuo to yield a colorless oil. The crude product was purified by column chromatography [silica gel, eluted with hexane/ethyl acetate (4:1), Rf: 0.43] to yield a colorless oil.

Yield: 12.78 g, 92.29 mmol, 74%

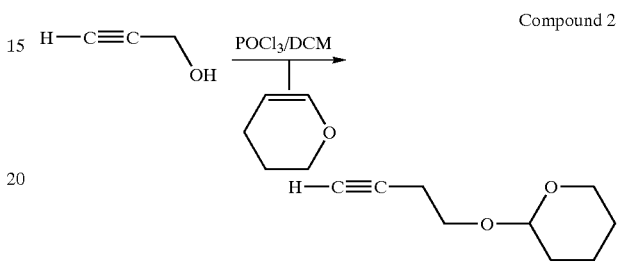

Compound 2

2. 2-But-3-enyloxyterahydropyran

A solution of phosphoryl chloride (0.5 ml in 10 ml of DCM) was added with care to a solution of but-2-yn-1-ol (8.75 g, 125 mmol) and dihydropyran (10.50 g, 125 mmol) in DCM (80 ml). The reaction mixture was stirred at room temperature for 16 h, washed with sodium hydrogen carbonate solution (3 times), dried (MgSO$_4$) and the solvent removed in vacuo to yield a colorless oil. The crude product was purified by column chromatography [silica gel, euted with hexane/ethyl acetate (4:1), Rf: 0.36] to yield a colorless oil.

Yield: 13.37 g, 86.82 mmol, 69%

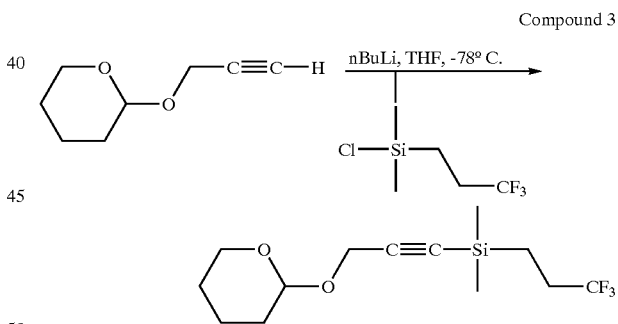

Compound 3

3. Dimethyl-[3-(tetrahydropyran-2-yloxy)-prop-1-ynyl]-(3,3,3,-trifluoropropyl)silane A solution of n-butyllithium (12.0 ml, 30.0 mmol, 2.5 mol dm$^{-3}$ in hexanes) was added dropwise to a stirred, cooled (−78° C.) solution of compound 1 (4.20 g, 30.0 mmol) in THF (80 ml) under an atmosphere of dry nitrogen. The reaction mixture was maintained at −78° C. for 1.5 h and a solution of chlorodimethyl-3,3,3-trifluoropropylsilane (5.72 g, 30.0 mmol) in THF (20 ml) added dropwise. The reaction mixture was allowed to warm to room temperature, washed with water and the organic layer extracted into ethyl acetate/hexane (3 times). The combined extracts were washed with brine, dried (MgSO$_4$) and the solvent removed in vacuo to yield an amber oil. The crude product was purified by column chromatography [silica gel, eluted with hexane/ethyl acetate (4:1), Rf: 0.58] to yield a colorless oil.

Yield: 8.47 g, 28.80 mmol, 96%

Yield: 16.28 g, 29.93 mmol, 99.8%

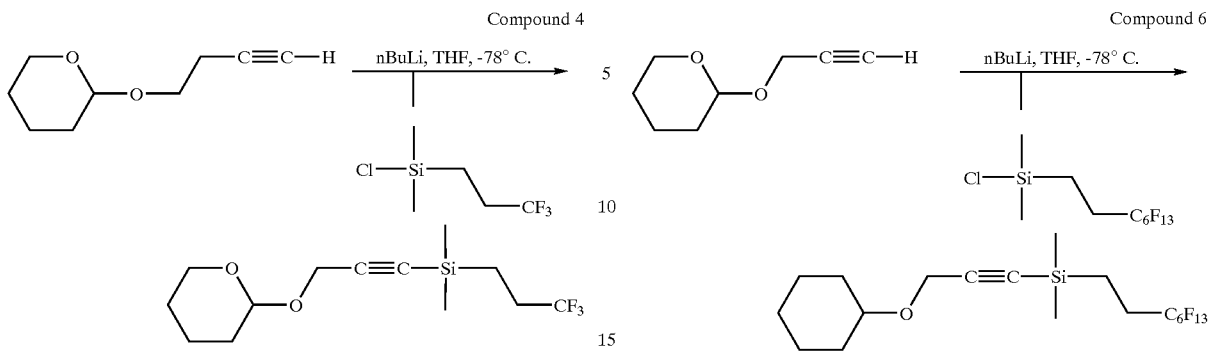

Compound 4

Compound 6

4. 4. Dimethyl-[4-(tetrahydropyran-2-yloxy)-but-1-ynyl]-(3,3,3,-trifluoropropyl)silane A solution of n-butyllithium (8.00 ml, 20 mmol, 2.5 mol dm$^{-3}$ in hexanes) was added dropwise to a stirred, cooled (−78° C.) solution of compound 2 (3.08 g, 20 mmol) in THF (60 ml) under an atmosphere of dry nitrogen. The reaction mixture was maintained at −78° C. for 1.5 h and a solution of chlorodinmethyl-3,3,3-trifluoropropylsilane (3.81 g, 20 mmol) in THF (20 ml) added dropwise. The reaction mixture was allowed to warm to room temperature, washed with water and the organic layer extracted into ethyl acetate/hexane (3 times). The combined extracts were washed with brine, dried (MgSO$_4$) and the solvent removed in vacuo to yield a clear oil, which was purified by column chromatography [silica gel, eluted with hexane/ethyl acetate (19:1), R$_f$: 0.45] to yield a clear oil.

Yield: 6.05 g, 19.64 mmol, 98%

6. Dimethyl-[4-(tetrahydropyran-2-yloxy)-but-1-ynyl]-(tridecafluoro-1,1,2,2-tetrahydrooctyl)-silane A solution of n-butyllithium (12.0 ml, 30.0 mmol, 2.5 mol dm$^{-3}$ in hexanes) was added dropwise to a stirred, cooled (−78° C.) solution of compound 2 (4.62 g, 30.0 mmol) in THF (80 ml) under an atmosphere of dry nitrogen. The reaction mixture was maintained at −78° C. for 1.5 h and a solution of (tridecafluoro-1,1,2,2-tetrahydrooctyl)-dimethylchlorosilane (13.22 g, 30.0 mmol) in THF (20 ml) added dropwise. The reaction mixture was allowed to warm to room temperature, washed with water and the organic layer extracted into ethyl acetate/hexane (3 times). The combined extracts were washed with brine, dried (MgSO$_4$) and the solvent removed in vacuo to yield an amber oil. The crude product was purified by column chromatography [silica gel, eluted with hexane/ethyl acetate (4:1), R$_f$: 0.48]

Yield: 16.30 g, 29.21 mmol, 97%

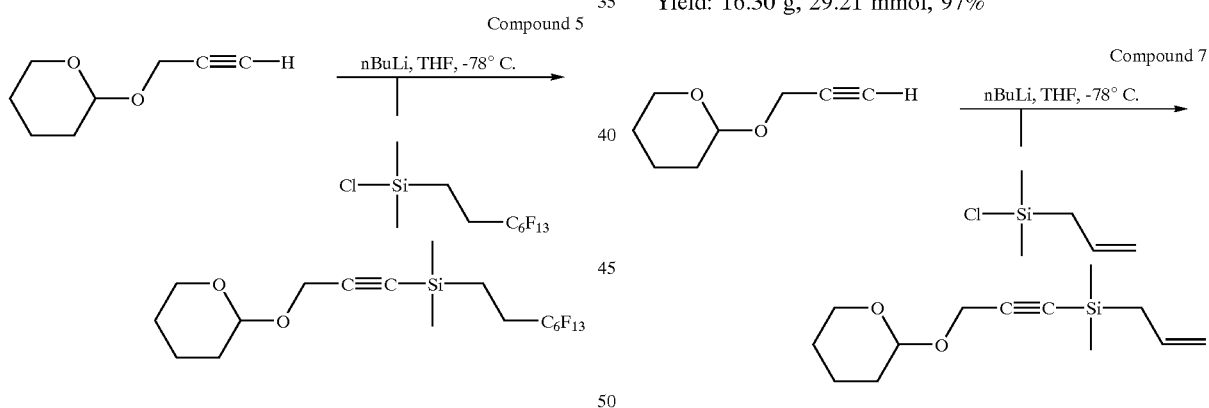

Compound 5

Compound 7

5. Dimethyl-[3-(tetrahydropyran-2-yloxy)-prop-1-ynyl]-(tridecafluoro-1,1,2,2-tetrahydrooctyl)-silane A solution of n-butyllithium (12.0 ml, 30.0 mmol, 2.5 mol dm$^{-3}$ in hexanes) was added dropwise to a stirred, cooled (−78° C.) solution of compound 2 (4.20 g, 30.0 mmol) in THF (80 ml) under an atmosphere of dry nitrogen. The reaction mixture was maintained at −78° C. for 1.5 h and a solution of (tridecafluoro-1,1,2,2-tetrahydrooctyl)-dimethylchlorosilane (13.22 g, 30.0 mmol) in THF (20 ml) added dropwise. The reaction mixture was allowed to warm to room temperature, washed with water and the organic layer extracted into ethyl acetatelhexane (3 times). The combined extracts were washed with brine, dried (MgSO$_4$) and the solvent removed in vacuo to yield an amber oil. The crude product was purified by column chromatography [silica gel, eluted with hexane/ethyl acetate (4:1), R$_f$: 0.58] to yield a clear oil.

7. Allyldimethyl-[3-(tetrahlydropyran-2-yloxy)-prop-1-ynyl]-silane

A solution of n-butyllithium (12.0 ml, 30 mmol, 2.5 mol dm$^{-3}$ in hexanes) was added dropwise to a stirred, cooled (−78° C.) solution of compound 1 (4.20 g, 30 mmol) in THF (60 ml) under an atmosphere of dry nitrogen. The reaction mixture was maintained at −78° C. for 1.5 h and a solution of allylchlorodimethylsilane (4.04 g, 30 mmol) in THF (20 ml) added dropwise. The reaction mixture was allowed to warm to room temperature, washed with water and the organic layer extracted into ethyl acetate/hexane (3 times). The combined extracts were washed with brine, dried (MgSO$_4$) and the solvent removed in vacuo to yield a clear oil. The crude product was purified by column chromatography [silica gel, eluted with hexane/ethyl acetate (4:1), R$_f$: 0.50]

Yield: 7.03 g, 29.52 mmol, 98%

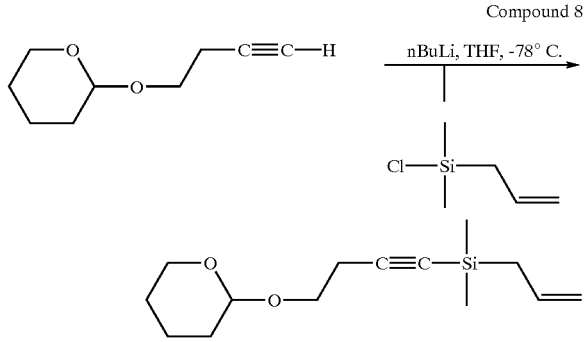

Compound 8

8. Allyldimethyl-[4-(terahydropyran-2-yloxy)-but-1-ynyl]-silane

A solution of n-butyllithium (12.0 ml, 30 mmol, 2.5 mol dm$^{-3}$ in hexanes) was added dropwise to a stirred, cooled (–78° C.) solution of compound 2 (4.62 g, 30 mmol) in THF (60 ml) under an atmosphere of dry nitrogen. The reaction mixture was maintained at –78° C. for 1.5 h and a solution of allylchlorodimethylsilane (4.04 g, 30 mmol) in THF (20 ml) added dropwise. The reaction mixture was allowed to warm to room temperature, washed with water and the organic layer extracted into ethyl acetate/hexane (3 times). The combined extracts were washed with brine, dried (MgSO$_4$) and the solvent removed in vacuo to yield a clear oil. The crude product was purified by column chromatography [silica gel, eluted with hexane/ethyl acetate (4:1), R$_f$: 0.48]

Yield: 7.11 g, 28.20 mmol, 94%

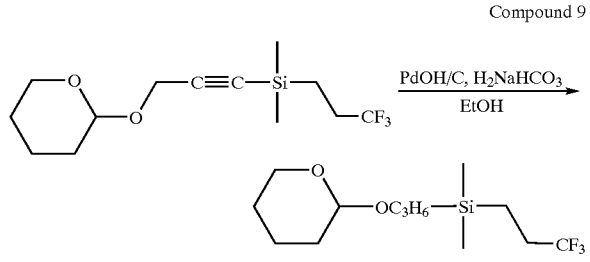

Compound 9

9. Dimethyl-[3-(tetrahydropyran-2-yloxy)-propyl]-(3,3,3-trifluoropropyl)-silane A suspension of compound 3 (5.00 g, 20.00 mmol) palladium hydroxide on charcoal (0.68 g, 0.21 mmol) in ethyl acetate and ethanol (100 ml, 9:1) and sodiumhydrohen carbonate (0.165 g, 1.96 mmol) were stirred at room temperature and a pressure of 100 pounds inch-2 under hydrogen for 24. The reaction mixture was filtered and the solvent removed in vacuo to yield a colorless oil. The crude product was purified by column chromatography [silica gel, eluted with hexane/ethyl acetate (4:1), Rf: 0.58] to yield a colorless oil.

Yield: 5.08 g, 20.00 mmol, 100%

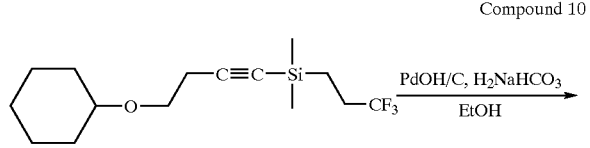

Compound 10

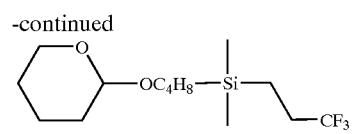

10. Dimethyl-[4-(tetrahydropyran-2-yloxy)-butyl]-(3,3,3-trifluoropropyl)-silane A suspension of compound 4 (6.05 g, 19.64 mmol) palladium hydroxide on charcoal (0.68 g, 0.21 mmol) in ethyl acetate and ethanol (100 ml, 9:1) and sodium bicarbonate (0.165 g, 1.96 mmol) were stirred at room temperature and a pressure of 100 pounds inch$^{-2}$ under hydrogen for 24. The reaction mixture was filtered and the solvent removed in vacuo to yield a colorless oil. The crude product was purified by column chromatography [silica gel, eluted with hexane/ethyl acetate (4:1), R$_f$: 0.56] to yield a colorless oil.

Yield: 6.12 g, 19.62 mmol, 100%

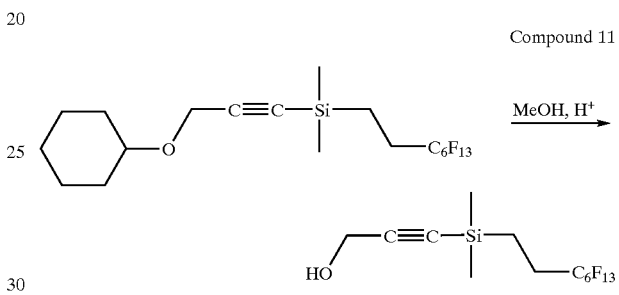

Compound 11

11. 3-[Dimethyl-(tridecafluoro-1,1,2,2-tetrahydrooctyl)silanyl]-prop-2-yn-1-ol A solution of compound 5 (16.28 g, 29.93 mmol) and p-toluenesulphonic acid (1.14 g 5.98 mmol) in methanol (100 ml) and water (20 ml) was stirred at room temperature for 24 h. The reaction mixture was washed with sodium hydrogen carbonate (3 times) and the organic layer extracted into ethyl acetate/hexane (3 times). The combined extracts were washed with brine, died (MgSO$_4$) and the solvent removed in vacuo to yield an amber oil the crude product was purified by column chromatography [silica gel, eluted with hexane/ethyl acetate (4:1), Rf: 0.23] to yield a colorless oil.

Yield: 11.50 g, 25.00 mmol, 84%

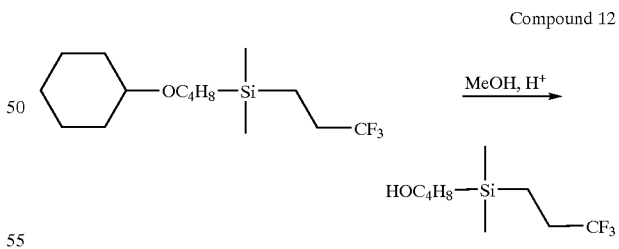

Compound 12

12. 4-[Dimethyl-(3,3,3-trifluoropropyl)-silanyl)]-butan-1-ol

A solution of compound 8 (6.12 g, 19.62 mmol) and p-toluenesulphonic acid (0.75 g 3.92 mmol) in methanol (80 ml) and water (15 ml) was stirred at room temperature for 24 h. The reaction mixture was washed with sodium hydrogen carbonate (3 times) and the organic layer extracted into ethyl acetate/hexane (3 times). The combined extracts were washed with brine, died (MgSO$_4$) and the solvent removed in vacuo to yield an amber oil. The crude product was purified by column chromatography [silica gel, eluted with hexane/ethyl acetate (4:1), Rf: 0.22] to yield a colorless oil.

Yield: 4.47 g, 19.62 mmol, 100%

Compound 13

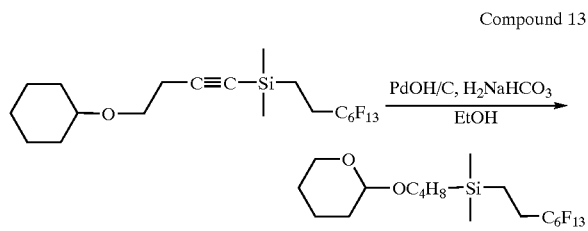

13. Dimethyl-[tetrahydropyran-2-yloxy)-butyl]-(tridecafluoro-1,1,2,2-tetrahydrooctyl)-silane A suspension of compound 6 (16.60 g, 29.75 mmol) palladium hydroxide on charcoal (1.03 g, 0.89 mmol) in ethyl acetate and ethanol (200 ml, 9:1) and sodium bicarbonate (2.50 g, 29.74 mmol) were stirred at room temperature and a pressure of 100 pounds/inch² under hydrogen for 24 h. The reaction mixture was filtered and the solvent removed in vacuo to yield a colorless oil. The crude product was purified by column chromatography [silica gel, eluted with hexane/ethyl acetate (4:1), Rf: 0.47] to yield a colorless oil.

Yield: 16.72 g, 29.75 mmol, 100%

Compound 14

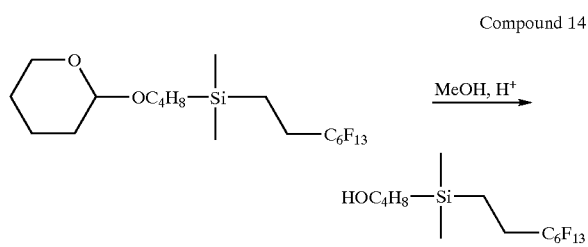

14. 4-[Dimethyl-(tridecafluoro-1,1,2,2-tetrahydrooctyl)-silane]-butan-1-ol

A solution of compound 13 (16.72 g, 29.75 mmol) and p-toluenesulfonic acid (1.13 g 5.95 mmol) in methanol (80 ml) and water (10 ml) was stirred at room temperature for 24 h. The reaction mixture was washed with sodium hydrogen carbonate (3 times) and the organic layer extracted into ethyl acetate/hexane (3 times). The combined extracts were washed with brine, dried (MgSO$_4$) and the solvent removed in vacuo to yield a clear oil. The crude product was purified by column chromatography [silica gel, eluted with hexane/ethyl acetate (4:1), Rf: 0.04] to yield a colorless oil.

Yield: 13.92 g, 29.75 mmol, 100%

Compound 15

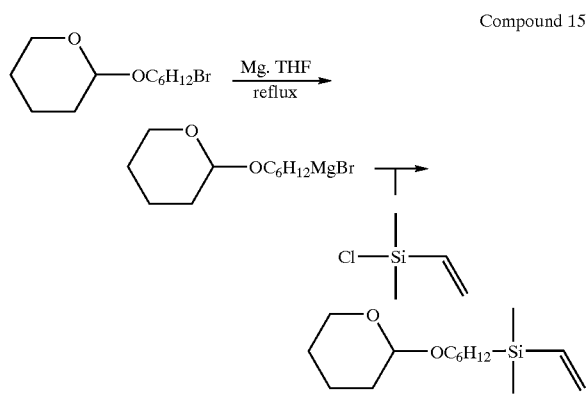

15. Dimethyl-[6-(tetrahydropyran-2-yloxy)-hexl]-vinylsilane

A solution of 2-(6-bromohexyloxy)-tetrahydropyran (5.30 g, 20.0 mmol) in THF (40 ml) added dropwise to a stirred suspension of magnesium (0.583 g, 24.0 mmol) in THF (40 ml) under an atmosphere of dry nitrogen. The reaction mixture was heated under reflux for 0.5 h, cooled to room temperature and canulated into a solution of chlorodimethylvinylsilane (2.35 g, 20.0 ml) in THF (40 ml); the resulting mixture was stirred at room temperature for 18 h, washed with water and the organic layer extracted into hexane (3×40 ml). The combined extracts were washed with brine, dried (MgSO$_4$) and the solvent removed in vacuo to yield a colorless oil. The crude product was purified by column chromatography [silica gel, eluted with hexane/ethyl acetate (9:1), R$_f$: 0.35] to yield a colorless oil.

Yield: 3.01 g, 11.15 mmol, 56%

Compound 16

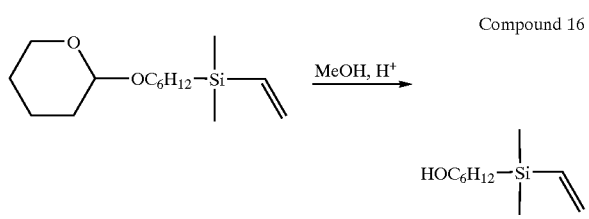

16. 6-(Dimethylvinylsilanyl)-hexan-1-ol

A solution of compound 15 (3.01 g, 11.15 mmol) and p-toluenesulfonic acid (0.42 g, 2.23 mmol) in methanol (60 ml) and water (10 ml) was stirred at room temperature for 24 h, washed with water and the organic layer extracted into hexane/ethyl acetate (3×40 ml, 1:1). The combined extracts were washed with brine, dried (MgSO$_4$) and the solvent removed in vacuo. The residues were purified by column chromatography [silica gel, eluted with hexane/ethyl acetate (4:1), R$_f$: 0.08)] to yield a clear oil.

Yield: 2.07 g, 11.15 mmol, 100%

Compound 17

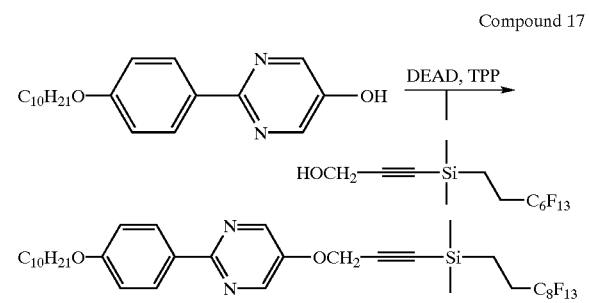

17. 2-(Decyloxyphenyl)-5-{3-[dimethyltridecafluoro-1,1,2,2-tetralydooctylsilanyl]-prop-2-ynyloxy}-pyrimidine A solution of diethylazodicaboxylate (DEAD) (0.261 g, 1.50 mmol) in THF (20 ml) was added dropwise to a stirred solution of 2-(4-decyloxyphenyl)-5-hydroxypyrimidine (0.69 g, 1.50 mmol), compound 11 (0.492 g, 1.50 mmol) and triphenylphosphine (0.393 g, 1.50 mmol) in THF (50 ml) and the reaction mixture stirred at room temperature for 24 h. The solvent was removed in vacuo and the residues purified by column chromatography [silica gel, eluted with hexane/ethyl acetate (4:1), R$_f$: 0.44] to yield a colorless solid, which was recrystallized from ethanol.

Yield: 0.98 g, 127 mmol, 85%

Transitions: Cr 102.7 I° C.

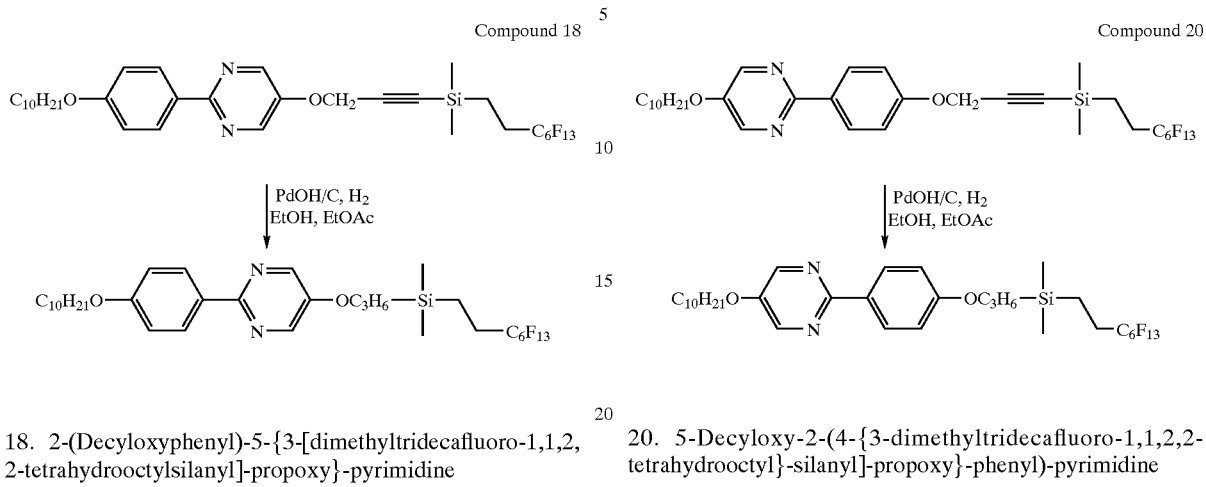

18. 2-(Decyloxyphenyl)-5-{3-[dimethyltridecafluoro-1,1,2,2-tetrahydrooctylsilanyl]-propoxy}-pyrimidine A suspension of compound 17 (0.50 g, 0.65 mmol) and palladium hydroxide on charcoal (37.5 mg, 0.03 mmol) in ethyl acetate and methanol (90 ml, 2:1) was stirred at room temperature and a pressure of 200 pounds/inch$^2$ under hydrogen for 48 h. The reaction mixture was filtered (silica gel) and the crude product recrystallized from ethanol to yield colorless crystals.

Yield: 0.50 g, 0.64 mmol, 98%

Transitions: Cr 90.5 I° C.

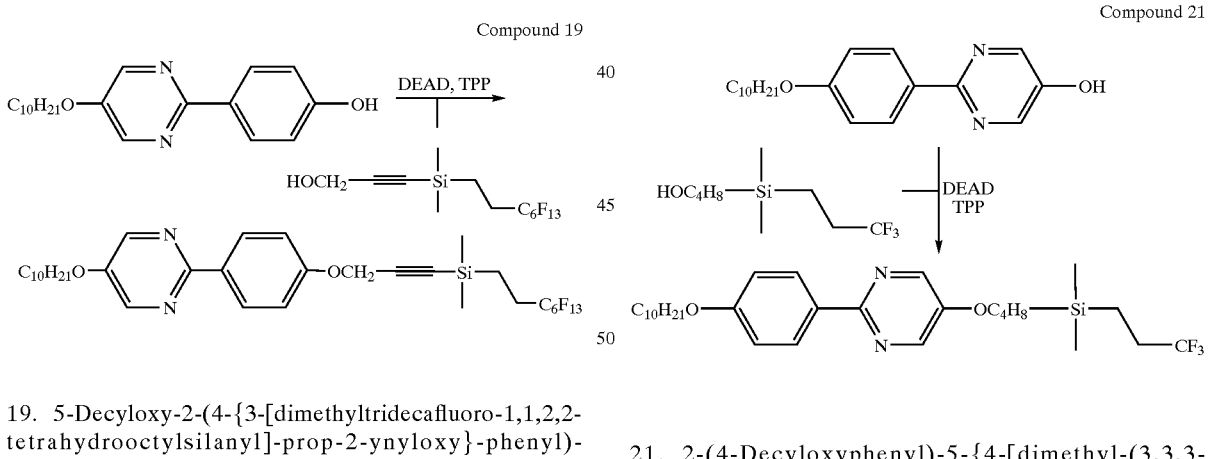

19. 5-Decyloxy-2-(4-{3-[dimethyltridecafluoro-1,1,2,2-tetrahydrooctylsilanyl]-prop-2-ynyloxy}-phenyl)-pyrimidine A solution of DEAD (0.261 g, 1.50 mmol) in diethyl ether (10 ml) was added dropwise to a stirred solution of 4-(5-decyloxypyrimidin-2-yl)phenol (0.492 g, 1.50 mmol), compound 11 (0.690 g, 1.50 mmol) and triphenylphosphine (0.393 g, 1.50 mmol) in diethyl ether (30 ml) and the reaction mixture was stirred at room temperature for 24 h. The solvent was removed in vacuo and the residues purified by column chromatography [silica gel; eluted with hexane/ethyl acetate (4:1), R$_f$: 0.45] to yield a colorless solid, which was recrystallized from ethanol to yield colorless crystals.

Yield: 1.15 g, 1.46 mmol, 97%

Transitions: Cr 107.3 I° C.

20. 5-Decyloxy-2-(4-{3-dimethyltridecafluoro-1,1,2,2-tetrahydrooctyl}-silanyl]-propoxy}-phenyl)-pyrimidine A suspension of compound 19 (0.693 g, 0.90 mmol) and palladium hydroxide on charcoal (31.0 mg, 2.7×10$^{-2}$ mmol) in ethyl acetate and ethanol (120 ml, 2:1) was stirred at room temperature and a pressure of 200 pounds/inch$^2$ under hydrogen for 48 h. The reaction mixture was filtered and the crude product recrystallized from ethanol to yield colorless crystals.

Yield: 0.69 g, 0.89 mmol, 99%

Transitions: Cr 88.1 SmA 102.5 I° C.

21. 2-(4-Decyloxyphenyl)-5-{4-[dimethyl-(3,3,3-trifluoropropyl)-silanyl]-butoxy}-pyrimidine A solution of DEAD (0.348 g, 2.00 mmol) in THF (20 ml) was added dropwise to a stirred solution of 2-(4-decyloxyphenyl)-5-hydroxypyrimidine (0.656 g, 2.0 mmol), compound 12 (0.456 g, 2.0 mmol) and triphenylphosphine (0.524 g, 2.0 mmol) in THF (30 ml) and the reaction mixture stirred at room temperature for 60 h. The solvent was removed in vacuo and the residues purified by column chromatography [silica gel; eluted with hexane/ethyl acetate (4:1) R$_f$: 0.36] to yield a colorless solid, which was recrystallized from ethanol.

Yield: 1.03 g, 1.81 mmol, 96%

Transitions: Cr (30.2 SmC 34.6 N) 39.0 I° C.

Compound 21

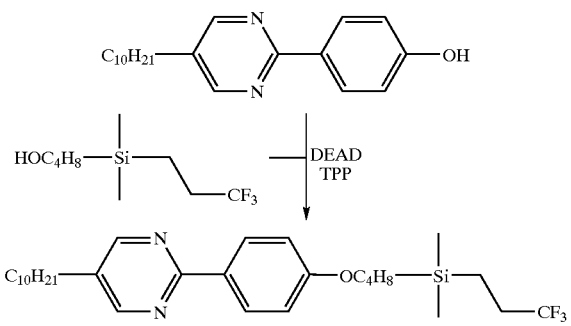

22. 5-Decyl-2-(4-{4-[dimethyl-(3,3,3-trifluoropropyl)-silanyl]-butoxy}-phenyl)-pyrimidine A solution of DEAD (0.348 g, 2.00 mmol) in THF (20 ml) was added dropwise to a stirred solution of 4-(5-decylpyrimidine-2-yl)-phenol (0.624 g, 2.0 mmol), compound 12 (0.456 g, 2.0 mmol) and triphenylphosphine (0.524 g, 2.0 mmol) in THF (30 ml) and the reaction mixture stirred at room temperature for 48 h. The solvent was removed in vacuo and the residues purified by column chromatography [silica gel; eluted with hexane/ethyl acetate (4:1), $R_f$: 0.43] to yield a colorless solid, which was recrystallized from ethanol.

Yield: 0.79 g, 1.51 mmol, 76%

Transitions: SmC 28.9 SmA 35.4 I° C.

Compound 22

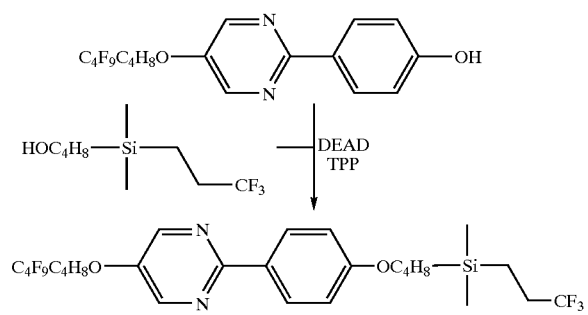

23. 2-(4-{4-[Dimethyl-(3,3,3-trifluoropropyl)-silanyl]-butoxy}-phenyl)-5-(5,5,6,6,7,7,8,8,8-nonafluorooctyloxy)-pyrmidine A solution of DEAD (0.348 g, 2.00 mmol) in THF (20 ml) was added dropwise to a stirred solution of 4-[5-(5,5,6,6,7,7,8,8,8-nonafluorooctyloxy)-pyrimidin-2-yl]-phenol (1.08 g, 2.0 mmol), compound 12 (0.456 g, 2.0 mmol) and triphenylphosphine (0.524 g, 2.0 mmol) in THF (30 ml) and the reaction mixture stirred at room temperature for 48 h. The solvent was removed in vacuo and the residues purified by column chromatography [silica gel, eluted with hexane/ethyl acetate (4:1), $R_f$: 0.15] to yield a colorless solid, which was recrystallized from ethanol.

Yield: 0.63 g, 0.84 mmol, 42%

Transitions: Cr 69.2 I° C.

Compound 23

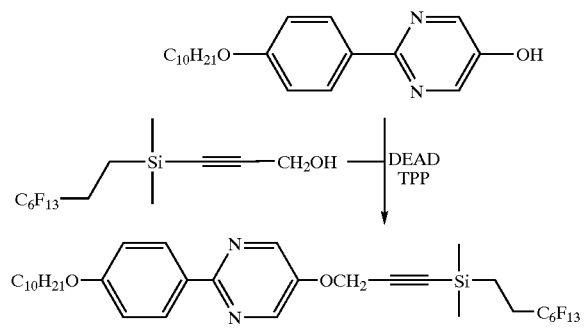

24. 2-(4-Decyloxyphenyl)-5-{[3-dimethyl-(tridecafluoro-1,1,2,2-tetrahydrooctyl)-silanyl]-prop-2-ynyloxy}-pyrimidine A solution of DEAD (0.261 g, 1.50 mmol) in THF (20 ml) was added dropwise to a stirred solution of compound 11 (0.69 g, 1.50 mmol), 2-(4-decyloxyphenl)-5-hydroxypyrimidine (0.492 g, 1.50 mmol) and triphenylphosphine (0.393 g, 1.50 mmol) in THF (50 ml) and the reaction mixture stirred at room temperature for 24 h. The solvent was removed in vacuo and the residues purified by column chromatography [silica gel, eluted with hexane/ethyl acetate (4:1), $R_f$: 0.44] to yield a colorless solid, which was recrystallized from ethanol.

Yield: 0.98 g, 1.27 mmol, 85%

Transitions: Cr 102.7 I° C.

Compound 24

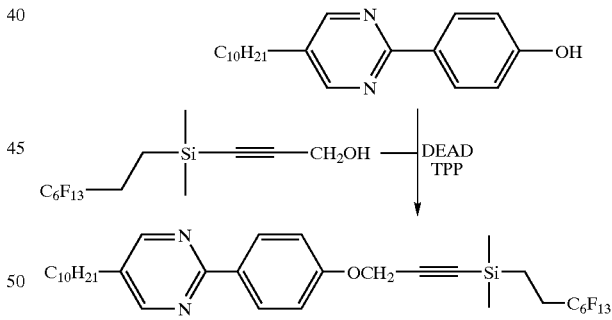

24 5-Decyl-2-(4-{dimethyl-(tridecafluoro-1,1,2,2,-tetrahydrooctyl)-silanyl]-prop-2-ynyloxy}-phenyl)-pyrimidine A solution of DEAD (0.261 g, 1.50 mmol) in THF (20 ml) was added dropwise to a stirred solution of compound 11 (0.69 g, 1.50 mmol), 4-(5-decylpyrimidine-2-yl)-phenol (0.468 g, 1.50 mmol) and triphenylphosphine (0.393 g, 1.50 mmol) in THF (50 ml) and the reaction mixture stirred at room temperature for 24 h. The solvent was removed in vacuo and the residues purified by column chromatography [silica gel, eluted with hexane/ethyl acetate (4:1), Rf: 0.43] to yield a colorless solid, which was recrystallized from ethanol.

Yield: 0.58 g, 0.77 mmol, 51%

Transitions: Cr 76.0 I° C.

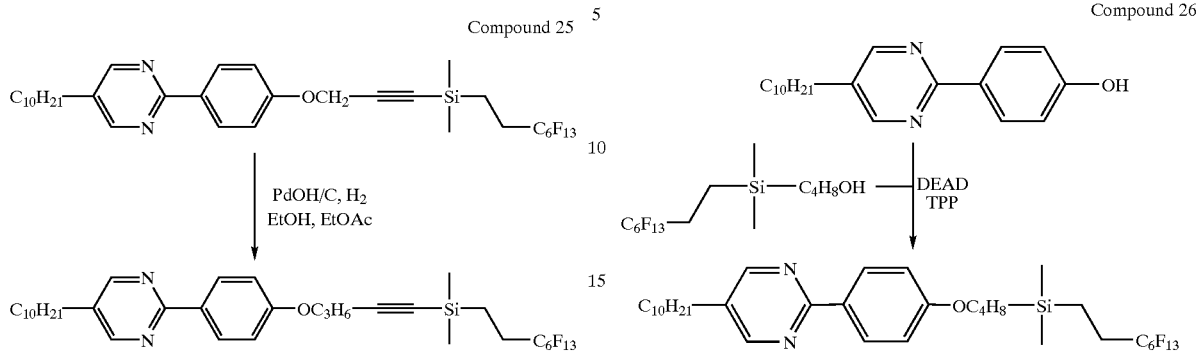

Compound 25

25. 5-Decyl-2-(4-{dimethyl-(tridecafluoro-1,1,2,2,-tetrahydrooctyl)-silanyl]-propoxy}-phenyl)-pyrimidine A suspension of compound 24 (0.58 g, 0.77 mmol) palladium hydroxide on charcoal (26.6 mg, 0.03 mmol) in ethyl acetate and ethanol (160 ml, 2:1) were stirred at room temperature and a pressure of 200 pounds/inch$^2$ under hydrogen for 48 h. The reaction mixture was filtered and the crude product recrystallized from ethanol to yield colorless crystals.

Yield: 0.58 g, 0.77 mmol, 100%

Transitions: Cr 70 SmA 79 I° C.

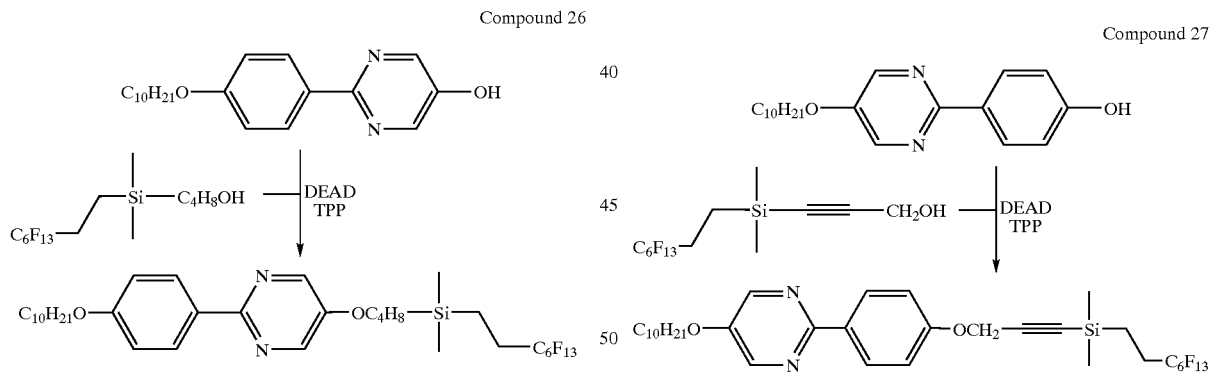

Compound 26

26. 2-(4-Decyloxyphenyl)-5-{4-[dimethyl-(tridecafluoro-1,1,2,2-tetrahydrooctyl)-silanyl]-butoxy}-pyrimidine A solution of DEAD (0.348 g, 2.0 mmol) in THF (20 ml) was added dropwise to a stirred solution of 2-(4-decyloxyphenyl)-5-hydroxypyrimidine (0.656 g, 2.0 mmol), compound 14 (0.956 g, 2.0 mmol) and triphenylphosphine (0.524 g, 2.0 mmol) in THF (40 ml) and the reaction mixture stirred at room temperature for 24 h. The solvent was removed in vacuo and the residues purified by column chromatography [silica gel, eluted with hexane/ethyl acetate (4:1), $R_f$: 0.32] to yield a colorless solid, which was recrystallized from ethanol.

Yield: 1.33 g, 1.68 mmol, 84%

Transitions: Cr 60.6 SmC 70.1° C.

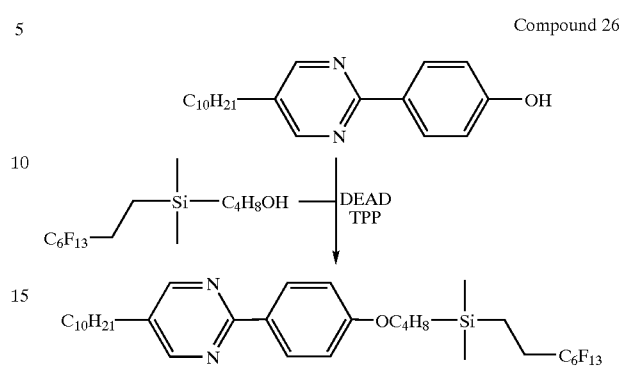

Compound 26

27. 5-Decyl-2-(4-{4-[dimethyl-(tridecafluoro-1,1,2,2-tetrahydrooctyl)-silanyl]-butoxy}-phenyl)-pyrimidine A solution of DEAD (0.348 g, 2.0 mmol) in THF (20 ml) was added dropwise to a stirred solution of compound 14 (0.624 g, 2.0 mmol), 4-(5-decylpyrimidine-2-yl)-phenol (0.936 g, 2.0 mmol) and triphenylphosphine (0.524 g, 2.0 mmol) in THF (40 ml) and the reaction mixture stirred at room temperature for 24 h. The solvent was removed in vacuo and the residues purified by column chromatography [silica gel, eluted with hexane/ethyl acetate (4:1), $R_f$: 0.38] to yield a colorless solid, which was recrystallized from ethanol.

Yield: 1.01 g, 1.31 mmol, 66%

Transitions: Cr 38.2 SmC 52.2 SmA 73.6 I° C.

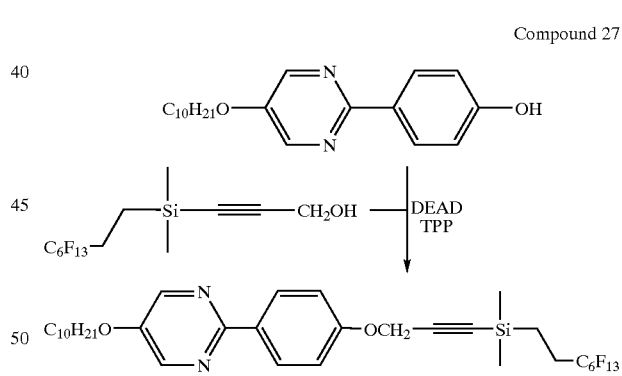

Compound 27

28. 5-Decyl-2-(4-{dimethyl-(tridecafluoro-1,1,2,2,-tetrahydrooctyl)-silanyl]-prop-2-ynyloxy}-phenyl)-pyrimidine A solution of DEAD (0.261 g, 1.50 mmol) in diethyl ether (10 ml) was added dropwise to a stirred solution of 4-(5decyloxypyrimidin-2-yl)-phenol (0.492 g, 1.50 mmol), compound 11 (0.690 g, 1.50 mmol) and triphenylphosphine (0.393 g, 1.50 mmol) in diethyl ether (30 ml) and the reaction mixture stirred at room temperature for 24 h. The solvent was removed in vacuo and the residues purified by column chromatography [silica gel, eluted with hexane/ethyl acetate (4:1), $R_f$: 0.45] to yield a colorless solid, which was recrystallized from ethanol to yield colorless crystals.

Yield: 1.15 g, 1.46 mmol, 97%

Transitions: Cr 107.3 I° C.

Compound 28

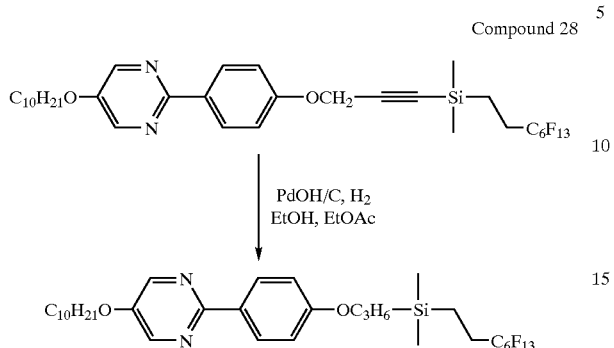

29. 5-Decyloxy-2-(4-{dimethyl-(tridecafluoro-1,1,2,2,-tetrahydrooctyl)-silanyl]-propoxy}-phenyl)-pyrimidine A suspension of compound 27 (0.69 g, 0.90 mmol) and palladium hydroxide on charcoal (0.031 g, $2.7 \times 10^{-5}$ mol) in ethyl acetate and ethanol (120 ml, 2:1) was stirred at room temperature and a pressure of atmospheres of hydrogen for 24 h. The reaction mixture was filtered and the crude product recrystallized from ethanol to yield colorless crystals.

Yield: 0.69 g, 0.89 mmol, 99%

Transitions: Cr 88.1 SmA 102.5 I° C.

Compound 29

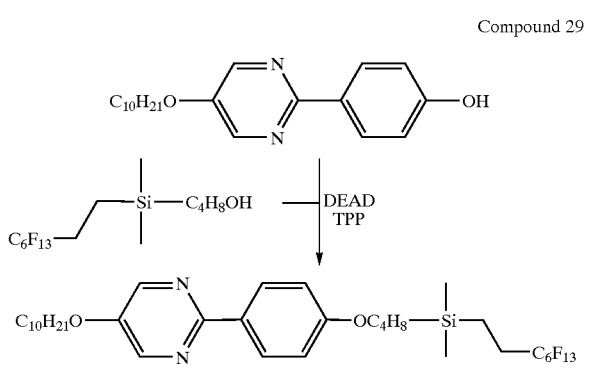

30. 5-Decyloxy-2-(4-{4-[dimethyl-(tridecafluoro-1,1,2,2-tetrahydrooctyl)-silanyl]-butoxy}-phenyl)-pyrimidine A solution of DEAD (0.261 g, 1.50 mmol) in diethyl ether (10 ml) was added dropwise to a stirred solution of 4-(5-decyloxypyrimidin-2-yl)-phenol (0.492 g, 1.50 mmol), compound 14 (0.717 g, 1.50 mmol) and triphenylphosphine (0.393 g, 1.50 mmol) in diethyl ether (30 ml) and the reaction mixture stirred at room temperature for 24 h. The solvent was removed in vacuo and the residues purified by column chromatography [silica gel, hexane/ethyl acetate (4:1), $R_f$: 0.46] to yield a colorless solid, which was recrystallized from ethanol to yield colorless crystals.

Yield: 1.12 g, 1.42 mmol, 95%

Transitions: Cr 41.1 SmC 86.1 SmA 101.3 I° C.

Compound 30

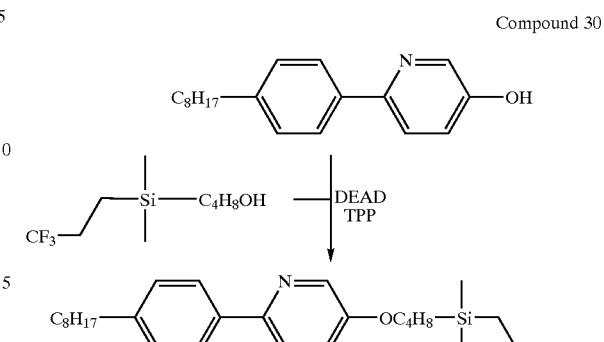

31. 5-{4-[Dimethyl-(3,3,3-trifuoropropyl)-silanyl]-butoxy}-2-(4octylphenyl)-pyridine A solution of DEAD (0.108 g, 0.625 mmol) in THF (10 ml) was added dropwise to a stirred solution of 6-(4-octylphenyl)-pyridin-3-ol (0.141 g, 0.50 mmol), compound 12 (0.125 g, 0.55 mmol) and triphenylphosphine (0.164 g, 0.625 mmol) in THF (10 ml) and the reaction mixture stirred at room temperature for 24 h. The solvent was removed in vacuo and the residues purified by column chromatography [silica gel, hexane/ethyl acetate (4:1)] to yield a colorless oil.

Yield: 0.161 g, 0.327 mmol, 65%

Compound 31

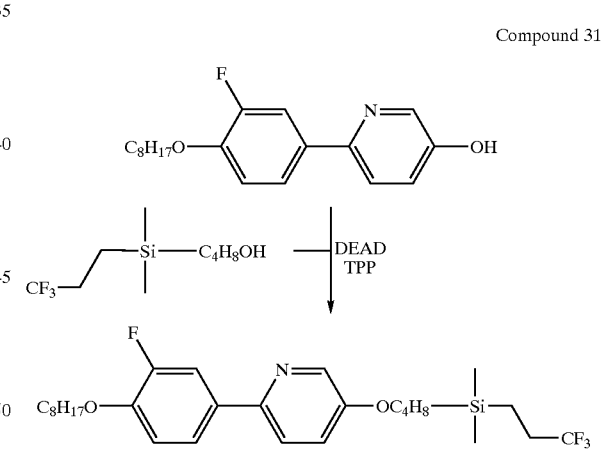

32. 5-{4-[Dimethyl-(3,3,3-trifluoropropyl)-silanyl]-butoxy}-2-(3-fluoro-4-octyloxyphenyl)-pyridine A solution of DEAD (0.108 g, 0.625 mmol) in THF (10 ml) was added dropwise to a stirred solution of 6-(3-fluoro-4-octyloxyphenyl)-pyridin-3-ol (0.150 g, 0.50 mmol), compound 12 (0.125 g, 0.55 mmol) and triphenylphosphine (0.164 g, 0.625 mmol) in THF (10 ml) and the reaction mixture stirred at room temperature for 24 h. The solvent was removed in vacuo and the residues purified by column chromatography [silica gel, hexane/ethyl acetate (4:1)] to yield a colorless solid, which was recrystallized from ethanol.

Yield: 0.128 g, 0.251 mmol, 50%
Transitions:

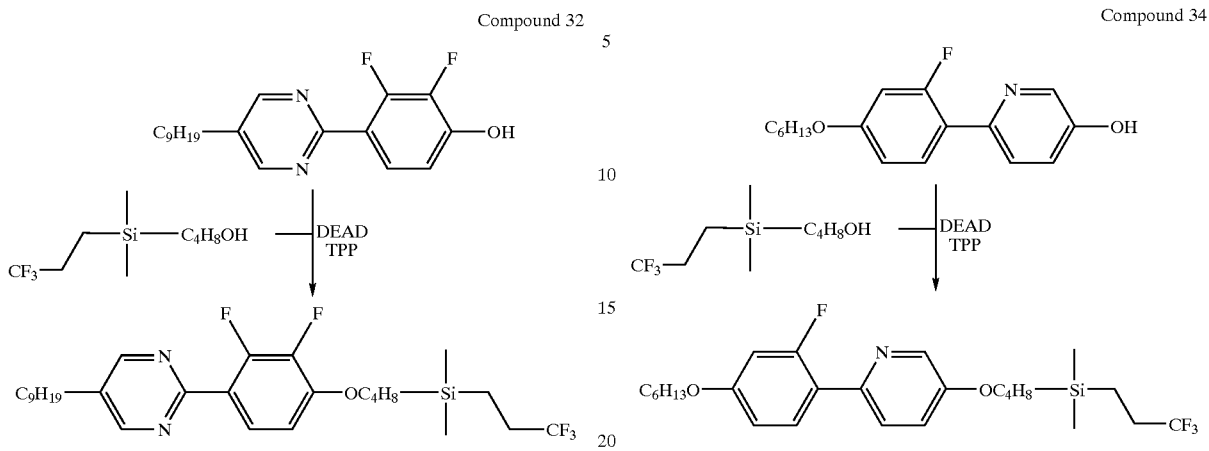

Compound 32

33. 2-(4-{4-[Dimethyl-(3,3,3-trifluoropropyl)-silanyl]-butoxy}-2,3-difluorophenyl)-5-nonylpyrimidine A solution of DEAD (0.087 g, 0.50 mmol) in THF (5 ml) was added dropwise to a stirred solution of 2,3-difluoro-4-(5-nonylpyrimidin-2-yl)phenol (0.132 g, 0.40 mmol), compound 12 (0.091 g, 0.40 mmol) and triphenylphosphine (0.131 g, 0.50 mmol) in THF (10 ml) and the reaction mixture stirred at room temperature for 24 h. The solvent was removed in vacuo and the residues purified by column chromatography [silica gel, hexane/ethyl acetate (9:1)] to yield a colorless solid, which was recrystallized from acetonitrile.

Yield: 0.141 g, 0.251 mmol, 63%
Transitions:

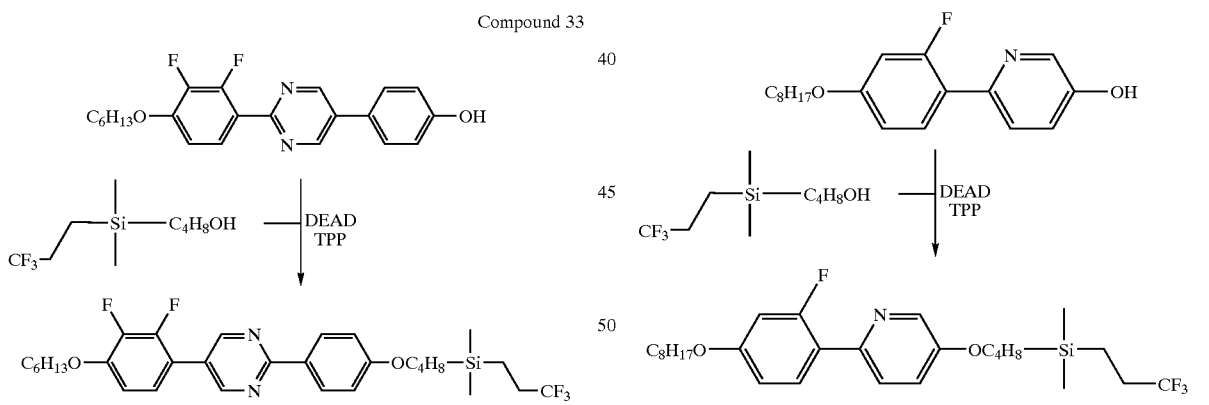

Compound 33

34. 5-(2,3,-Difluoro-4-hexyloxyphenyl)-2-(4-{4-[dimethyl-(3,3,3-trifluoropropyl)-silanyl]-butoxy}-phenyl)-pyrimidine A solution of DEAD (0.087 g, 0.50 mmol) in THF (5 ml) was added dropwise to a stirred solution of 4-[2-(2,3-difluoro-4-hexyloxyphenyl)-pyrimidin-5-yl]-phenol (0.154 g, 0.40 mmol), compound 12 (0.091 g, 0.40 mmol) and triphenylphosphine (0.131 g, 0.50 mmol) in THF (10 ml) and the reaction mixture stirred at room temperature for 24 h. The solvent was removed in vacuo and the residues purified by column chromatography [silica gel, hexane/ethyl acetate (9:1)] to yield a colorless solid, which was recrystallized from acetonitrile.

Yield: 0.104 g, 0.175 mmol, 44%
Transitions:

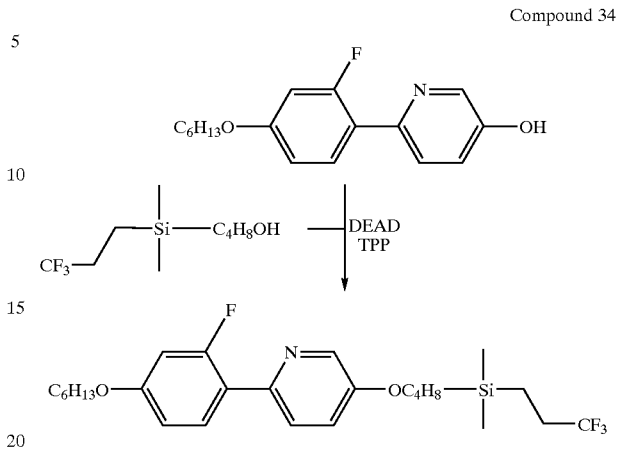

Compound 34

35. 5-{4-[Dimethyl-(3,3,3-trifluoropropyl)-silanyl]-butoxy}-2-(2-fluoro-4-hexyloxyphenyl)-pyridine A solution of DEAD (0.087 g, 0.50 mmol) in THF (5 ml) was added dropwise to a stirred solution of 6-(2-fluoro-4-hexyloxyphenyl)-pyridine-3-ol (0.146 g, 0.40 mmol), compound 12 (0.091 g, 0.40 mmol) and triphenylphosphine (0.131 g, 0.50 mmol) in THF (10 ml) and the reaction mixture stirred at room temperature for 24 h. The solvent was removed in vacuo and the residues purified by column chromatography [silica gel, hexane/ethyl acetate (9:1)] to yield a colorless solid, which was recrystallized from acetonitrile.

Yield: 0.155 g, 0.200 mmol, 50%
Transitions:

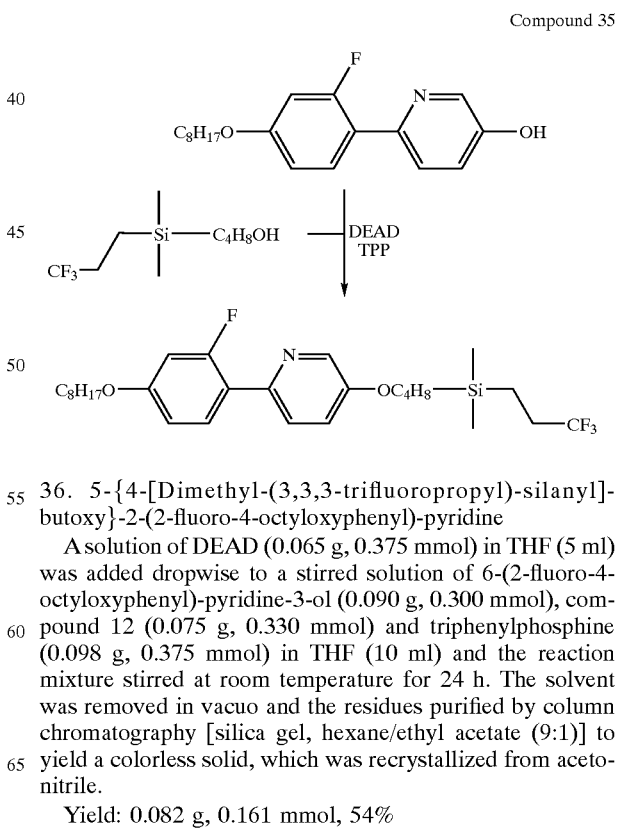

Compound 35

36. 5-{4-[Dimethyl-(3,3,3-trifluoropropyl)-silanyl]-butoxy}-2-(2-fluoro-4-octyloxyphenyl)-pyridine A solution of DEAD (0.065 g, 0.375 mmol) in THF (5 ml) was added dropwise to a stirred solution of 6-(2-fluoro-4-octyloxyphenyl)-pyridine-3-ol (0.090 g, 0.300 mmol), compound 12 (0.075 g, 0.330 mmol) and triphenylphosphine (0.098 g, 0.375 mmol) in THF (10 ml) and the reaction mixture stirred at room temperature for 24 h. The solvent was removed in vacuo and the residues purified by column chromatography [silica gel, hexane/ethyl acetate (9:1)] to yield a colorless solid, which was recrystallized from acetonitrile.

Yield: 0.082 g, 0.161 mmol, 54%

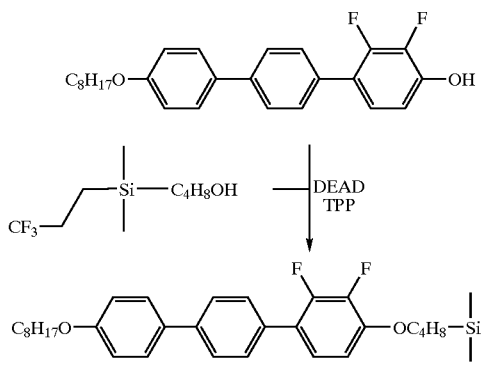

Compound 36

37. 4-(2",3"-Difluoro-4-octyloxy-[1,1':4',1"]terphenyl-4"-yloxy)-butyl]-deimethyl-(3,3,3-trifluoropropyl)-silane A solution of DEAD (43.5 mg, 0.250 mmol) in THF (5 ml) was added dropwise to a stirred solution of 2",3"-difluoro-4-octyloxy-[1,1':4',1"]terphenyl-4"-ol (82.0 mg, 0.200 mmol), compound 12 (45.6 mg, 0.200 mmol) and triphenylphosphine (65.2 mg, 0.250 mmol) in THF (10 ml) and the reaction mixture stirred at room temperature for 24 h. The solvent was removed in vacuo and the residues purified by column chromatography [silica gel, hexane/ethyl acetate (33:1)] to yield a colorless solid, which was recrystallized from acetonitrile.

Yield: 67.0 mg, 0.108 mmol, 54%

Transitions:

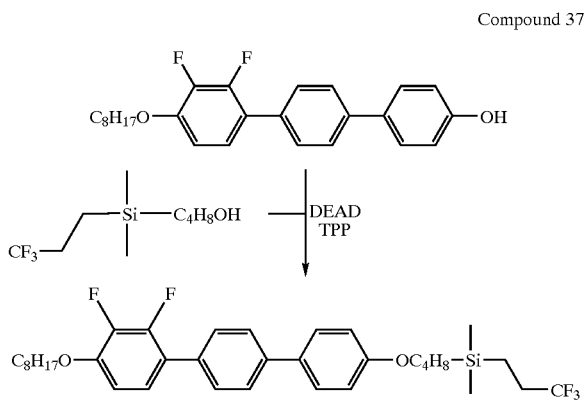

Compound 37

38. 4-(2,3-Difluoro-4-octyloxy-[1,1':4',1"]terphenyl-4"-yloxy)-butyl]-dimethyl(3,3,3-trifluoropropyl)-silane A solution of DEAD (26.10 mg, 0.150 mmol) in THF (5 ml) was added dropwise to a stirred solution of 2,3-difluoro-4-octyloxy-[1,1':4',1"]terphenyl-4"-ol (49.2 mg, 0.120 mmol, compound 12 (27.36 mg, 0.120 mmol) and triphenylphosphine (39.12 mg, 0.150 mmol in THF (10 ml) and the reaction mixture stirred at room temperature for 24 h. The solvent was removed in vacuo and the residues purified by column chromatography [silica gel, hexane/ethyl acetate (33:1)] to yield a colorless solid, which was recrystallized from acetonitrile.

Yield: 51.0 mg, 0.083 mmol, 69%

Transitions:

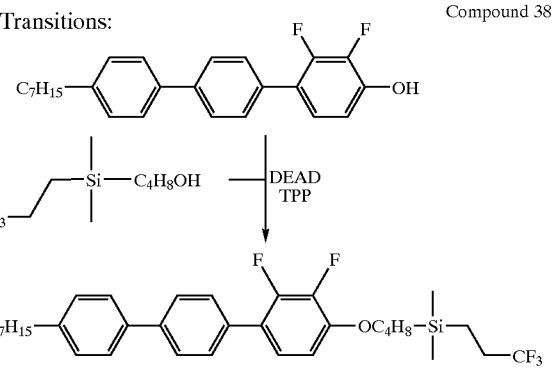

Compound 38

39. 4-(2",3"-Difluoro-4-heptyl-[1,1':4',1"]terphenyl-4"-yloxy)-butyl]-dimethyl-(3,3,3-trifluoropropyl)-silane A solution of DEAD (65.00 mg, 0.375 mmol) in THF (5 ml) was added dropwise to a stirred solution of 2",3"-difluoro-4-heptyl-[1,1':4',1"]terphenyl-4"-ol (0.114 g, 0.30 mol), compound 12 (0.075 g 0.330 mmol) and triphenylphosphine (0.098 g, 0.375 mmol) in THF (10 ml) and the reaction mixture stirred at room temperature for 24 h. The solvent was removed in vacuo and the residues purified by column chromatography [silica gel, hexane/ethyl acetate (33:1)] to yield a colorless solid, which was recrystallized from acetonitrile.

Yield: 39.0 mg, 0.067 mmol, 22%

Transitions:

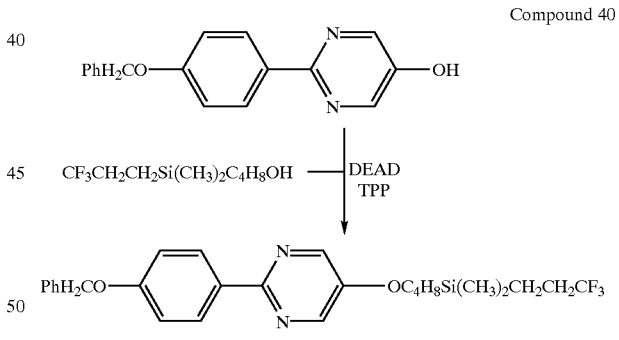

Compound 40

40. 2-(4-Benzyloxy-phenyl)-5-{4-[dimethyl-(3,3,3-trifluoropropyl)-silanyl]-butoxy}-pyrimidine A solution of DEAD (21.80 mg, 1.00 mmol) in THF (5 ml) was added dropwise to a stirred solution of 2-(4-benzyloxy-phenyl)-pyrimidin-5-ol (0.284 g, 1.00 mmol), compound 12 (0.250 g 1.10 mmol) and triphenylphosphine (0.218 g, 1.250 mmol) in THF (20 ml) and the reaction mixture stirred at room temperature for 24 h. The solvent was removed in vacuo and the residues purified by column chromatography [silica gel, hexane/ethyl acetate (33:1)] to yield a colorless solid, which was recrystallized from acetonitrile.

Yield: 0.340 g, 0.069 mmol, 69%
Transitions:

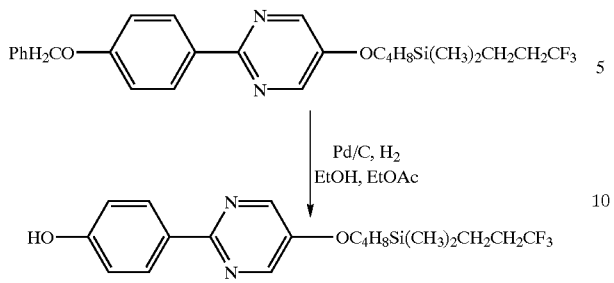
Compound 41

41. 4-(5-{4-[Dimethyl-(3,3,3-trifluoropropyl)-silanyl]-butoxy}-pyrimidin-2-yl)-phenol A suspension of compound 40 (0.321 g, 0.658 mmol), palladium on charcoal (0.0343 g, 0.033 mmol) in ethanol/ethyl acetate (6.5 ml, 1:2) was stirred under an atmosphere of hydrogen at room temperature for 24 hours. The reaction mixture was filtered (celite), the solvent removed in vacuo and the residues recrystallized from acetonitrile to yield colorless crystals.

Yield: 0.249 g, 0.626 mmol, 95%

42. Trans-4-Pentyl-cyclohexanecarboxylic acid 4-(5-{4-[dimethyl-(3,3,3-trifluoro-propyl)-silanyl]-butoxy}-pyrimidin-2-yl)-phenyl ester A solution of diisopropyl-carbodiimide (DIC) (0.0454 g, 0.360 mmol) in ethyl acetate (3.0 ml) was added dropwise to a stirred solution of compound 41 (0.119 g, 0.300 mmol), trans-4-pentylcyclohexanecarboxlic acid (0.0713 g, 0.369 mmol) and dimethylaminopyridine (DMAP) (3.66 mg, 0.03 mmol) in ethyl acetate (3.0 ml). The reaction mixture was stirred at room temperature for 24 h, the solvent removed in vacuo and the residues purified by column chromatography [silica gel, eluted with hexane/ethyl acetate (4:1)] to give a colorless solid, which recrystallized acetonitrile to yield colorless crystals.

Yield: 0.132 g, 0.228 mmol, 76%

Transitions:

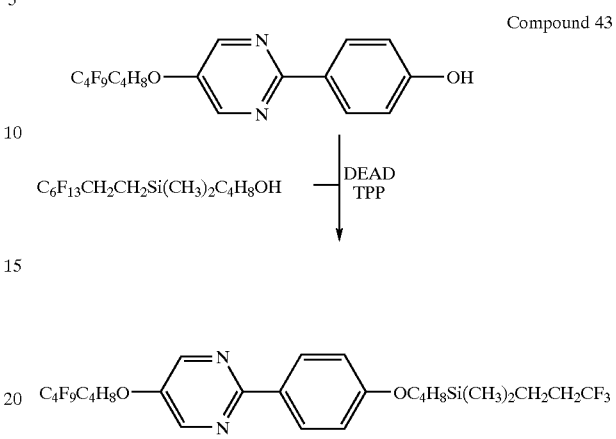
Compound 43

Compound 42

43. 2-(4-{4-[Dimethyl-(3,3,4,4,5,5,6,6,7,7,8,8,8-tridecafluoro-octyl)-silanyl]-butoxy}-phenyl)-5-(5,5,6,6,7,7,8,8,8-nonafluoro-octyloxy)-pyrimidine A solution of DEAD (0.480 g 1.25 mmol) in THF (5 ml) was added dropwise to a stirred solution of 4-[5-(5,5,6,6,7,7,8,8,8-nonafluorooctyloxy)-pyrimidin-2-yl]-phenol (0.462 g, 1.00 mmol), compound 14 (0.478 g, 1.000 mmol) and triphenylphosphine (0.328 g, 1.250 mmol) in THF (10 ml) and the reaction mixture stirred at room temperature for 24 h. The solvent was removed in vacuo and the residues purified by column chromatography [silica gel, hexane/ethyl acetate (9:1)] to yield a colorless solid, which was recrystallized from acetonitrile.

Yield: 0.415 g, 0.450 mmol, 45%

Transitions:

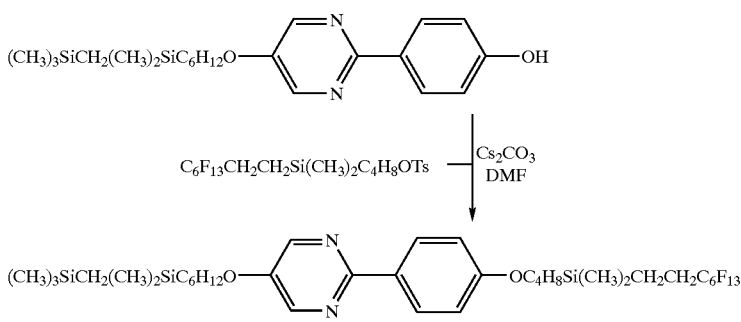

Compound 44

44. 2-(4-{4-[Dimethyl-(3,3,4,4,5,5,6,6,7,7,8,8,8-tridecafluoro-octyl)-silanyl]-butoxy}-phenyl)-5-[6-(dimethyltrimethylsilanylmethyl-silanyl)-hexyloxy]-pyrimidine A suspension of 4-{5-[6-(dimethyltrimethylsilanylmethyl-silanyl)-hexyloxy]-pyrimidin-2-yl}-phenol (0.083 g, 0.200 mmol), toluene-4-sulfonic acid 4-[dimethyl-(3,3,4,4,5,5,6,6,7,7,8,8,8-tridecafluoro-octyl)-silanyl]-butyl ester (0.126 g, 0.200 mmol) and cesium carbonate (0.078 g, 0.24 mmol) in DMF (10 ml) was stirred at room temperature for 24 h. The reaction mixture was washed with water and the organic layer extracted into ethyl acetatelhexane (3×20 ml, 1:1). The combine extracts were washed with brine, dried (MgSO$_4$) and the solvent removed in vacuo. The residues were purified by column chromatography [silica gel, hexane/ethyl acetate (9:1)] to yield a colorless solid, which was recrystallized from acetonitrile.

Yield: 0.122 g, 0.139 mmol, 70%

Transitions:

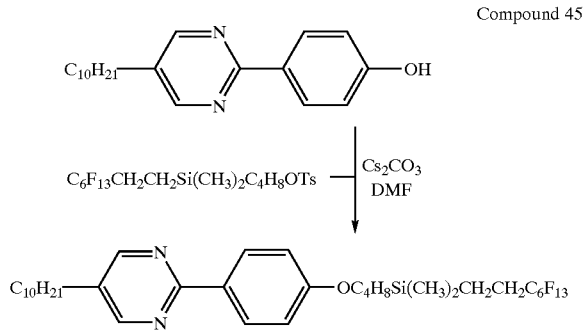

Compound 45

45. 5-Decyl-2-(4-{4-[dimethyl-(3,3,4,4,5,5,6,6,7,7,8,8,8-tridecafluoro-octyl)-silanyl]-butoxy}-phenyl)-pyrimidine A suspension of 4-(5-decyl-pyrimidin-2-yl)-phenol (3.744 g, 13.00 mmol), toluene-4-sulfonic acid 4-[dimethyl-(3,3,4,4,5,5,6,6,7,7,8,8,8-tridecafluoro-octyl)-silanyl]-butyl ester (7.58 g, 13.00 mmol) and cesium carbonate (4.69 g, 14.4 mmol) in DMF (35 ml) was stirred at room temperature for 24 h. The reaction mixture was washed with water and the organic layer extracted into ethyl acetate/hexane (3×20 ml, 1:1). The combine extracts were washed with brine, dried (MgSO$_4$) and the solvent removed in vacuo. The residues were purified by column chromatography [silica gel, hexane/ethyl acetate (9:1)] to yield a colorless solid, which was recrystallized from acetonitrile.

Yield: 4.16 g, 5.39 mmol, 41%

Transitions:

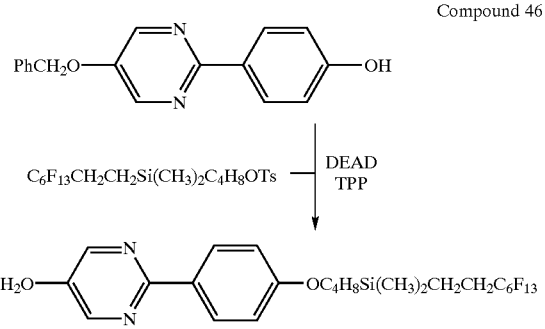

Compound 46

46. 5-Benzyloxy-2-(4-{4-[dimethyl -(3,3,4,4,5,5,6,6,7,7,8,8,8-tridecafluoro-octyl)-silanyl]-butoxy}-phenyl)-pyrimidine A solution of DEAD (1.04 g 6.00 mmol) in THF (5 ml) was added dropwise to a stirred solution of 4-(5-benzyloxy-pyrimidin-2-yl)-phenol (1.39 g, 5.00 mmol), compound 14 (2.39 g, 5.00 mmol) and triphenylphosphine (1.57 g, 6.00 mmol) in THF (20 ml) and the reaction mixture stirred at room temperature for 24 h. The solvent was removed in vacuo and the residues purified by column chromatography [silica gel, hexane/ethyl acetate (9:1)] to yield a colorless solid, which was recrystallized from acetonitrile.

Yield: 2.25 g, 3.05 mmol, 61%

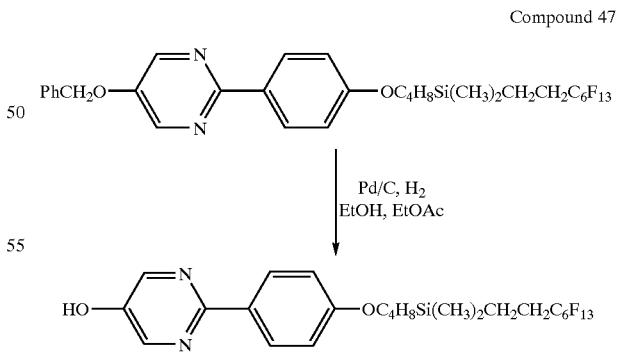

Compound 47

47. 2-(4-{4-[Dimethyl-(3,3,4,4,5,5,6,6,7,7,8,8,8-tridecafluoro-octyl)-silanyl]-butoxy}-phenyl)-pyrimidin-5-ol A suspension of compound 46 (2.232 g, 3.02 mmol), palladium on charcoal (0.095 g, 0.091 mmol) in ethanol/ethyl acetate (6.5 ml, 1:2) was stirred under an atmosphere of hydrogen at room temperature for 24 hours. The reaction mixture was filtered (celite), the solvent removed in vacuo and the residues recrystallized from acetonitrile to yield colorless crystals.

Yield: 1.752 g, 2.70 mmol, 89%

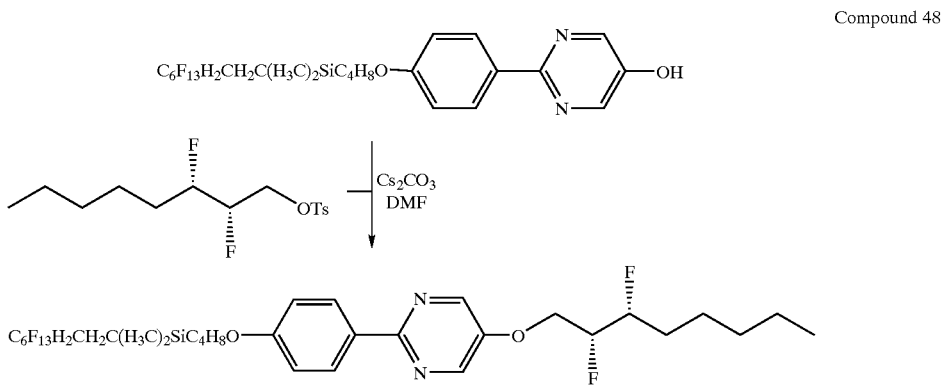

Compound 48

48. (S,S)-5-(2,3-Difluorooctyloxy)-2-(4-{4-[dimethyl-(3,3,4,4,5,5,6,6,7,7,8,8,8-tridecafluoro-octyl)-silanyl]-butoxy}-phenyl)-pyrimidine A suspension of compound 47 (0.162 g, 0.250 mmol), toluene-4-sulfonic acid 2,3-difluoro-octyl ester (0.080 g, 0.250 mmol) and cesium carbonate (0.098 g, 0.300 mmol) in DMF 5.0 ml) was stirred at room temperature for 24 h. The reaction mixture was washed with water and the organic layer extracted into ethyl acetate/hexane (3×20 ml, 1:1). The combine extracts were washed with brine, dried (MgSO$_4$) and the solvent removed in vacuo. The residues were purified by column chromatography [silica gel, hexane/ethyl acetate (9:1)] to yield a colorless solid, which was recrystallized from acetonitrile.

Yield: 0.131 g, 0.165 mmol, 66%

Transitions:

Compound 49

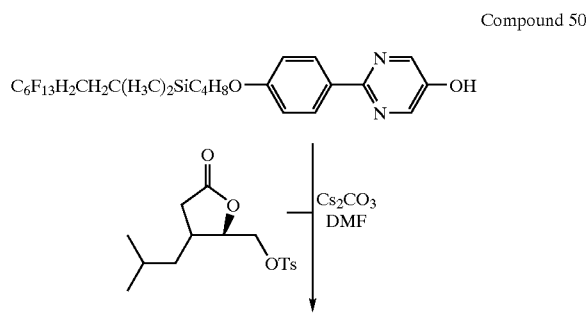

49. Trans-4-pentylcyclohexanecarboxylic acid 2-(4-{4-[dimethyl-(3,3,4,4,5,5,6,6,7,7,8,8,8-tridecafluoro-octyl)-silanyl]-butoxy}-phenyl)-pyrimidin-5-yl ester A solution of DIC (0.061 g, 0.48 mmol) in ethyl acetate (3.0 ml) was added dropwise to a stirred solution of compound 48 (0.261 g, 0.400 mmol), trans-4-pentylcyclohexanecarboxlic acid (0.095 g, 0.480 mmol) and DMAP (4.90 mg, 0.04 mmol) in ethyl acetate (3.0 ml). The reaction mixture was stirred at room temperature for 24 h, the solvent removed in vacuo and the residues purified by column chromatography [silica gel, eluted with hexane/ethyl acetate (4:1)] to give a colorless solid, which recrystallized acetonitrile to yield colorless crystals.

Yield: 0.212 g, 0.256 mmol, 64%

Transitions:

Compound 50

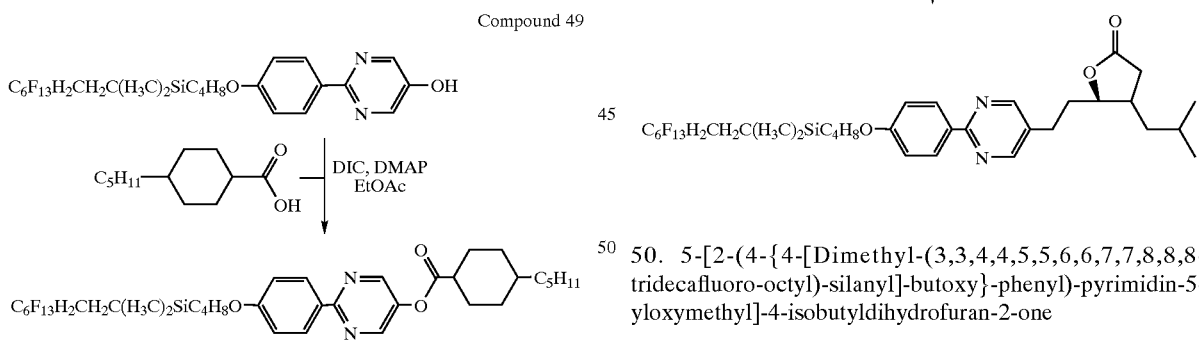

50. 5-[2-(4-{4-[Dimethyl-(3,3,4,4,5,5,6,6,7,7,8,8,8-tridecafluoro-octyl)-silanyl]-butoxy}-phenyl)-pyrimidin-5-yloxymethyl]-4-isobutyldihydrofuran-2-one A suspension of compound 47 (0.162 g, 0.250 mmol), toluene-4-sulfonic acid 3-isobutyl-5-oxo-tetrahydro-furan-2-ylmethyl ester (0.0815 g, 0.250 mmol) and cesium carbonate (0.098 g, 0.300 mmol) in DMF 5.0 ml) was stirred at room temperature for 24 h. The reaction mixture was washed with water and the organic layer extracted into ethyl acetate/hexane (3×20 ml, 1:1). The combine extracts were washed with brine, dried (MgSO$_4$) and the solvent removed in vacuo. The residues were purified by column chromatography [silica gel, hexane/ethyl acetate (9:1)] to yield a colorless solid, which was recrystallized from acetonitrile.

Yield: 0.045 g, 0.056 mmol, 22%

Transitions:

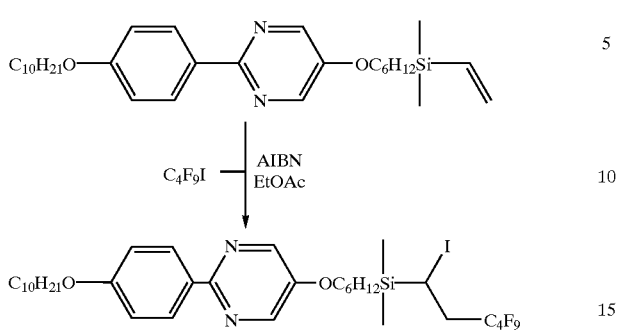

Compound 51

51. 2-(4-Decyloxy-phenyl)-5-{6-[dimethyl-(3,3,4,4,5,5,6,6,6-nonafluoro-1-iodo-hexyl)-silanyl]-hexyloxy}-pyrimidine A solution of 2-(4-dcyloxy-phenyl)-5-[6-(dimethyl-vinyl-silanyl)-hexyloxy]-pyrimidine (1.00 g, 2.02 mmol), 1-iodoperfluorobutane (0.698 g, 2.02 mmol) and AIBN (5.0 mg, 0.03 mmol) were dissolved in ethyl acetate under an atmosphere of dry nitrogen and heated in a sealed vessel at 70° C. for 24 h. The reaction mixture was cooled to room temperature, the solvent removed in vacuo and the residues purified by column chromatography [40 g silica gel, eluted with hexane/ethyl acetate (19:1)] to yield a room temperature SmC.

Yield: 0.98 g, 1.16 mmol, 57%
Transitions: SmC 57.7 I° C.

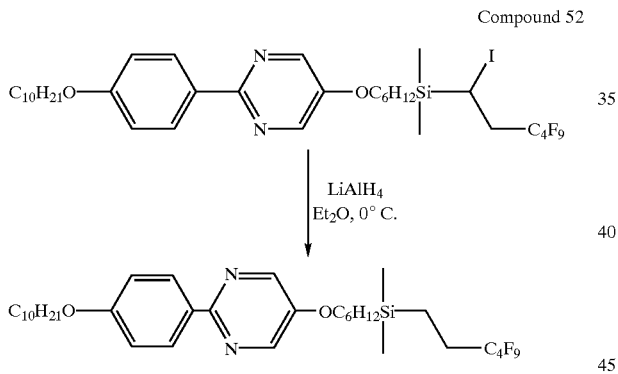

Compound 52

52. 2-(4-Decyloxy-phenyl)-5-{6-[dimethyl-(3,3,4,4,5,5,6,6,6-nonafluoro-hexyl)-silanyl]-hexyloxy}-pyrimidine A solution of compound 51 (0.89 g, 1.06 mmol) in THF (20 ml) was added dropwise to a stirred suspension of lithium aluminiumhydride (80 mg, 2.11 mmol) in THF (20 ml) under an atmosphere of dry nitrogen. The reaction mixture was stirred at room temperature overnight, heated to reflux for 1 h, cooled, washed with water and the organic layer extracted into ethyl acetate/hexane (3 times). The combined organic extracts were washed with brine, dried ($MgSO_4$), the solvent removed in vacuo and the residues purified by column chromatography [40 g silica gel eluted with hexane/ethyl acetate (9:1)] to yield a colorless solid, which was recrystallized from ethanol.

Yield: 0.52 g, 0.73 mmol, 69%
Transitions: Cr 33.9 SmC 73.0 I° C.

Those of ordinary skill in the art will appreciate that compounds, mixtures, methods of synthesis or purification and method of assessing properties of compounds and mixtures other than those specifically described herein can be applied to the practice of this invention. All art-known equivalents of the compounds, mixtures and methods specifically described are encompassed by this invention. All references cited herein are incorporated in their entirety by reference herein.

We claim:

1. A liquid crystal composition comprising one or more compounds of formula:

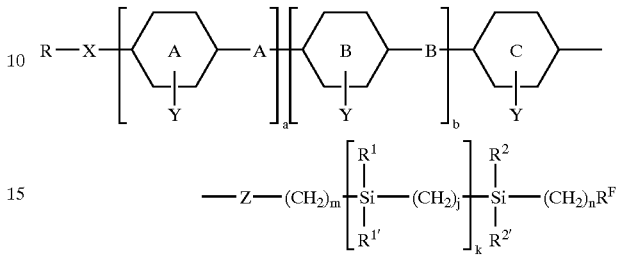

a and b can be 1 or 0; k is 0 or an integer ranging from 1–10;

m and n are integers ranging from 1 to about 20;

j is 0 or an integer ranging from 1 to 20, n+m+k(j) ranges from about 5 to about 20;

one or more non-neighboring carbons in the —($CH_2$)m— group or the —($CH_2$)n— group of the silane tail can be replaced with a double bond, a triple bond or an oxygen;

A and B, independently are linker groups selected from the group consisting of a single bond, —COO—, —OOC—, —$CH_2$—$CH_2$—, —$OCH_2$—, —$CH_2$—O—, —CH=CH—, —CH=CH—CH=CH— and —C≡C—;

X and Z, independently, are —O— or a single bond;

Y indicates optional substitution on the core ring and can represent up to four substituents when the rings are aromatic and up to 10 substituents when the rings are alicyclic, substituents are selected from halides, CN, $NO_2$, alkyl, or alkoxy;

R is an alkyl or alkenyl group having from 3 to about 20 carbons atoms in which one or more of the non-neighboring carbons can be replaced with an oxygen, or in which one or more of the carbons is substituted with one or more halogens R can be chiral racemic, chiral nonracemic or achiral;

$R^1$, $R^{1'}$, $R^2$ and $R^{2'}$ are alkyl groups or perfluorinated alkyl groups having form 1 to 6 carbon atoms;

$R^F$ is a perfluorinated alkyl group having from 1 to about 10 carbon atoms; and Core rings A, B and C can be aromatic rings or alicyclic rings wherein one or two of the CH or $CH_2$ groups of the ring can be replaced with a nitrogen, sulfur or oxygen or a C=O group.

2. The LC composition of claim 1 wherein the core is phenylpyrimidine, biphenyl, phenyl benzoate or terphenyl.

3. The LC composition of claim 1 wherein $R^F$ is $CF_3$, $C_4F_9$ or $C_6F_{13}$.

4. The LC composition of claim 1 wherein n=2.

5. The LC composition of claim 1 wherein $R^1$, $R^{1'}$, $R^2$ and $R^{2'}$ are all methyl groups.

6. The LC composition of claim 1 wherein k is 0.

7. The LC composition of claim 1 wherein Z is oxygen.

8. The LC composition of claim 1 wherein R is alkyl.

9. A liquid crystal composition comprising one or more compounds of formula:

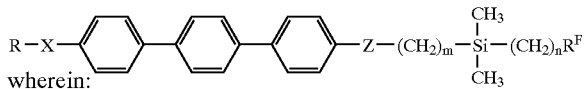

wherein:
  m and n are integers ranging from 1 to about 20;
  n+m ranges from about 5 to about 20;
  one or more non-neighboring carbons in the —(CH$_2$)m— group or the —(CH$_2$)n—group of the silane tail can be replaced with a double bond, a triple bond or an oxygen;
  X and Z, independently, are —O— or a single bond;
  R is an alkyl or alkenyl group having from 3 to about 20 carbons atoms in which one or more of the non-neighboring carbons can be replaced with an oxygen, or in which one or more of the carbons is substituted with one or more halogens R can be chiral racemic, chiral nonracemic or achiral;
  $R^F$ is a perfluorinated alkyl group having from 1 to about 10 carbon atoms.

10. The LC composition of claim 9 where n is 1 or 2.
11. The LC composition of claim 9 where n is 1 or 2.
12. The LC composition of claim 1 where RX is a chiral nonracemic tail.
13. The LC composition of claim 12 wherein k is 0 and $R^2$ and $R^{2'}$ are all methyl groups.
14. The LC composition of claim 1 which exhibits a smectic C phase.
15. The LC composition of claim 14 which further exhibits a smectic A phase.
16. The LC composition of claim 15 which further exhibits a nematic phase.
17. The LC composition of claim 14 wherein the smectic C phase has a temperature range of 50° C. or more.
18. The LC composition of claim 1 which has a freezing point less than or equal to −60° C.
19. The LC composition of claim 1 which has a freezing point 10° C. or more lower than its melting point.
20. The LC composition of claim 1 further comprising one or more compounds of formula:

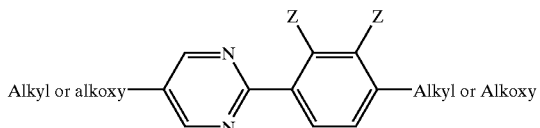

where Z is F or H and the alkyl or alkoxy group has from 5 to 12 carbon atoms.

21. The LC composition of claim 1 further comprising one or more compounds of formula:

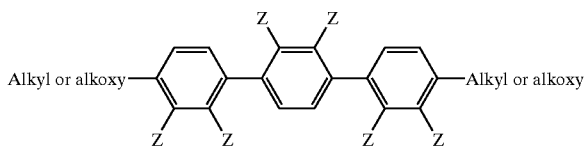

where Z is F or H and the alkyl or alkoxy group has from 5 to 12 carbon atoms.

22. The LC composition of claim 1 further comprising one or more compounds of formulas:

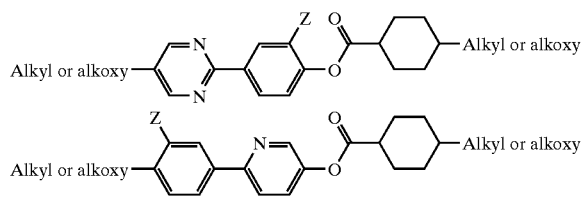

where Z is F or H and the alkyl or alkoxy group has from 5 to 12 carbon atoms.

23. The LC composition of claim 1 further comprising one or more compounds of formulas:

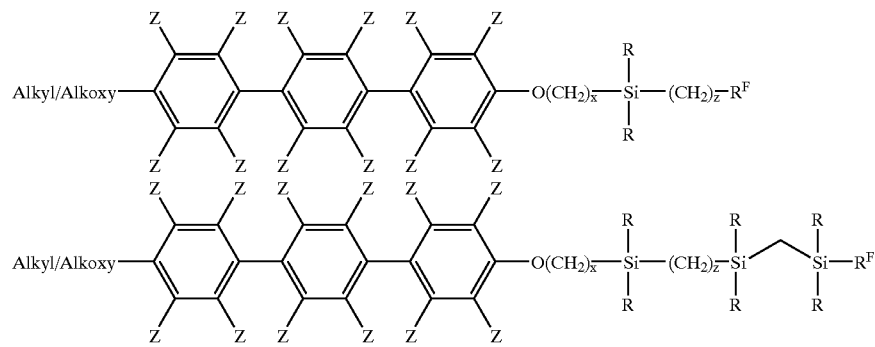

where Z is F or H, x and z range from 1 to 12 and x+z is 5 to 12, $R^F$ is a perfluoroalkyl group having from 1 to 8 carbon atoms, R are alkyl groups having 1 to 6 carbon atoms and the alkyl or alkoxy groups have from 5 to 12 carbon atoms.

24. The LC composition of claim 1 further comprising one or more compounds of formulas:

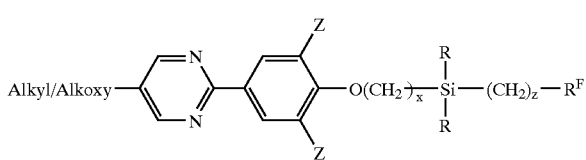

-continued

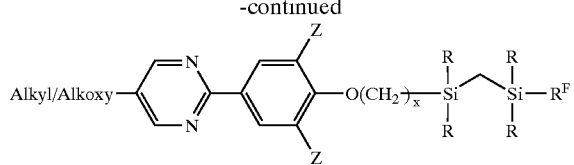

wherein x and z are integers ranging from 1 to 12, R are alkyl groups having from 1 to 6 carbon atoms; $R^F$ is a perfluoroalkyl group having from 1 to 8 carbon atoms; Z is H or a F; and the alkyl or alkoxy groups are those that have 5 to 12 carbon atoms.

25. The LC composition of claim 1 further comprising one or more compounds of formulas:

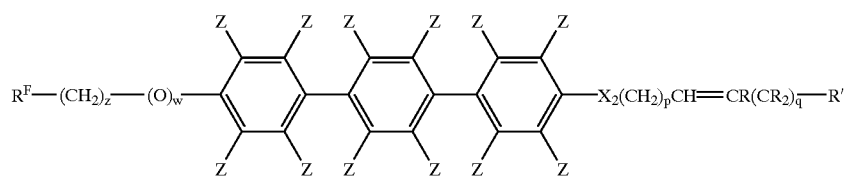

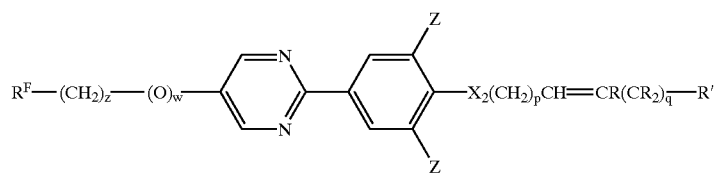

wherein p is an integer ranging from 1 to 20, q is 0 or an integer ranging from 1 to 20, w is 0 or 1; R are alkyl groups having from 1 to 6 carbon atoms; R' is an alkyl group having from 5 to 20 carbon atoms; $R^F$ is a perfluoroalkyl group having from 1 to 8 carbon atoms; and Z is H or a F.

26. The LC composition of claim 1 further comprising one or more compounds of formulas:

wherein the alkyl or alkoxy groups are those having from 5 to 12 carbon atoms.

27. The LC composition of claim 1 wherein R is a chiral racemic or achiral tail and which further comprising one or more compounds of formula:

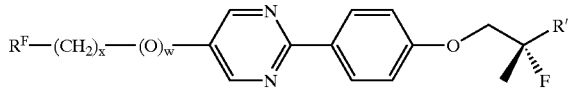

wherein x is an integer ranging from 1 to 20, w is 0 or 1; R' is an alkyl or alkenyl group having from 5 to 20 carbon atoms; and $R^F$ is a perfluoroalkyl group having from 1 to 8 carbon atoms.

28. The LC composition of claim 1 wherein R is a chiral racemic or achiral tail and which further comprising one or more compounds of formula:

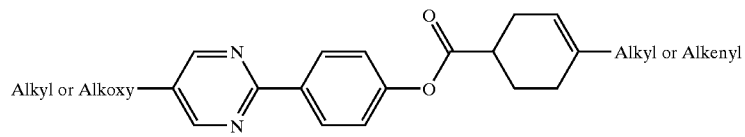

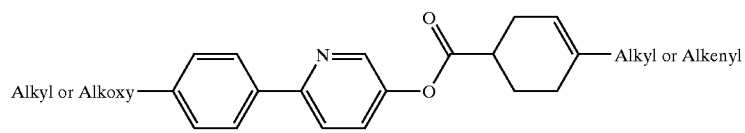

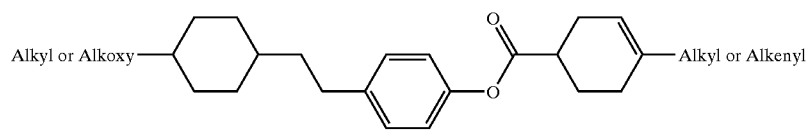

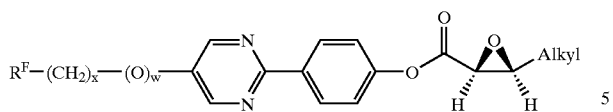

wherein x is an integer ranging from 1 to 20, w is 0 or 1; $R^F$ is a perfluoroalkyl group having from 1 to 8 carbon atoms and the alkyl group has from 3 to 10 carbon atoms.

29. An LC composition of claim 1 further comprising one or more compounds of formula:

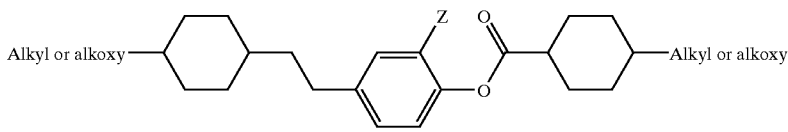

where the alkyl or alkoxy groups have from 5 to 12 carbon atoms and Z is H or F.

30. A LC device which comprises an aligned layer of an LC composition of claim 1.

31. The device of claim 30 which is an SSFLC device.

32. A display comprising the device of claim 31.

33. A compound having the formula:

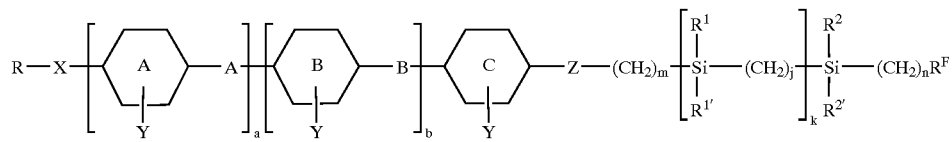

wherein:

a and b can be 1 or 0; k is 0 or an integer ranging from 1–10;

m and n are integers ranging from 1 to about 20;

j is 0 or an integer ranging from 1 to 20, n+m+k(j) ranges from about 5 to about 20;

one or more non-neighboring carbons in the —(CH$_2$)m— group or the —(CH$_2$)n— group of the silane tail can be replaced with a double bond, a triple bond or an oxygen;

A and B, independently are linker groups selected from the group consisting of a single bond, —COO—, —OOC—, —CH$_2$—CH$_2$—, —OCH$_2$—, —CH$_2$—O—, —CH=CH—, —CH=CH—CH=CH— and —C≡C—;

X and Z, independently, are —O— or a single bond;

Y indicates optional substitution on the core ring and can represent up to four substituents when the rings are aromatic and up to 10 substituents when the rings are alicyclic, substituents are selected from halides, CN, NO$_2$, alkyl, or alkoxy;

R is an alkyl or alkenyl group having from 3 to about 20 carbons atoms in which one or more of the non-neighboring carbons can be replaced with an oxygen, or in which one or more of the carbons is substituted with one or more halogens R can be chiral racemic, chiral nonracemic or achiral;

$R^1, R^{1'}, R^2$ and $R^{2'}$ are alkyl groups or perfluorinated alkyl groups having form 1 to 6 carbon atoms;

$R^F$ is a perfluorinated alkyl group having from 1 to about 10 carbon atoms; and Core rings A, B and C can be aromatic rings or alicyclic rings wherein one or two of the CH or CH$_2$ groups of the ring can be replaced with a nitrogen, sulfur or oxygen or a C=O group.

34. The compound of claim 33 wherein the core is phenylpyrimidine, biphenyl, phenyl benzoate or terphenyl.

35. The compound of claim 34 wherein n=2.

36. The compound of claim 34 wherein $R^1, R^{1'}, R^2$ and $R^{2'}$ are all methyl groups.

37. The compound of claim 33 wherein k is 0.

38. A compound having the formula:

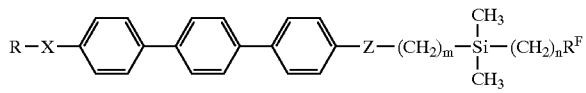

wherein:

m and n are integers ranging from 1 to about 20;

n+m ranges from about 5 to about 20;

one or more non-neighboring carbons in the —(CH$_2$)m— group or the —(CH$_2$)n— group of the silane tail can be replaced with a double bond, a triple bond or an oxygen;

X and Z, independently, are —O— or a single bond;

R is an alkyl or alkenyl group having from 3 to about 20 carbons atoms in which one or more of the non-neighboring carbons can be replaced with an oxygen, or in which one or more of the carbons is substituted with one or more halogens R can be chiral racemic, chiral nonracemic or achiral;

$R^F$ is a perfluorinated alkyl group having from 1 to about 10 carbon atoms.

39. The compound of claim 38 where n is 1 or 2.

40. A liquid crystal composition comprising one or more compounds of formula:

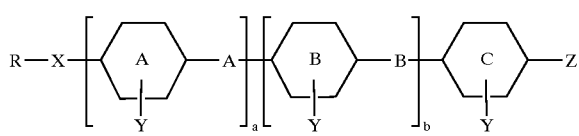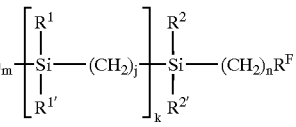

wherein:

a and b can be 1 or 0; k is 0 or an integer ranging from 1–10;

m and n are integers ranging from 1 to about 20;

j is 0 or an integer ranging from 1 to 20, n+m+k(j) ranges from about 5 to about 20;

one or more non-neighboring carbons in the —($CH_2$)m— group or the —($CH_2$)n— group of the silane tail can be replaced with a double bond, a triple bond or an oxygen;

A and B, independently are linker groups selected from the group consisting of a single bond, —COO—, —OOC—, —$CH_2$—$CH_2$—, —$OCH_2$—, —$CH_2$—O—, —CH=CH—, —CH=CH—CH=CH— and —C≡C—;

X and Z, independently, are —O— or a single bond;

Y indicates optional substitution on the core ring and can represent up to four substituents when the rings are aromatic and up to 10 substituents when the rings are alicyclic, sub stituents are selected from halides, CN, $NO_2$, alkyl, or alkoxy;

R is an alkyl or alkenyl group having from 3 to about 20 carbons atoms in which one or more of the non-neighboring carbons can be replaced with an oxygen, or in which one or more of the carbons is substituted with one or more halogens R can be chiral racemic, chiral nonracemic or achiral;

$R^1$, $R^{1'}$, $R^2$ and $R^{2'}$ are alkyl groups or perfluorinated alkyl groups having form 1 to 6 carbon atoms;

$R^F$ is a perfluorinated alkyl group having from 1 to about 10 carbon atoms; and Core rings A, B and C can be aromatic rings or alicyclic rings wherein one or two of the CH or $CH_2$ groups of the ring can be replaced with a nitrogen.

41. A compound having the formula:

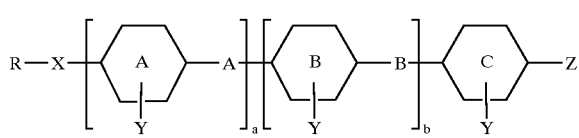

wherein:

a and b can be 1 or 0; k is 0 or an integer ranging from 1–10;

m and n are integers ranging from 1 to about 20;

j is 0 or an integer ranging from 1 to 20, n+m+k(j ) ranges from about 5 to about 20;

one or more non-neighboring carbons in the —($CH_2$)m— group or the —($CH_2$)n— group of the silane tail can be replaced with a double bond, a triple bond or an oxygen;

A and B, independently are linker groups selected from the group consisting of a single bond, —COO—, —OOC—, —$CH_2$—$CH_2$—, —$OCH_2$—, —$CH_2$—O—, —CH=CH—, —CH=CH—CH=CH— and —C≡C—;

X and Z, independently, are —O— or a single bond;

Y indicates optional substitution on the core ring and can represent up to four substituents when the rings are aromatic and up to 10 substituents when the rings are alicyclic, substituents are selected from halides, CN, $NO_2$, alkyl, or alkoxy;

R is an alkyl or alkenyl group having from 3 to about 20 carbons atoms in which one or more of the non-neighboring carbons can be replaced with an oxygen, or in which one or more of the carbons is substituted with one or more halogens R can be chiral racemic, chiral nonracemic or achiral;

$R^1$, $R^{1'}$, $R^2$ and $R^{2'}$ alkyl groups or perfluorinated alkyl groups having form 1 to 6 carbon atoms;

$R^F$ is a perfluorinated alkyl group having from 1 to about 10 carbon atoms; and Core rings A, B and C can be aromatic rings or alicyclic rings wherein one or two of the CH or $CH_2$ groups of the ring can be replaced with a nitrogen.

* * * * *